US011066387B2

(12) United States Patent
Jia et al.

(10) Patent No.: US 11,066,387 B2
(45) Date of Patent: *Jul. 20, 2021

(54) SALTS OF A PIM KINASE INHIBITOR

(71) Applicant: Incyte Corporation, Wilmington, DE (US)

(72) Inventors: Zhongjiang Jia, Kenneth Square, PA (US); Qun Li, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,756

(22) Filed: May 21, 2019

(65) Prior Publication Data

US 2019/0270725 A1  Sep. 5, 2019

Related U.S. Application Data

(63) Continuation of application No. 15/825,306, filed on Nov. 29, 2017, now Pat. No. 10,336,728, which is a continuation of application No. 15/260,695, filed on Sep. 9, 2016, now Pat. No. 9,862,705.

(60) Provisional application No. 62/244,933, filed on Oct. 22, 2015, provisional application No. 62/216,045, filed on Sep. 9, 2015.

(51) Int. Cl.
*C07D 401/14* (2006.01)
*C07F 7/18* (2006.01)
*C07D 401/12* (2006.01)
*A61K 31/4545* (2006.01)

(52) U.S. Cl.
CPC ........ *C07D 401/14* (2013.01); *A61K 31/4545* (2013.01); *C07D 401/12* (2013.01); *C07F 7/1804* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 6,987,116 B2 | 1/2006 | Boschelli et al. | |
| 8,168,794 B2 | 5/2012 | Burger et al. | |
| 8,329,732 B2 | 12/2012 | Burger et al. | |
| 9,200,004 B2 | 12/2015 | Xue | |
| 9,278,950 B2 | 3/2016 | Li et al. | |
| 9,340,546 B2 | 5/2016 | Ahmad | |
| 9,540,347 B2 | 1/2017 | Vechorkin et al. | |
| 9,550,765 B2 | 1/2017 | Xue et al. | |
| 9,556,197 B2 | 1/2017 | Li et al. | |
| 9,580,418 B2 | 2/2017 | Sun et al. | |
| 9,676,750 B2 | 6/2017 | Li et al. | |
| 9,802,918 B2 | 10/2017 | Vechorkin et al. | |
| 9,822,124 B2 | 11/2017 | Vechorkin et al. | |
| 9,849,120 B2 | 12/2017 | Xue et al. | |
| 9,862,705 B2 | 1/2018 | Jia et al. | |
| 9,920,032 B2 | 3/2018 | Vechorkin et al. | |
| 10,000,507 B2 | 6/2018 | Li et al. | |
| 10,265,307 B2 | 4/2019 | Xue et al. | |
| 10,336,728 B2 | 7/2019 | Jia et al. | |
| 10,450,296 B2 | 10/2019 | Vechorkin et al. | |
| 10,517,858 B2 | 12/2019 | Xue et al. | |
| 2011/0059961 A1 | 3/2011 | Wang et al. | |
| 2011/0130418 A1 | 6/2011 | Poncelet et al. | |
| 2012/0114663 A1 | 5/2012 | Gelfand et al. | |
| 2012/0225062 A1 | 9/2012 | Burger et al. | |
| 2013/0057956 A1 | 3/2013 | Iwasa | |
| 2014/0086941 A1 | 3/2014 | Reddy et al. | |
| 2014/0088117 A1 | 3/2014 | Burch et al. | |
| 2014/0163000 A1 | 6/2014 | Ahmad | |
| 2014/0200216 A1 | 7/2014 | Li et al. | |
| 2014/0200227 A1 | 7/2014 | Xue et al. | |
| 2015/0057265 A1 | 2/2015 | Li et al. | |
| 2015/0329534 A1 | 11/2015 | Xue et al. | |
| 2016/0009714 A1 | 1/2016 | Sun et al. | |
| 2016/0009726 A1 | 1/2016 | Vechorkin et al. | |
| 2016/0137626 A1 | 5/2016 | Li et al. | |
| 2016/0347735 A1 | 12/2016 | Vechorkin et al. | |
| 2017/0096411 A1 | 4/2017 | Vechorkin et al. | |
| 2017/0121310 A1 | 5/2017 | Jia et al. | |
| 2017/0158670 A1 | 6/2017 | Vechorkin et al. | |
| 2017/0182017 A1 | 6/2017 | Xue et al. | |
| 2017/0190716 A1 | 7/2017 | Li et al. | |
| 2017/0253587 A1 | 9/2017 | Sun et al. | |
| 2018/0170907 A1 | 6/2018 | Jia et al. | |
| 2018/0193323 A1 | 7/2018 | Xue et al. | |
| 2018/0282302 A1 | 10/2018 | Vechorkin et al. | |
| 2019/0209537 A1 | 7/2019 | Xue et al. | |
| 2020/0002309 A1 | 1/2020 | Vechorkin et al. | |
| 2020/0155527 A1 | 5/2020 | Xue et al. | |

FOREIGN PATENT DOCUMENTS

| | | |
|---|---|---|
| CA | 2668255 | 5/2008 |
| CN | 101568527 | 10/2009 |

(Continued)

OTHER PUBLICATIONS

Amson et al., "The human protooncogene product p33pim is expressed during fetal hematopoiesis snd in diverse leukemias," Proc. Nat. Acad. Sci., USA, 1989, 86:8857-61.

(Continued)

*Primary Examiner* — Samantha L Shterengarts
(74) *Attorney, Agent, or Firm* — Fish & Richardson P.C.

(57) ABSTRACT

The present invention relates to salt forms of the Pim kinase inhibitor N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, including methods of preparation thereof, and intermediates in the preparation thereof, where the compound is useful in the treatment of Pim kinase-related diseases such as cancer.

19 Claims, 46 Drawing Sheets

(56) References Cited

FOREIGN PATENT DOCUMENTS

| | | |
|---|---|---|
| CN | 102985426 | 3/2013 |
| CN | 103664878 | 3/2014 |
| EP | 2637650 | 9/2013 |
| EP | 2743269 | 6/2014 |
| JP | 2010508278 | 3/2010 |
| JP | 2010533716 | 10/2010 |
| JP | 2010535201 | 11/2010 |
| JP | 2012524085 | 10/2012 |
| JP | 2014527959 | 10/2014 |
| WO | WO 2002/000196 | 1/2002 |
| WO | WO 2002/055489 | 7/2002 |
| WO | WO 2002/093173 | 11/2002 |
| WO | WO 2003/106681 | 12/2003 |
| WO | WO 2004/024895 | 3/2004 |
| WO | WO 2004/090106 | 10/2004 |
| WO | WO 2005/028624 | 3/2005 |
| WO | WO 2005/033310 | 4/2005 |
| WO | WO 2006/006569 | 1/2006 |
| WO | WO 2006/071960 | 7/2006 |
| WO | WO 2006/078228 | 7/2006 |
| WO | WO 2007/002433 | 1/2007 |
| WO | WO 2007/011760 | 1/2007 |
| WO | WO 2007/041712 | 4/2007 |
| WO | WO 2007/044724 | 4/2007 |
| WO | WO 2007/048065 | 4/2007 |
| WO | WO 2007/052843 | 5/2007 |
| WO | WO 2007/084857 | 7/2007 |
| WO | WO 2007/131191 | 11/2007 |
| WO | WO 2008/002676 | 1/2008 |
| WO | WO 2008/022164 | 2/2008 |
| WO | WO 2008/045252 | 4/2008 |
| WO | WO 2008/054749 | 5/2008 |
| WO | WO 2008/058126 | 5/2008 |
| WO | WO 2008/082839 | 7/2008 |
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/143759 | 11/2008 |
| WO | WO 2009/014637 | 1/2009 |
| WO | WO 2009/017701 | 2/2009 |
| WO | WO 2009/064486 | 5/2009 |
| WO | WO 2009/065080 | 5/2009 |
| WO | WO 2009/108912 | 9/2009 |
| WO | WO 2009/109576 | 9/2009 |
| WO | WO 2009/151845 | 12/2009 |
| WO | WO 2010/000978 | 1/2010 |
| WO | WO 2010/001169 | 1/2010 |
| WO | WO 2010/002933 | 1/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/048314 | 4/2010 |
| WO | WO 2010/057833 | 5/2010 |
| WO | WO 2010/071885 | 6/2010 |
| WO | WO 2010/135401 | 11/2010 |
| WO | WO 2010/135571 | 11/2010 |
| WO | WO 2010/135581 | 11/2010 |
| WO | WO 2010/135650 | 11/2010 |
| WO | WO 2010/148351 | 12/2010 |
| WO | WO 2011/008487 | 1/2011 |
| WO | WO 2011/025859 | 3/2011 |
| WO | WO 2011/028685 | 3/2011 |
| WO | WO 2011/029802 | 3/2011 |
| WO | WO 2011/031979 | 3/2011 |
| WO | WO 2011/035019 | 3/2011 |
| WO | WO 2011/035022 | 3/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/068667 | 6/2011 |
| WO | WO 2011/075613 | 6/2011 |
| WO | WO 2011/075630 | 6/2011 |
| WO | WO 2011/075643 | 6/2011 |
| WO | WO 2011/079274 | 6/2011 |
| WO | WO 2011/101643 | 8/2011 |
| WO | WO 2011/112662 | 9/2011 |
| WO | WO 2011/124580 | 10/2011 |
| WO | WO 2011/130342 | 10/2011 |
| WO | WO 2011/163195 | 12/2011 |
| WO | WO 2012/004217 | 1/2012 |
| WO | WO 2012/007375 | 1/2012 |
| WO | WO 2012/015474 | 2/2012 |
| WO | WO 2012/016217 | 2/2012 |
| WO | WO 2012/064981 | 5/2012 |
| WO | WO 2012/065297 | 5/2012 |
| WO | WO 2012/065546 | 5/2012 |
| WO | WO 2012/068440 | 5/2012 |
| WO | WO 2012/068450 | 5/2012 |
| WO | WO 2012/078777 | 6/2012 |
| WO | WO 2012/080990 | 6/2012 |
| WO | WO 2012/087881 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/125629 | 9/2012 |
| WO | WO 2012/129338 | 9/2012 |
| WO | WO 2012/135009 | 10/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2012/177606 | 12/2012 |
| WO | WO 2013/013188 | 1/2013 |
| WO | WO 2013/020369 | 2/2013 |
| WO | WO 2013/020370 | 2/2013 |
| WO | WO 2013/020371 | 2/2013 |
| WO | WO 2013/024002 | 2/2013 |
| WO | WO 2013/026025 | 2/2013 |
| WO | WO 2013/033569 | 3/2013 |
| WO | WO 2013/034570 | 3/2013 |
| WO | WO 2013/036611 | 3/2013 |
| WO | WO 2013/041634 | 3/2013 |
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO 2013/151930 | 10/2013 |
| WO | WO 2013/160873 | 10/2013 |
| WO | WO 2013/163279 | 10/2013 |
| WO | WO 2013/170068 | 11/2013 |
| WO | WO 2013/171639 | 11/2013 |
| WO | WO 2013/173720 | 11/2013 |
| WO | WO 2013/175388 | 11/2013 |
| WO | WO 2013/177219 | 11/2013 |
| WO | WO 2013/186692 | 12/2013 |
| WO | WO 2014/001377 | 1/2014 |
| WO | WO 2014/011974 | 1/2014 |
| WO | WO 2014/022752 | 2/2014 |
| WO | WO 2014/033630 | 3/2014 |
| WO | WO 2014/033631 | 3/2014 |
| WO | WO 2014/041131 | 3/2014 |
| WO | WO 2014/048939 | 4/2014 |
| WO | WO 2014/053568 | 4/2014 |

(56) References Cited

FOREIGN PATENT DOCUMENTS

| | | |
|---|---|---|
| WO | WO 2014/060411 | 4/2014 |
| WO | WO 2014/071031 | 5/2014 |
| WO | WO 2014/076162 | 5/2014 |
| WO | WO 2014/079011 | 5/2014 |
| WO | WO 2014/079136 | 5/2014 |
| WO | WO 2014/009447 | 6/2014 |
| WO | WO 2014/089379 | 6/2014 |
| WO | WO 2014/097151 | 6/2014 |
| WO | WO 2014/099880 | 6/2014 |
| WO | WO 2014/100158 | 6/2014 |
| WO | WO 2014/100323 | 6/2014 |
| WO | WO 2014/100719 | 6/2014 |
| WO | WO 2014/106706 | 7/2014 |
| WO | WO 2014/110574 | 7/2014 |
| WO | WO 2014/113388 | 7/2014 |
| WO | WO 2014/134426 | 9/2014 |
| WO | WO 2014/138168 | 9/2014 |
| WO | WO 2014/138906 | 9/2014 |
| WO | WO 2014/138907 | 9/2014 |
| WO | WO 2014/139145 | 9/2014 |
| WO | WO 2014/140597 | 9/2014 |
| WO | WO 2014/140644 | 9/2014 |
| WO | WO 2014/140861 | 9/2014 |
| WO | WO 2014/141171 | 9/2014 |
| WO | WO 2014/142290 | 9/2014 |
| WO | WO 2014/142292 | 9/2014 |
| WO | WO 2014/143601 | 9/2014 |
| WO | WO 2014/143768 | 9/2014 |
| WO | WO 2014/145051 | 9/2014 |
| WO | WO 2014/150258 | 9/2014 |
| WO | WO 2014/150276 | 9/2014 |
| WO | WO 2014/151008 | 9/2014 |
| WO | WO 2014/151634 | 9/2014 |
| WO | WO 2015/021153 | 2/2015 |
| WO | WO 2015/027124 | 2/2015 |
| WO | WO 2015/131031 | 9/2015 |
| WO | WO 2015/157257 | 10/2015 |
| WO | WO 2015/168246 | 11/2015 |
| WO | WO 2015/184305 | 12/2015 |
| WO | WO 2015/191677 | 12/2015 |

OTHER PUBLICATIONS

Arunesh et al., "Small molecule inhibitors of PIM1 kinase. Jul. 2009 to Feb. 2013 patent update," Expert Opin Ther Pat, Jan. 2014, 24(1): 5-17.
Asano et al., "The serine/threonine kinase Pim-2 is a novel anti-apoptotic mediator in myeloma cells," Leukemia, 2011, 25: 1182-1188.
Bamborough, "Assessment of Chemical Coverage of Kinome Space and Its Implications for Kinase Drug Discovery," J. Med. Chem., 2008, 51: 7898-7914.
Baron et al., "PIM1 gene cooperates with human BCL6 gene to promote the development of lymphomas," PNAS, Apr. 2012, 109(15): 5735-5739.
Berge et al., "Pharmaceutical Salts," J. Pharm. Sci., 1977, 66(1):1-19.
Blanco-Aparicio, Biochemical Pharmacology, vol. 85, pp. 629-643, 2013.
Blom et al., "Optimizing Preparative LC-MS Configurations and Methods for Parallel Synthesis Purification," J. Comb. Chem., 2003, 5:670-83.
Blom et al., "Preparative LC-MS Purification: Improved Compound Specific Method Optimization," J. Comb. Chem., 2004, 6:874-883.
Blom, "Two-Pump at Column Dilution Configuration for Preparative Liquid Chromatography—Mass Spectrometry," J. Comb. Chem., 2002, 4:295-301.
Brault et al., "PIM kinases are progression markers and emerging therapeutic targets in diffuse large B-cell lymphoma," British Journal of Cancer, 2012, 107: 491-500.
Burger et al. "Structure Guided Optimization, in Vitro Activity, and in Vivo Activity of Pan-PIM Kinase Inhibitors," ACS Med Chem Lett., 2013, 4:1193-1197.
Caira, "Crystalline Polymorphism of Organic Compounds," Topics in Current Chemistry, Jan. 1998, 198: 163-208.
Cancer [online], [retrieved on Jul. 6, 2007] Retrieved from the Internet, URL: http://www.nlm.nih.gov/medlineplus/cancer.html.
Cervantes-Gomez et al., "Biological Effects of the Pim Kinase Inhibitor, SGI-1776, in Multiple Myeloma," Clinical Lymphoma, Myeloma & Leukemia, Sep. 2013, S317-S329.
Chaichian "Targeted Therapies in Systemic Lupus Erythematosus: A State-of-the-Art-Review" J Clin Cell Immunol 2013, S6, 1-8.
Chan et al., "New N- and O-arylations with phenylboronic acids and cupric acetate," Tetrahedron Letters, May 1998, 39(19): 2933-2936.
Chen et al., "Mechanisms of cytotoxicity to Pim kinase inhibitor, SGI-1776, in acute myeloid leukemia," Blood, Jul. 2011, 118(3): 693-702.
Chen et al., "Pim kinase inhibitor, SGI-1776, induces apoptosis in chronic lymphocytic leukemia cells," Blood, 2009, 114:4150-57.
Chilean Office Action, Patent Application No. 1985-2015, dated Jul. 7, 2016, 22 pages (English Translation).
Chinese Office Action in Chinese Application No. 201480012783.3. dated Sep. 6, 2016, 16 pages (English Translation).
Claudio et al., "A molecular compendium of genes expressed in multiple myeloma," Blood, 2002, 100:2175-86.
Colombian Office Action in Colombian Application No. 15-168. 544, dated Aug. 10, 2016, 10 pages.
Coperet, "A simple and efficient method for the preparation of pyridine N-Oxides," The Journal of Organic Chemistry, Jan. 1998, 63: 1740-1741.
Damia "Contemporary pre-clinical development of anticancer agents—What are the optimal preclinical models?" European Journal of Cancer, 2009, 45, 2768-2781.
Database accession No. RN 1795440-67-3, Chemical Abstracts Service, Jul. 6, 2015, 1 page.
Davis et al., "Small Molecule Dual Antagonist of Pim 1 and 3 Kinases Ameliorate Experimental Autoimmune Encephalomyelitis," $26^{th}$ Congress of the European Committee for Treatment and Research in Multiple Sclerosis, Oct. 13-16, 2010, Gothenburg, Sweden, Poster P436.
Dorwald F. A. Side Reactions in Organic Synthesis, 2005, Wiley: VCH, Weinheim p. IX of Preface p. 1-15.
Eurasian Office Action in Eurasian Application No. 201690458/28, dated Jan. 25, 2017, 11 pages (with English translation).
Eurasian Office Action in Eurasian Application No. 201890663/28, dated Dec. 10, 2018, 8 pages (with English translation).
Freshney, Culture of Animal Cells, A Manual of Basic Technique, Alan R. Liss, Inc., 1983, New York, P4.
Fujii et al., "Aberrant expression of serine-threonine kinase Pim-3 in hepatocellular carcinoma development and its role in the proliferation of human hepatoma cell lines," Int. J. Canc., 2005, 114:209-18.
Georg Pilz, "Modern multiple sclerosis treatment—what is approved, what is on the horizon" Drug Discovery Today Dec. 2008, vol. 13, Nos. 23/24 1013-1025.
Golub et al., "Molecular Classification of Cancer: Class Discovery and Class Prediction by Gene Expression Monitoring," Science, 1999, 286: 531-537.
Gomez-Abad et al., "PIM2 inhibition as a rational therapeutic approach in B-cell lymphoma," Blood, 2011, 118:5517-27.
Gozgit et al., "Effects of the JAK2 Inhibitor, AZ960, on Pim/BAD/BCL-xL Survival Signaling in the Human JAK2 V617F Cell Line SET-2," Journal of Biological Chemistry, Nov. 2008, 283(47): 32334-32343.
Gu and Li, "A concise synthesis of (2S,4R)- and (2S,4S)-4-methylglutamic acid," Tetrahedron Lett., 2003, 44:3203-3205.
Guo et al., "Overexpression of Pim-1 in bladder cancer," J. Experimental & Clinical Cancer Research, 2010, 29: 161-167.
Hammerman et al., "Lymphocyte Transformation by Pim-2 Is Dependent on Nuclear Factor-kB Activation," Cancer Research, Nov. 2004, 64: 8341-8348.
Hsi et al., "Ki67 and PIM1 expression predict outcome in mantle cell lymphoma treated with high dose therapy, stem cell transplantation and rituximab: a Cancer and Leukemia Group B 59909 correlative science study," Leuk. Lymph., 2008, 49:2081-90.

(56) References Cited

OTHER PUBLICATIONS

Hsu et al., "Pim-1 knockdown potentiates paclitaxel-induced apoptosis in human hormone-refractory prostate cancers through inhibition of NHEJ DNA repair," Cancer Lett., 2012, 319:214-222.

Hu et al., "PIM-1—specific mAb suppresses human and mouse tumor growth by decreasing PIM-1 levels, reducing Akt phosphorylation and activating apoptosis," J. Clinical Investigation, Feb. 2009, 119(2):362-375.

Huang et al., "Structure-based design and optimization of 2-aminothiazole-4-carboxamide as a new class of CHK1 inhibitors," Bioorganic Med Chem Lett., Mar. 2013, 23(9):2590-2594.

International Preliminary Report on Patentability in International Application No. PCT/US2014/011486, dated Jul. 21, 2015, 7 pages.

International Preliminary Report on Patentability in International Application No. PCT/US2014/011487, dated Jul. 23, 2015, 6 pages.

International Preliminary Report on Patentability in International Application No. PCT/US2014/052214, dated Feb. 23, 2016, 7 pages.

International Preliminary Report on Patentability in International Application No. PCT/US2015/040146, dated Jan. 17, 2017, 8 pages.

International Preliminary Report on Patentability in International Application No. PCT/US2016/034520, dated Dec. 14, 2017, 7 pages.

International Preliminary Report on Patentability in International Application No. PCT/US2016/050925, dated Mar. 22, 2018, 8 pages.

International Search Report and Written Opinion in International Application No. PCT/US2014/011486, dated Mar. 17, 2014, 12 pages.

International Search Report and Written Opinion in International Application No. PCT/US2014/011487, dated Apr. 4, 2014, 11 pages.

International Search Report and Written Opinion in International Application No. PCT/US2014/052214, dated Oct. 28, 2014, 13 pages.

International Search Report and Written Opinion in International Application No. PCT/US2015/040146, dated Oct. 5, 2015, 12 pages.

International Search Report and Written Opinion in International Application No. PCT/US2016/034520, dated Jul. 12, 2016, 11 pages.

International Search Report and Written Opinion in International Application No. PCT/US2016/050925, dated Oct. 21, 2016, 13 pages.

International Search Report and Written Opinion in International Application No. PCT/US2016/054779, dated Dec. 9, 2016, 12 pages.

Isaac et al., "The oncogenic PIM kinase family regulates drug resistance through multiple mechanisms," Drug Resis. Updates, 2011, 14:203-11.

Ishchenko et al., "Structure-based design of low-nanomolar PIM kinase inhibitors," Bioorg Med Chem Lett., 2015, 25:474-480.

Israeli Office Action in Israel Application No. 244,224, dated May 18, 2018, 8 pages (English Translation).

Jiang et al., "3,5-Disubstituted quinolines as novel c-Jun N-terminal kinase inhibitors," Bioorganic & Medicinal Chemistry Letters, 2007, 17: 6378-6382.

Jin et al., "Expressions of Osteopontin (OPN), anb3 an Pim-1 Associated with Poor Prognosis in Non-small Cell Lung Cancer (NSCLC)," Chin J. Cancer Res, 2012, 24(2): 103-108.

Johnson et al., "Relationship between drug activity in NCI preclinical in vitro and in vivo models and early clinical trials" British Journal of Cancer, 2001, 84, 1424-1437.

Katano et al., "Synthesis and biological activity of cyclopentenopyridinium)thiomethylcephalosporins," The Journal of Antibiotics, Jan. 1990, 43(9): 1150-1159.

Kelly et al., "Targeting PIM kinase activity significantly augments the efficacy of cytarabine," British Journal of Haematology, 2011, 156: 129-152.

Kirschner, "PIM Kinase Inhibitor AZD1208 for Treatment of MYC-Driven Prostate Cancer," JNCI J Natl Cancer Inst, 2015. 107(2): 1-11.

Konstantinos Markrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.

Lala et al., "Role of nitric oxide in tumor progression: Lessons from experimental tumors," Cancer and Metastasis Reviews, 1998, 17: 91-106.

Lam et al., "New aryl/heteroaryl C N bond cross-coupling reactions via arylboronic acid/cupric acetate arylation," Tetrahedron Letters, May 1998, 39(19): 2941-2944.

Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.

Lin et al., "A small molecule inhibitor of Pim protein kinases blocks the growth of precursor T-cell lymphoblastic leukemia/lymphoma," Blood, Jan. 2010, 115(4): 824-833.

Liu et al., "Overexpression of Pim-1 is associated with poor prognosis in patients with esophageal squamous cell carcinoma," J. Surg. Oncol., 2010,102:683-88.

Liu et al., "Synthesis and SAR of 1,9-dihydro-9-hydroxypyrazolo[3,4-b]quinolin-4-ones as novel, selective c-Jun N-terminal kinase inhibitors," Bioorganic & Medicinal Chemistry Letters, 2006, 16: 2590-2594.

Lu et al., "Pim2 is required for maintaining multiple myeloma cell growth through modulating TSC2 phosphorylation," Blood, Aug. 2013, 122(9): 1610-1620.

Mahalingam et al., "Targeting PIM kinase enhances the activity of sunitinib in renal cell carcinoma," British J. Cancer, Oct. 2011, 105: 1563-1573.

Magnuson, "Why target PIM1 for cancer diagnosis and treatment?" Future Oncol., Sep. 2010. 6(9): 1461-1478.

Martin-Sanchez et al., "HDAC inhibitors induce cell cycle arrest, activate the apoptotic extrinsic pathway and synergize with a novel PIM inhibitor in Hodgkin lymphoma-derived cell lines," British J. Haematology, 2010, 152:347-362.

Merkel et al., "PIM1 kinase as a target for cancer therapy," Exp. Opin. Investig. Drugs, 2012, 21:415-38.

Michelotti et al., "Two classes of p38a MAP kinase inhibitors having a common diphenylether core but exhbiting divergent binding modes," 2005, 15: 5274-5279.

Mikkers et al., "High-throughput retroviral tagging to identify components of specific signaling pathways in cancer," Nature Genet., 2002, 32:153-159.

Mikkers et al., "Mice deficient for all PIM kinases display reduced body size and impaired responses to hematopoietic growth factors," Mol. Cell. Biol., 2004, 24:6104-15.

Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorganic & Medicinal Chemistry Letters, 2007, 17: 250-254.

Mizuki et al., "Suppression of myeloid transcription factors and induction of STAT response genes by AML-specific Flt3 mutations," Blood, 2003, 101:3164-73.

Morwick, "Pim kinase inhibitors: a survey of the patent literature," Exp. Opin. Ther. Patents, 2010, 20(2):193-212.

Mukaida et al., "Roles of Pim-3, a novel survival kinase, in tumorgenesis," Cancer Science, Aug. 2011, 102(8):1437-1442.

Mulvihill et al., "Novel 2-phenylquinolin-7-yl-derived imidazo [1,5-a]pyrazines as potent insulin-like growth factor-I receptor (IFG-IR) inhibitors," Bioorganic & Medicinal Chemistry, 2008, 16: 1359-1375.

Ocana, A. "Preclinical development of molecular targeted agents for cancer" Nat. Rev. Clin. Oncol. 2011, 8, 200-209.

Ogawa et al., "Insights from Pim1 structure for anti-cancer drug design," Expert Opin Drug Discov, Dec. 2012, 7(12): 1177-92.

(56) References Cited

OTHER PUBLICATIONS

Peltola et al., "Pim-1 kinase expression predicts radiation response in squamocellular carcinoma of head and neck and is under the control of epidermal growth factor receptor," Neoplasia, 2009, 11:629-36.
Peturssion, "Protecting Groups in Carbohydrate Chemistry," J. Chem. Educ., 1997, 74(11):1297-1303.
Ravin, "Preformulation," Remington's Pharmaceutical Sciences, 17th Ed., (Mack Publishing Company, Easton, 1985), p. 1409-1423.
Robinson et al., "A Dual PIM 1/3 Kinase Inhibitor Demonstrates Efficacy in Murine Models of Lupus and Multiple Sclerosis," J. Immunol., 2012, 188:119.9.
Schatz, et al., "Targeting cap-dependent translation blocks converging survival signals by AKT and PIM kinases in lymphoma," J. Exp. Med., 2011, 208:1799-1807.
Schwemmers et al., "JAK2$^{V617F}$-negative ET Patients do not display constitutively active JAK/STAT signaling," Exp. Hematol., Nov. 2007, 35(11): 1695-1703.
Search Report, dated Jul. 2, 2014, 6 pages.
Search Report, dated Jul. 3, 2014, 4 pages.
Search Report, dated Jul. 8, 2014, 4 pages.
Sharma "Cell line-based platforms to evaluate the therapeutic efficacy of candidate anticancer agents" Nature Reviews Cancer Apr. 2010, vol. 10, 241-253.
Shen et al., "Inhibition of Pim-1 kinase ameliorates dextran sodium sulfate-induced colitis in mice,", Dig. Dis. Sci., 2012, 57:1822-31.
Shinto et al., "Moloney murine leukemia virus infection accelerates lymphomagenesis in Eµ-bcl-2 transfenic mice," Oncogene, 1995, 11:1729-36.
Simone, Oncology: Introduction, Cecil Textbook of Medicine, 20th Edition, 1996 vol. 1, pp. 1004-1010.
Swords et al., "The Pim kinases: new targets for drug development," Curr. Drug Targets, 2011, 12(14):2059-66.
United States Office Action in U.S. Appl. No. 14/155,134, dated Jul. 27, 2015, 12 pages.
Venkatesh et al., "Role of the Development Scientist in Compound Lead Selection and Optimization," J. Pharm. Sci., 2000, 89:145-54.
Wang et al "Inhibition of Pim1 kinase prevents peanut allergy by enhancing Runx3 expression and suppressing T(H)2 and T(H)17 T-cell differentiation," J. All. Clin. Immunol., 2012, 130:932-44.
www.leukaemia.org [online]. "Myeloproliferative neoplasms (MPN)," 2016, [retrieved on Dec. 5, 2016]. Retrieved from the Internet: URL<http://www.leukaemia.org.au/blood-cancers/myeloproliferative-neoplasms-mpn>, 3 pages.
Yan et al., "Clinical and therapeutic relevance of PIM1 kinase in gastric cancer," Gastric Cancer, 2012, 15:188-197.
Yang et al., "Proviral integration site 2 is required for interleukin-6 expression induced by interleukin-1, tumour necrosis factor-α and lipopolysaccharide," Immunol., 2010, 131:174-182.
Zippo, et al., "PIM1-dependent phosphorylation of histone H3 at serine 10 is required for MYC-dependent transcriptional activation and oncogenic transformation," Nature Cell Biol., 2007, 9:932-44.
Argentina Office Action in Argentina Application No. P140100129, dated Nov. 27, 2019, 10 pages (English Translation).
Australian Office Action in Australian Application No. 2014207691, dated Aug. 17, 2017, 4 pages.
Australian Office Action in Australian Application No. 2018217210, dated Feb. 22, 2019, 4 pages.
Brazilian Office Action in Brazilian Application No. BR112015016793-4, dated Sep. 19, 2019, 5 pages (English Translation).
Chinese Office Action in Chinese Application No. 201480057613.7, dated Apr. 5, 2017, 15 pages (English Translation).
Chilean Office Action in Chilean Application No. 1985-2015, dated Mar. 23, 2017, 13 pages (English Translation).
Chilean Office Action in Chilean Application No. 201600398, dated Jul. 27, 2017, 16 pages (English Translation).
Chilean Office Action in Chilean Application No. 611-2018. dated May 16, 2019, 21 pages (English Translation).
Colombian Office Action in Colombian Application No. 16-070.957, dated Sep. 13, 2017, 7 pages (English Translation).
Costa Rican Office Action in Costa Rican Application No. 2015-0412 dated Jul. 12, 2019, 14 pages.
Eurasian Office Action in Eurasian Application No. 201591339, dated Nov. 5, 2019, 2 pages.
Eurasian Office Action in Eurasian Application No. 201591339, dated Mar. 26, 2019, 4 pages.
European Office Action in European Application No. 14702389.9-1109, dated Jun. 11, 2018.
Israeli Office Action in Israeli Application No. 239,886, dated Apr. 2, 2019, 4 pages.
Israeli Office Action in Israeli Application No. 239,886, dated Dec. 16, 2019, 9 pages.
Indian Office Action in Indian Application No. 201627008738, dated May 16, 2019, 6 pages.
Japanese Office Action in Japanese Application No. 2015-552896, dated Nov. 28, 2017, 8 pages (English Translation).
Japanese Office Action in Japanese Application No. 2016-536470, dated Apr. 24, 2018, 4 pages (English Translation).
Malaysian Office Action in Malaysian Application No. PI 2015001776, dated Jul. 22, 2019, 2 pages.
Mexican Office Action in Mexican Application No. MX/a/2015/009057, dated Dec. 9, 2019, 3 pages.
New Zealand Office Action in New Zealand Application No. 749911, dated Jul. 19, 2019, 4 pages.
New Zealand Office Action in New Zealand Application No. 749911, dated Oct. 7, 2019, 2 pages.
Peruvian Office Action in Peruvian Application No. 1345.15, dated Mar. 21, 2019, 18 pages.
Philippine Office Action in Philippine Office Application No. 1/2015/501567, dated Jan. 13, 2020, 2 pages.
Taiwanese Office Action in Taiwanese Application No. 103101314, dated Dec. 28, 2017, 18 pages (English Translation).
Ukraine Office Action in Ukraine Application No. a 201508119, dated Jul. 15, 2019, 8 pages.
Ukraine Grant in Ukraine Application No. a201508119, dated Nov. 21, 2019, 6 pages.
Vietnamese Office Action in Vietnamese Application No. 48930/SHTT-SC, dated Dec. 28, 2018, 2 pages (English Translation).
Bastin et al., "Salt Selection and Optimisation Procedures for Pharmaceutical New Chemical Entities," Org Proc Res Dev., Jul. 19, 2000, 4(5):427-435.
Morissette et al., "High-Throughput Crystallization. polymorphs, salts, co-crystals and solvates of pharmaceutical solids," Advanced Drug Delivery Reviews, Feb. 23, 2004, 56:375-300.
Canadian Office Action in Canadian Application No. 2897200, dated Feb. 14, 2020, 4 pages.
Chilean Office Action in Chilean Application No. 2079-2019, dated May 15, 2020, 28 pages.
Colombian Office Action in Colombian Application No. NC2018/0003739, dated Apr. 1, 2020, 27 pages.
Indonesian Office Action in Indonesian Application No. P00201807826, dated Apr. 17, 2020, 7 pages.
Indonesian Office Action in Indonesian Application No. PID201802590, dated Mar. 27, 2020, 6 pages.
Chinese Office Action in Chinese Office Application No. 201680057727.0, dated Aug. 18, 2020, 13 pages.
Japanese Office Action in Japanese Application No. 2018-512592, dated Aug. 25, 2020, 14 pages.
Takashi Kojima, "Iyalcuhin Kaihatu niokeru kesyosei sentaku no kourituka wo mezasite (documents indicating well-known arts) for the purpose of improving the selection of a crystalline selection in the development of small or pharmaceutical drug and pharmaceutical drug development," Medicine, Sep. 1, 2008, 68(5):344-349.
Noriaki Hirayama, "Handbook for organic compound crystal preparation—Principle and know-how," Marzen Co. Ltd., Jul. 25, 2008, p. 57-84.
Teruzo Asahara, "Solvent Handbook," Incorporated Company Kodansha, 1985, p. 47-51.
Colombian Office Action in Colombian Application No. NC2018/0003739, dated Oct. 13, 2020, 17 pages.
Paulekuhn et al., "Trends in Active Pharmaceutical Ingredient Salt Selection based on Analysis of the Orange Book Database," J Med Chem., 2007, 50(26):6665-6672.

(56) References Cited

OTHER PUBLICATIONS

Malaysian Office Action in Malaysian Application No. PI 2018000356, dated Nov. 9, 2020, 3 pages.
Taiwanese Office Action in Taiwanese Application No. 105129102, dated Oct. 30, 2020, 12 pages.
Brittain, "Polymorphism in Pharmaceutical Solids,"CRC Press. Marcel Dekker, Inc., New York, 2009, pp. 333-334.
usp.org, "Characterization of Crystalline and Partially Crystalline Solids by XRay Powder Diffraction (XRPD)," dated Nov. 23, 2016 [retrieved on Dec. 30, 2020], retrieved from URL <https://www.usp.org/sites/default/files/usp/document/harmonization/genchapter/g14_pf_35_3_2009.pdf>, 11 pages.
Australian Office Action in Australian Application No. 2016/320892, dated Dec. 2, 2020, 4 pages.
Ukraine Office Action in Ukraine Application No. a201803689, dated Dec. 18, 2020, 11 pages.
Chilean Office Action in Chilean Application No. 2078-2019, dated Dec. 15, 2020, 28 pages.
Anderson and Flora, "Preparation of Water-Soluble Organic Compounds Through Salt Formation," Practice of Medicinal Chemistry, Wermuth (Ed.), 1999, vol. 2:347-365.
European Office Action in European Application No. 16770411.3, dated Mar. 11, 2021, 3 pages.
Mano, "Pharmaceutical Research in the Early Stages of Drug DiscoverySignificance and Practice," Japanese Pharmacological Society, Mar. 1, 2009, 133(3):149-153.
Australian Notice of Allowance in Australia Application No. 2016320892, dated Feb. 26, 2021, 8 pages.
Japanese Office Action in Japanese Application No. 2018-512592, dated Mar. 9, 2021, 10 pages.
Thailand Office Action in Thailand Application No. 1801001409, dated Mar. 11, 2021, 3 pages.

SALTS OF A PIM KINASE INHIBITOR

FIELD OF THE INVENTION

The present invention relates to salt forms of the Pim kinase inhibitor N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, including methods of preparation thereof, and intermediates in the preparation thereof, where the compound is useful in the treatment of Pim kinase-related diseases such as cancer.

BACKGROUND OF THE INVENTION

Overexpression of Pim kinases is detected in a wide variety of hematologic and solid cancers. Overexpression of various family members have been noted in multiple myeloma, AML, pancreatic and hepatocellular cancers. Claudio et al., *Blood* 2002, 100, 2175-86; Amson et al., *Proc. Nat. Acad. Sci. USA,* 1989, 86, 8857-61; Mizuki et al., *Blood,* 2003, 101, 3164-73; Li et al., *Canc. Res.,* 2006, 66, 6741-7; Fujii et al., *Int. J. Canc.,* 2005, 114, 209-18. Pim1 overexpression is associated with poor prognosis in mantle cell lymphoma, esophageal and head and neck cancers. Hsi et al., *Leuk. Lymph.,* 2008, 49, 2081-90; Liu et al., *J. Surg. Oncol.,* 2010, 102, 683-88; Peltola et al., *Neoplasia,* 2009, 11, 629-36. Pim2 overexpression is associated with an aggressive clinical course in a subset of DLBCL patients. Gomez-Abad et al., *Blood,* 2011, 118, 5517-27. Overexpression is often seen where Myc is overexpressed and Pim kinases can convey resistance to traditional chemotherapeutic agents and radiation. Chen et al., *Blood,* 2009, 114, 4150-57; Isaac et al., *Drug Resis. Updates,* 2011, 14, 203-11; Hsu et al., *Cancer Lett.,* 2012, 319, 214; Peltola et al., *Neoplasia,* 2009, 11, 629-36. As such, these data indicate that inhibition of Pim kinases will be useful to provide therapeutic benefit in cancer patients.

Pim kinase inhibitors have been described in, for example, US Pat. Pub. Nos. 2014/0200216, 2014/0200227, and 2015/0057265. In particular, the Pim-inhibiting compound N-{4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (including both 7R and 7S diastereomers) is described in US Pat. Pub. No. 2014/0200227. Accordingly, new forms of Pim-inhibiting molecules are needed to help prepare pharmaceutically useful formulations and dosage forms with suitable properties related to, for example, facilitating the manufacture of safe, effective, high quality drug products. The present invention described herein is directed toward this end.

SUMMARY OF THE INVENTION

The present invention is directed to salts of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

The present invention is further directed to the phosphoric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

The present invention is further directed to crystalline forms of the phosphoric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

The present invention is further directed to the dihydrochloric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

The present invention is further directed to the monohydrochloric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

The present invention is further directed to the maleic acid salt, adipic acid salt, hydrobromic acid salt, (R)-(−)-mandelic acid salt, salicylic acid salt, benzoic acid salt, pyroglutamic acid salt, methanesulfonic acid salt, (1S)-(+)-10-camphorsulfonic acid salt, fumaric acid salt, sulfuric acid salt, L-tartaric acid salt, and D-tartaric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

The present invention is further directed to crystalline forms of the salts described herein.

The present invention is further directed to pharmaceutical compositions comprising a salt or crystalline form described herein, and at least one pharmaceutically acceptable carrier.

The present invention is further directed to therapeutic methods of using the salts and crystalline forms described herein.

The present invention is further directed to processes for preparing the salts and crystalline forms described herein.

The present invention is further directed to intermediates useful in the preparation of the salts and crystalline forms described herein.

DETAILED DESCRIPTION

Figure 1:
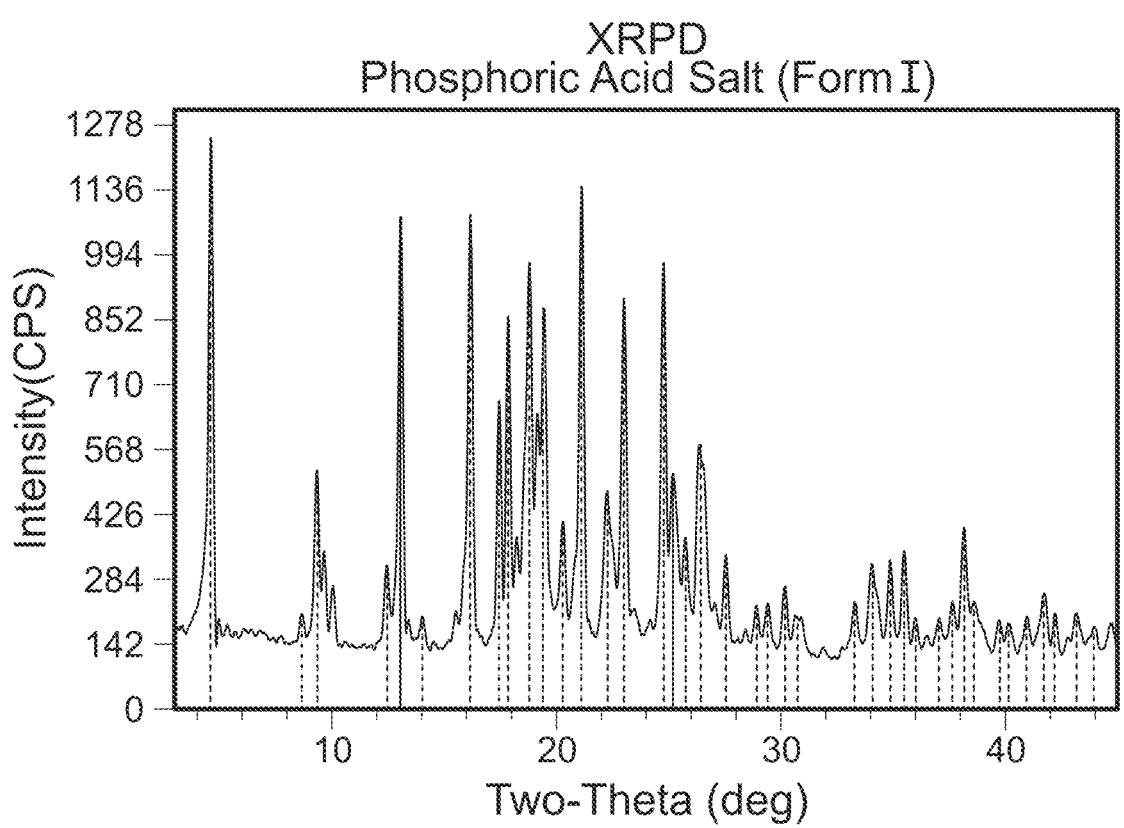
FIG. 1 shows the XRPD pattern of Compound 1 phosphoric acid salt Form I.

The present invention is directed to, inter alia, salts of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1), the structure of which is shown below.

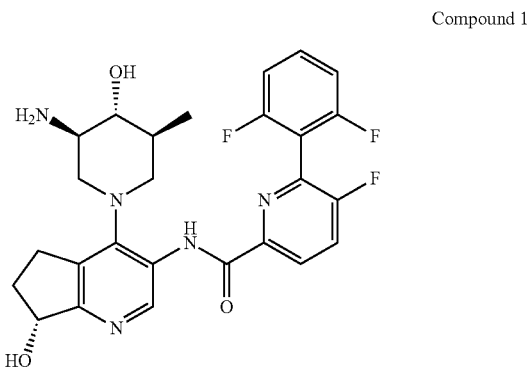 [SMILES: C[C@H]1CN(c2c(NC(=O)c3ccc(F)c(-c4c(F)cccc4F)n3)cnc3c2CC[C@H]3O)C[C@@H](N)[C@@H]1O]

Compound 1

Compound 1 and its salts are a Pim kinase inhibitors useful in the treatment of diseases in which, for example, one or more Pim kinases (e.g., Pim 1, Pim2, and/or Pim 3) is upregulated. In some embodiments, the salt of Compound 1 provided herein is a solid form. In some embodiments, the present invention relates to a solid form comprising a salt provided herein. In some embodiments, the solid form is crystalline.

In some embodiments, the salt of the invention is a phosphoric acid salt of Compound 1, such as a monophosphoric acid salt form. The monophosphoric acid salt form of Compound 1 is referred to herein as "Compound 1 phosphoric acid salt," "Compound 1 phosphoric acid," or "Compound 1 phosphate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide phosphate.

In some embodiments, the salt of the invention is a hydrochloric acid salt of Compound 1, such as a dihydrochloric acid salt form. The dihydrochloric acid salt form of Compound 1 is referred to herein as "Compound 1 dihydrochloric acid salt," "Compound 1 dihydrochloric acid," or "Compound 1 dihydrochloride." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide dihydrochloride.

In some embodiments, the hydrochloric acid salt of Compound 1 is a monohydrochloric acid salt of Compound 1. The monohydrochloric acid salt form of Compound 1 is referred to herein as "Compound 1 monohydrochloric acid salt," "Compound 1 monohydrochloric acid," or "Compound 1 monohydrochloride." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide mono-hydrochloride.

In some embodiments, the salt of the invention is a maleic (cis-butenedioic) acid salt of Compound 1. The maleic acid salt form of Compound 1 is referred to herein as "Compound 1 maleic acid salt," "Compound 1 maleic acid," or "Compound 1 maleate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide maleate.

In some embodiments, the salt of the invention is an adipic acid salt of Compound 1. The adipic acid salt form of Compound 1 is referred to herein as "Compound 1 adipic acid salt," "Compound 1 adipic acid," or "Compound 1 adipate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide adipate.

In some embodiments, the salt of the invention is a hydrobromic acid salt of Compound 1. In some embodiments, the hydrobromic acid salt of Compound 1 a dihydrobromic acid salt form. In some embodiments, the hydrobromic acid salt of Compound 1 a monohydrobromic acid salt form. The hydrobromic acid salt form of Compound 1 is referred to herein as "Compound 1 hydrobromic acid salt," "Compound 1 hydrobromic acid," or "Compound 1 hydrobromide." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide hydrobromide.

In some embodiments, the salt of the invention is a (R)-(−)-mandelic acid salt of Compound 1. In some embodiments, the (R)-(−)-mandelic acid salt of Compound 1 is a mono-(R)-(−)-mandelic acid salt. In some embodiments, the (R)-(−)-mandelic acid salt of Compound 1 is a di-(R)-(−)-mandelic acid salt. The (R)-(−)-mandelic acid salt form of Compound 1 is referred to herein as "Compound 1 mandelic acid salt," "Compound 1 mandelic acid," or "Compound 1 mandelate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide mandelate.

In some embodiments, the salt of the invention is a salicylic acid salt of Compound 1. In some embodiments, the salicylic acid salt of Compound 1 is a mono-salicylic acid salt. In some embodiments, the salicylic acid salt of Compound 1 is a di-salicylic acid salt. The salicylic acid salt form of Compound 1 is referred to herein as "Compound 1 salicylic acid salt," "Compound 1 salicylic acid," or "Compound 1 salicylate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide salicylate.

In some embodiments, the salt of the invention is a benzoic acid salt of Compound 1. In some embodiments, the benzoic acid salt of Compound 1 is a mono-benzoic acid salt. In some embodiments, the benzoic acid salt of Compound 1 is a di-benzoic acid salt. The benzoic acid salt form of Compound 1 is referred to herein as "Compound 1 benzoic acid salt," "Compound 1 benzoic acid," or "Compound 1 benzoate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide benzoate.

In some embodiments, the salt of the invention is a benzenesulfonic acid salt of Compound 1. In some embodiments, the benzenesulfonic acid salt of Compound 1 is a mono-benzenesulfonic acid salt. In some embodiments, the benzenesulfonic acid salt of Compound 1 is a di-benzenesulfonic acid salt. The benzenesulfonic acid salt form of Compound 1 is referred to herein as "Compound 1 benzenesulfonic acid salt," "Compound 1 benzenesulfonic acid," or "Compound 1 besylate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide besylate.

In some embodiments, the salt of the invention is L-pyroglutamic acid salt of Compound 1. In some embodiments, the L-pyroglutamic acid salt of Compound 1 is a mono-L-pyroglutamic acid salt. In some embodiments, the L-pyroglutamic acid salt of Compound 1 is a di-L-pyroglutamic acid salt. The L-pyroglutamic acid salt form of Compound 1 is referred to herein as "Compound 1 L-pyroglutamic acid salt," "Compound 1 L-pyroglutamic acid," or "Compound 1 L-pyroglutamate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide L-pyroglutamate.

In some embodiments, the salt of the invention is a methanesulfonic acid salt of Compound 1. In some embodiments, the methanesulfonic acid salt of Compound 1 is a mono-methanesulfonic acid salt form. In some embodiments, the methanesulfonic acid salt of Compound 1 is a di-methanesulfonic acid salt form. The methanesulfonic acid salt form of Compound 1 is referred to herein as "Compound 1 methanesulfonic acid salt," "Compound 1 methanesulfonic acid," or "Compound 1 mesylate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide mesylate.

In some embodiments, the salt of the invention is a (1S)-(+)-10-camphorsulfonic acid salt of Compound 1. In some embodiments, the (1S)-(+)-10-camphorsulfonic acid salt of Compound 1 is a mono-(1S)-(+)-10-camphorsulfonic acid salt. In some embodiments, the (1S)-(+)-10-camphorsulfonic acid salt of Compound 1 is a (1S)-(+)-10-di-camphorsulfonic acid salt. The (1S)-(+)-10-camphorsulfonic acid salt form of Compound 1 is referred to herein as "Compound 1 (1S)-(+)-10-camphorsulfonic acid salt," "Compound 1 (1S)-(+)-10-camphorsulfonic acid," or "Compound 1 camsylate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide camsylate.

In some embodiments, the salt of the invention is a fumaric (trans-butenedioic) acid salt of Compound 1. The fumaric acid salt form of Compound 1 is referred to herein as "Compound 1 fumaric acid salt," "Compound 1 fumaric acid," or "Compound 1 fumarate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide fumarate.

In some embodiments, the salt of the invention is a sulfuric acid salt of Compound 1. In some embodiments, the sulfuric acid salt of Compound 1 is a mono-sulfuric acid salt form. The sulfuric acid salt form of Compound 1 is referred to herein as "Compound 1 sulfuric acid salt," "Compound 1 sulfuric acid," or "Compound 1 sulfate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide sulfate.

In some embodiments, the salt of the invention is a tartaric acid salt of Compound 1, such as L-tartaric acid salt form. The L-tartaric acid salt form of Compound 1 is referred to herein as "Compound 1 L-tartaric acid salt," "Compound 1 L-tartaric acid," or "Compound 1 L-tartrate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide L-tartrate.

In some embodiments, the tartaric acid salt of Compound 1 is D-tartaric acid salt of Compound 1. The D-tartaric acid salt form of Compound 1 is referred to herein as "Compound 1 D-tartaric acid salt," "Compound 1 D-tartaric acid," or "Compound 1 D-tartrate." An alternative name for the salt is N—{(R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropicolinamide D-tartrate.

The salts of the invention can be isolated as one or more solid forms. As used herein, the phrase "solid form" refers to a salt of the invention in either an amorphous state or a crystalline state ("crystalline form" or "crystalline solid"), whereby a salt of the invention in a crystalline state may optionally include solvent or water within the crystalline lattice, for example, to form a solvated or hydrated crystalline form. The term "hydrated," as used herein, is meant to refer to a crystalline form that includes water molecules in the crystalline lattice. Example "hydrated" crystalline forms include hemihydrates, monohydrates, dihydrates, and the like. Other hydrated forms such as channel hydrates and the like are also included within the meaning of the term.

The different crystalline forms of the salts of the invention are characterized by X-ray powder diffraction (XRPD), differential scanning calorimetry (DSC), and/or thermogravimetric analysis (TGA). An X-ray powder diffraction (XRPD) pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear depending on the type of instrument or the settings (for example, whether a Ni filter is used or not). As used herein, the term "peak" or "characteristic peak" refers to a reflection having a relative height/intensity of at least about 3% of the maximum peak height/intensity. Moreover, instrument variation and other factors can affect the 2-theta values. Thus, peak assignments, such as those reported herein, can vary by plus or minus about 0.2° (2-theta), and the term "substantially" or "about" as used in the context of XRPD herein is meant to refer to the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

The salts and compounds disclosed herein can include all isotopes of atoms occurring within them. Isotopes include those atoms having the same atomic number but different mass numbers. For example, isotopes of hydrogen include tritium and deuterium. Salts and compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

In some embodiments, the compounds of the invention, or salts thereof, are substantially isolated. By "substantially isolated" is meant that the compound or salt is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds or salts of the invention.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "melting point" refers to an endothermic event or endothermal event observed in e.g., a DSC experiment. An endothermic event is a process or reaction in which a sample absorbs energy from its surrounding in the form of e.g., heat as in a DSC experiment. An exothermic event is a process or reaction in which a sample releases energy. The process of heat absorption and release can be detected by DSC. In some embodiments, the term "melting point" is used to describe the major endothermic event revealed on a particular DSC thermogram.

The term "room temperature" as used herein, is understood in the art, and refers generally to a temperature, e.g., a reaction temperature, that is about the temperature of the room in which the reaction is carried out, for example, a temperature from about 20° C. to about 30° C. The term "elevated temperature" as used herein, is understood in the art, and refer generally to a temperature, e.g., a reaction temperature, that is above room temperature, e.g., above 30° C.

Phosphoric Acid Salt

The present invention is directed to, inter alia, a phosphoric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, such as the salt which is shown below.

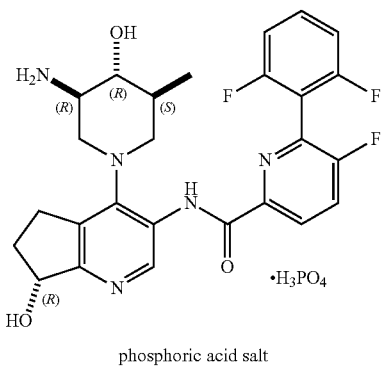

Compound 1 phosphoric acid salt

Figure 2:
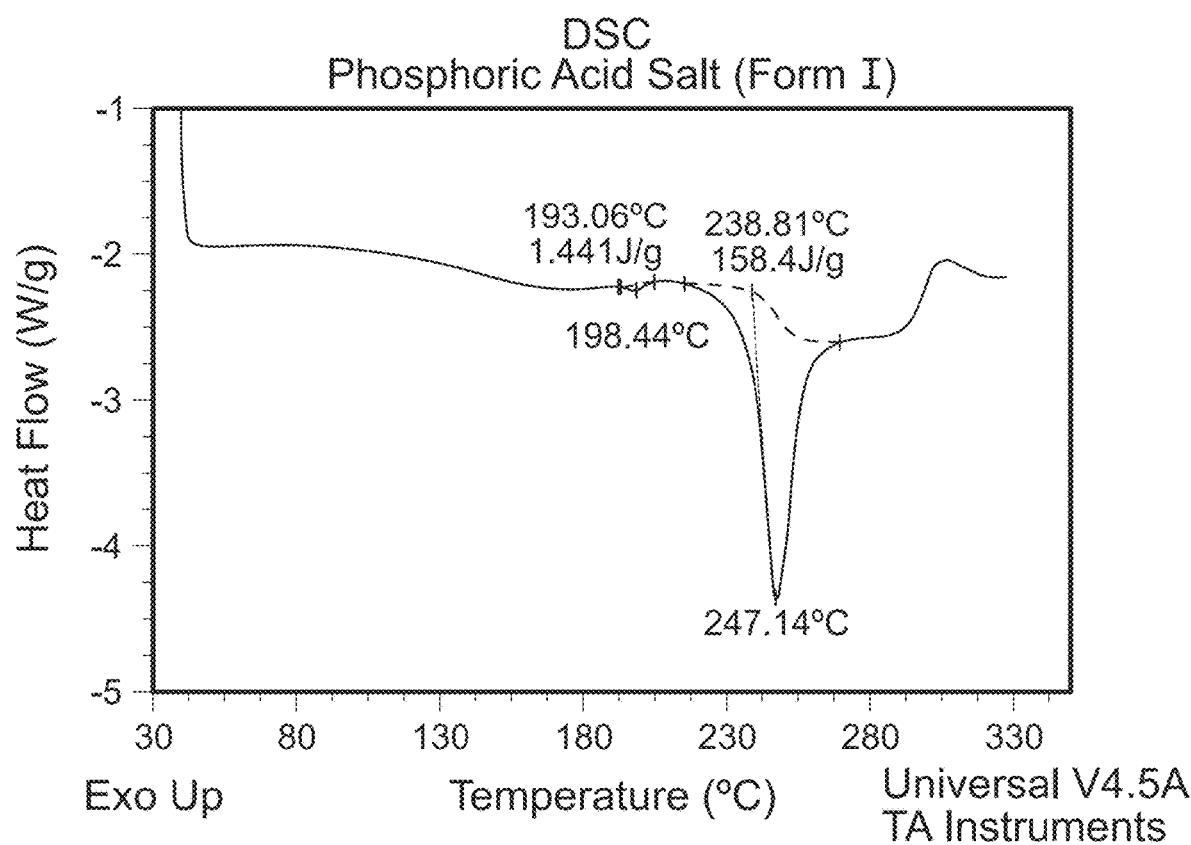
FIG. 2 shows the DSC thermogram of Compound 1 phosphoric acid salt Form I.
Figure 3:
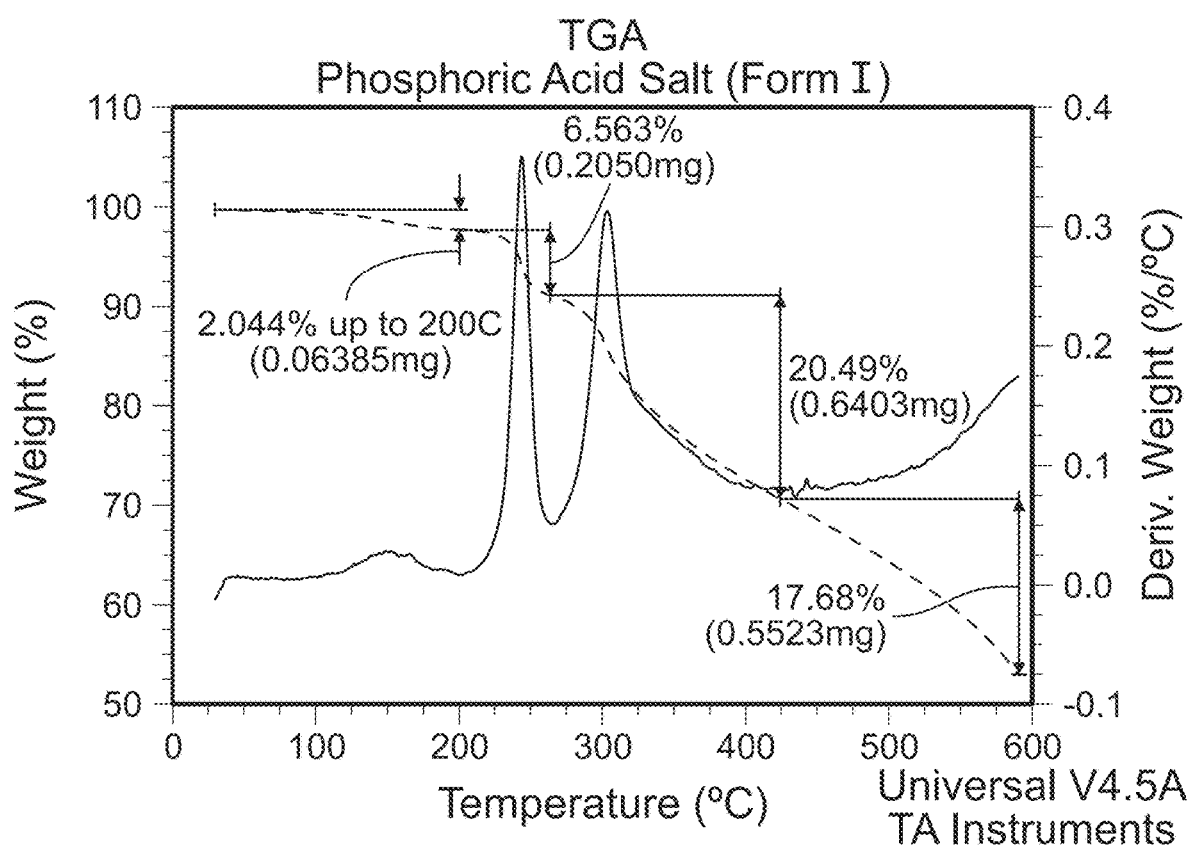
FIG. 3 shows the TGA thermogram of Compound 1 phosphoric acid salt Form I.

Compound 1 phosphoric acid salt can be prepared as an amorphous solid, as a crystalline solid, or as a mixture thereof. In some embodiments, the crystalline solid has Form I, which is described below in the Examples. In some embodiments, the crystalline solid having Form I has a characteristic XRPD peak, in terms of 2-theta, at about 4.6 degrees. In some embodiments, the crystalline solid having Form I has at least one characteristic XRPD peak, in terms of 2-theta, at about 4.6 or about 9.4 degrees. In some embodiments, the crystalline solid having Form I has at least one characteristic XRPD peak, in terms of 2-theta, at about 4.6, about 9.4, or about 13.1 degrees. In some embodiments, the crystalline solid of Form I has two or more characteristic XRPD peaks, in terms of 2-theta, selected from about 4.6, about 9.4, about 13.1, about 16.2, about 17.4, about 17.9, about 18.8, about 19.4, about 21.1, about 23.0, and about 24.8. In some embodiments, the crystalline solid of Form I has three or more characteristic XRPD peaks, in terms of 2-theta, selected from about 4.6, about 9.4, about 13.1, about 16.2, about 17.4, about 17.9, about 18.8, about 19.4, about 21.1, about 23.0, about 24.8, and about 25.2 degrees. In some embodiments, the crystalline solid of Form I has four or more characteristic XRPD peaks, in terms of 2-theta, selected from about 4.6, about 9.4, about 13.1, about 16.2, about 17.4, about 17.9, about 18.8, about 19.4, about 21.1, about 23.0, about 24.8, about 25.2 degrees. In some embodiments, the crystalline solid of Form I has an XRPD pattern substantially as depicted in FIG. 1. In some embodiments, the crystalline solid of Form I has a melting point of about 250° C. In some embodiments, the crystalline solid of Form I has an endothermic event at about 198° C. or about 250° C. In some embodiments, the crystalline solid of Form I has a DSC thermogram substantially as depicted in FIG. 2. In some embodiments, the crystalline solid of Form I has a TGA thermogram substantially as depicted in FIG. 3.

The advantages of the phosphoric acid salt include high crystallinity, high melting point, stable crystalline form (e.g., Form I), and non-hygroscopic properties, each of which facilitate the purification, reproducibility, scale up, manufacturing, and formulation of the drug compound.

Figure 7:
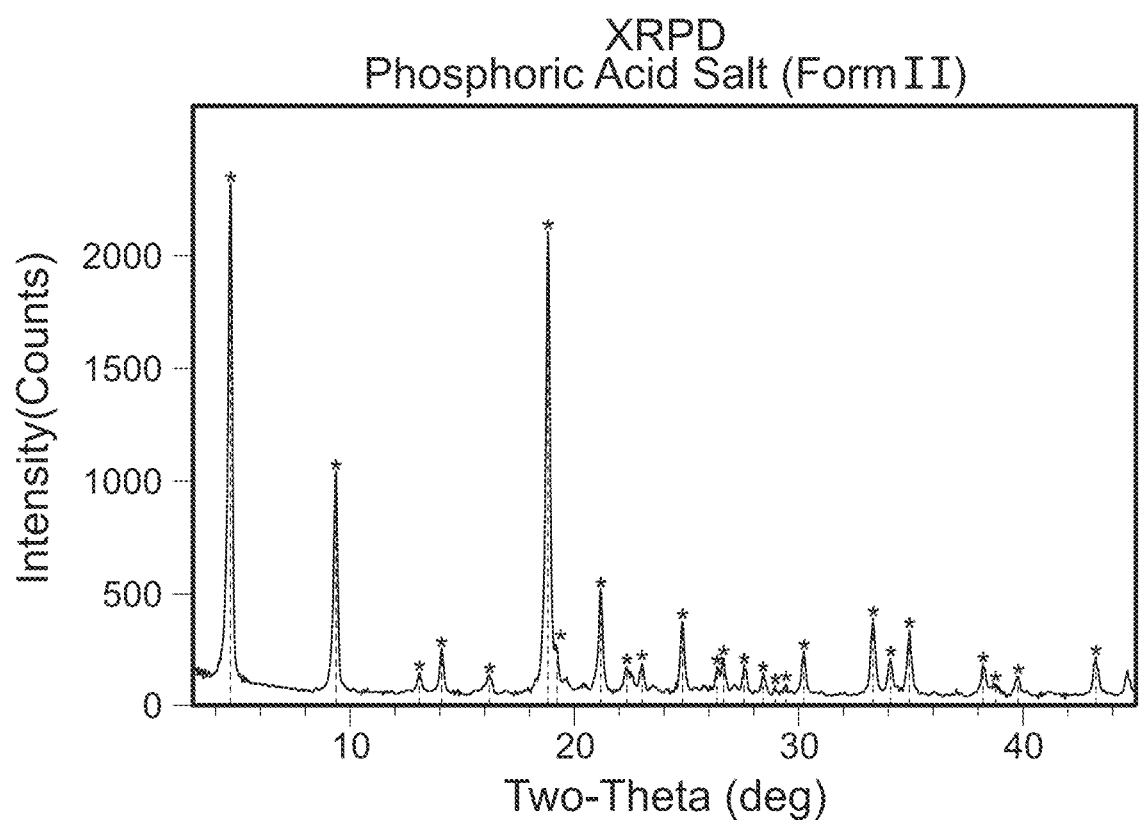
FIG. 7 shows the XRPD pattern of Compound 1 phosphoric acid salt Form II.
Figure 8:
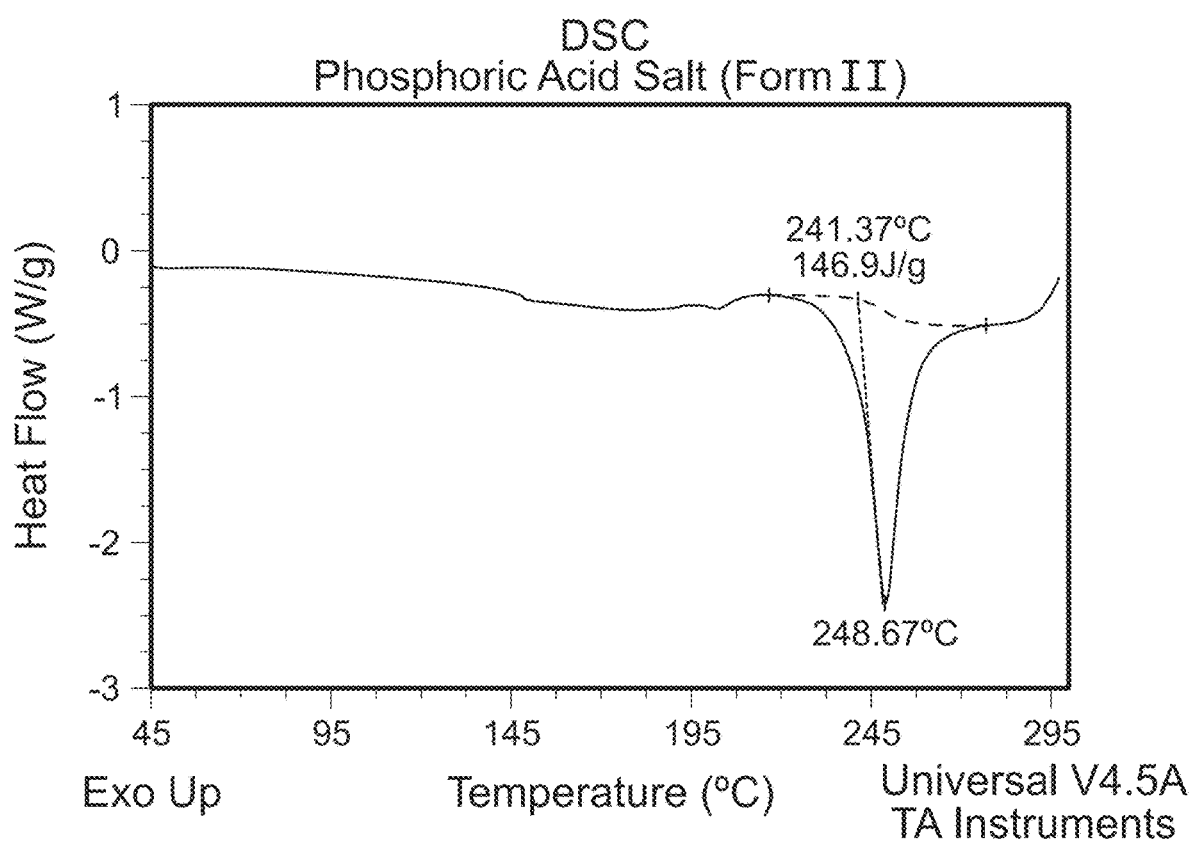
FIG. 8 shows the DSC thermogram of Compound 1 phosphoric acid salt Form II.
Figure 9:
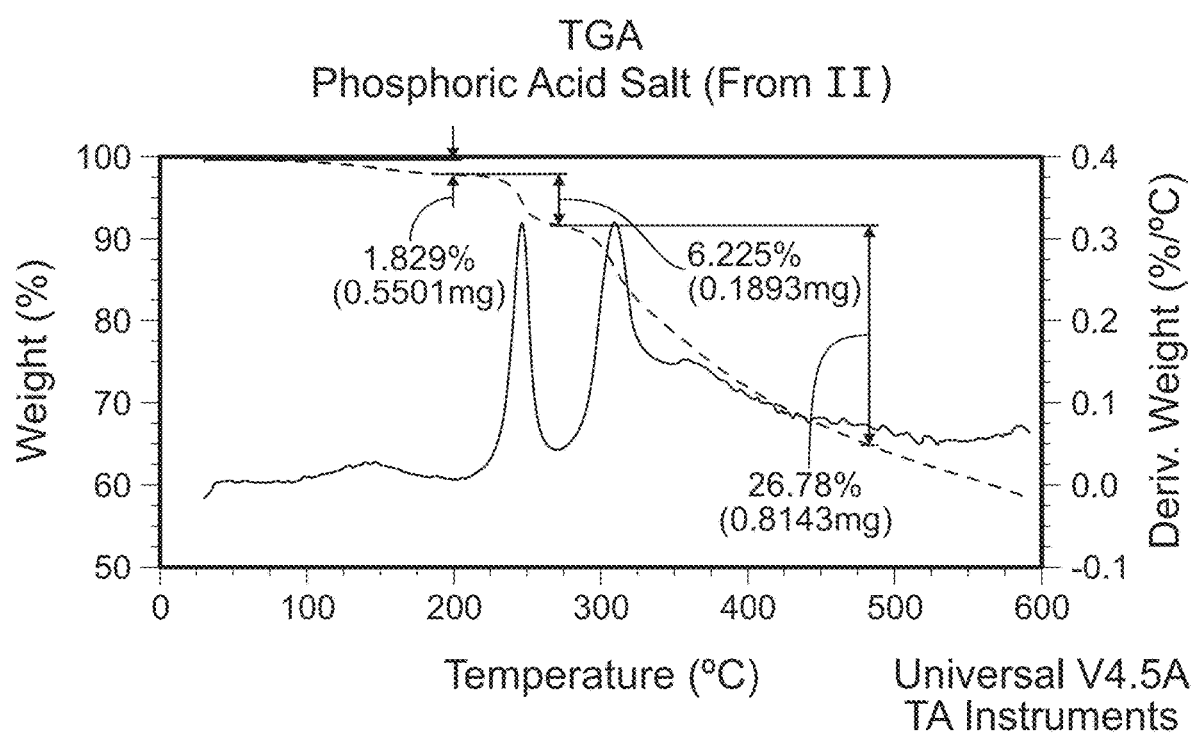
FIG. 9 shows the TGA thermogram of Compound 1 phosphoric acid salt Form II.

In some embodiments, Compound 1 phosphoric acid salt is a crystalline solid having Form II. In some embodiments, the crystalline solid having Form II has at least one characteristic XRPD peak, in terms of 2-theta, selected from about 4.7, about 9.4, about 18.8, about 21.7, about 24.8, and about 33.3 degrees. In some embodiments, the crystalline solid having Form II has at least 2 characteristic XRPD peaks, in terms of 2-theta, selected from about 4.7, about 9.4, about 18.8, about 21.7, about 24.8, and about 33.3 degrees. In some embodiments, the crystalline solid having Form II has at least 3 characteristic XRPD peaks, in terms of 2-theta, selected from about 4.7, about 9.4, about 18.8, about 21.7, about 24.8, and about 33.3 degrees. In some embodiments, the crystalline solid having Form II has at least one characteristic XRPD peak, in terms of 2-theta, selected from about 4.7, about 9.4, about 18.8 degrees. In some embodiments, the crystalline solid having Form II has at least two characteristic XRPD peaks, in terms of 2-theta, selected from about 4.7, about 9.4, about 18.8 degrees. In some embodiments, the crystalline solid having Form II has an XRPD pattern as depicted in FIG. 7. In some embodiments, the crystalline solid having Form II has a melting point of about 249° C. In some embodiments, the crystalline solid having Form II has an endothermic event at about 249° C. In some embodiments, the crystalline solid having Form II has a DSC thermogram substantially as depicted in FIG. 8. In some embodiments, the crystalline solid having Form II has a TGA thermogram substantially as depicted in FIG. 9.

Figure 10:
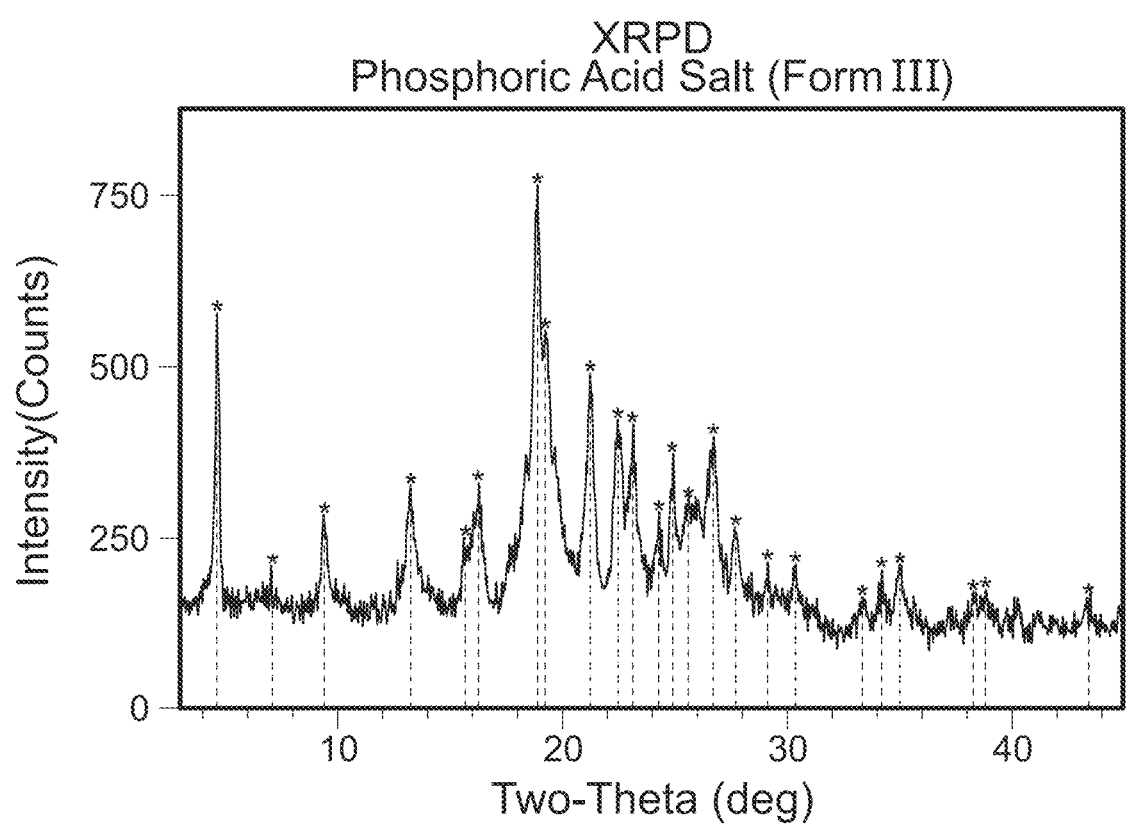
FIG. 10 shows the XRPD pattern of Compound 1 phosphoric acid salt Form III.
Figure 11:
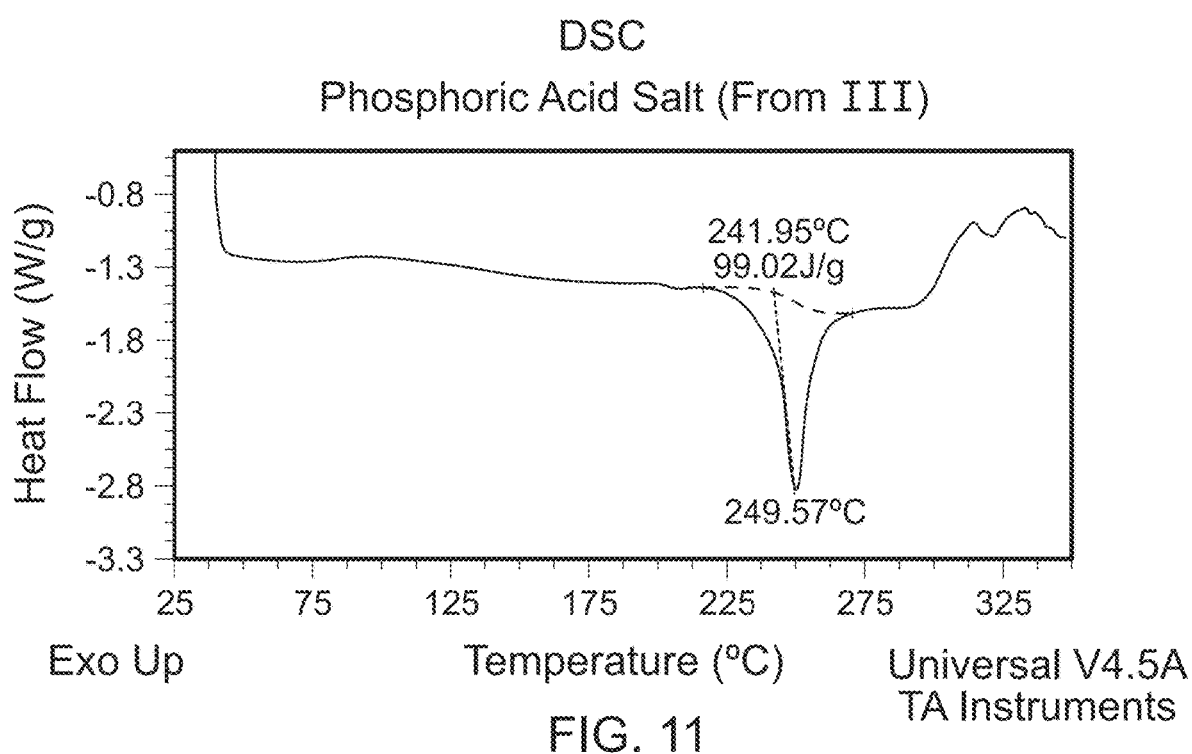
FIG. 11 shows the DSC thermogram of Compound 1 phosphoric acid salt Form III.
Figure 12:
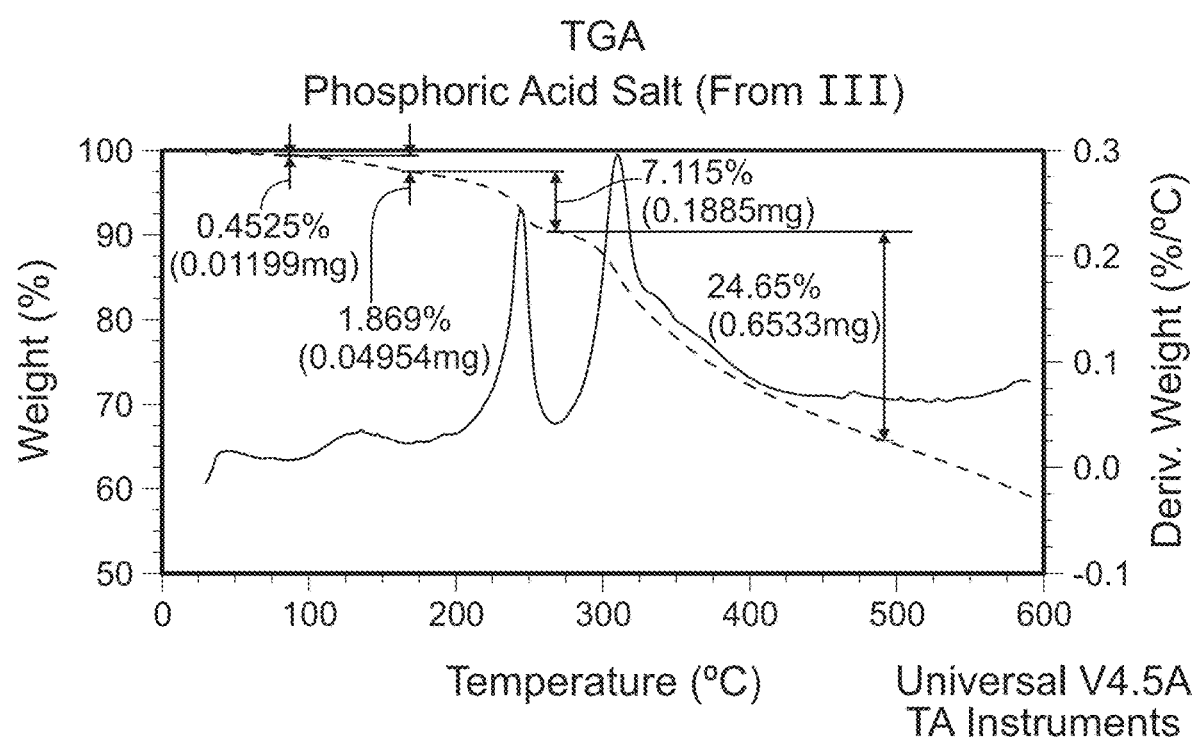
FIG. 12 shows the TGA thermogram of Compound 1 phosphoric acid salt Form III.

In some embodiments, Compound 1 phosphoric acid salt is a crystalline solid having Form III. In some embodiments, the crystalline solid having Form III has at least one characteristic XRPD peak, in terms of 2-theta, selected from about 4.6, about 9.4, about 13.3, about 16.3, about 18.9, about 19.2, about 21.2, about 22.5, about 23.1, about 24.9, and about 26.7 degrees. In some embodiments, the crystalline solid having Form III has at least two characteristic XRPD peaks, in terms of 2-theta, selected from about 4.6, about 9.4, about 13.3, about 16.3, about 18.9, about 19.2, about 21.2, about 22.5, about 23.1, about 24.9, and about 26.7 degrees. In some embodiments, the crystalline solid having Form III has at least three characteristic XRPD peaks, in terms of 2-theta, selected from about 4.6, about 9.4, about 13.3, about 16.3, about 18.9, about 19.2, about 21.2, about 22.5, about 23.1, about 24.9, and about 26.7 degrees. In some embodiments, the crystalline solid having Form III has at least one characteristic XRPD peak, in terms of 2-theta, selected from about 4.6, about 18.9, about 19.2, about 22.5, and about 23.1 degrees. In some embodiments, the crystalline solid having Form III has at least two characteristic XRPD peaks, in terms of 2-theta, selected from about 4.6, about 18.9, about 19.2, about 22.5, and about 23.1 degrees. In some embodiments, the crystalline solid having Form III has at least three characteristic XRPD peaks, in terms of 2-theta, selected from about 4.6, about 18.9, about 19.2, about 22.5, and about 23.1 degrees. In some embodiments, the crystalline solid having Form III has an XRPD pattern as depicted in FIG. 10. In some embodiments, the crystalline solid having Form III has a melting point of about 250° C. In some embodiments, the crystalline solid having Form III has an endothermic event at about 250° C. In some embodiments, the crystalline solid having Form III has a DSC thermogram substantially as depicted in FIG. 11. In some embodiments, the crystalline solid having Form III has a TGA thermogram substantially as depicted in FIG. 12.

Figure 13:
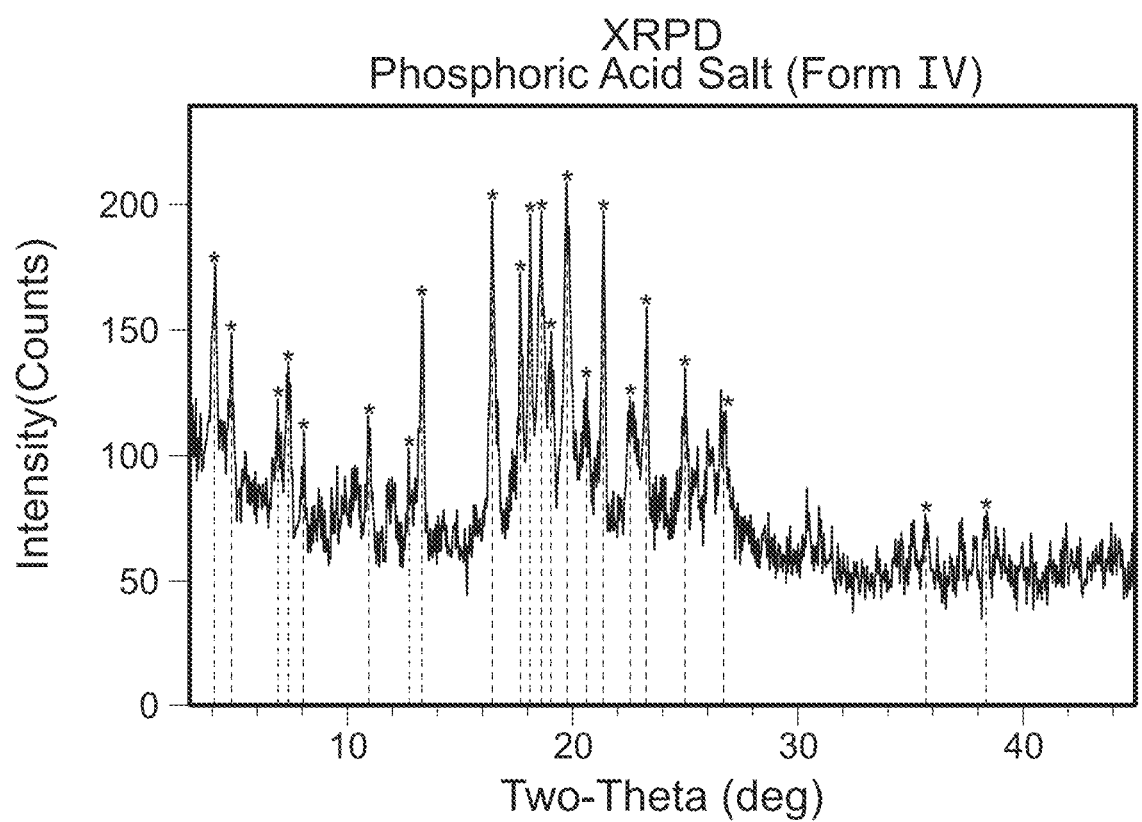
FIG. 13 shows the XRPD pattern of Compound 1 phosphoric acid salt Form IV.
Figure 14:
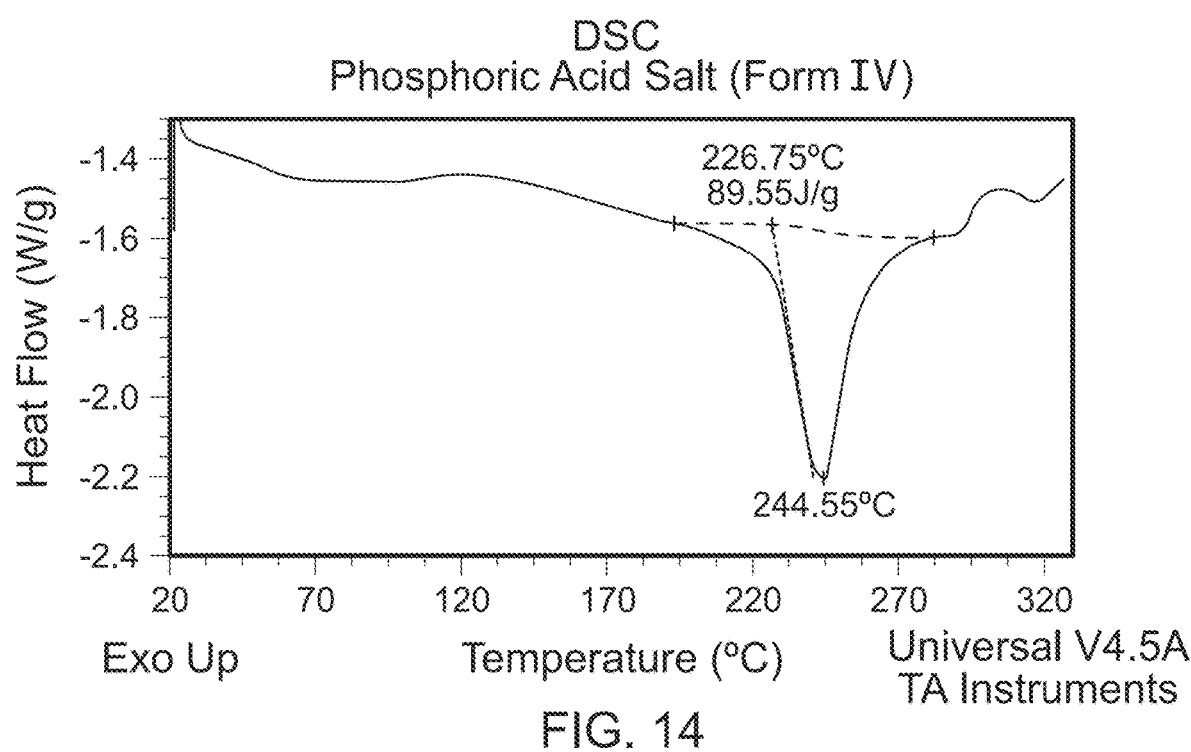
FIG. 14 shows the DSC thermogram of Compound 1 phosphoric acid salt Form IV.
Figure 15:
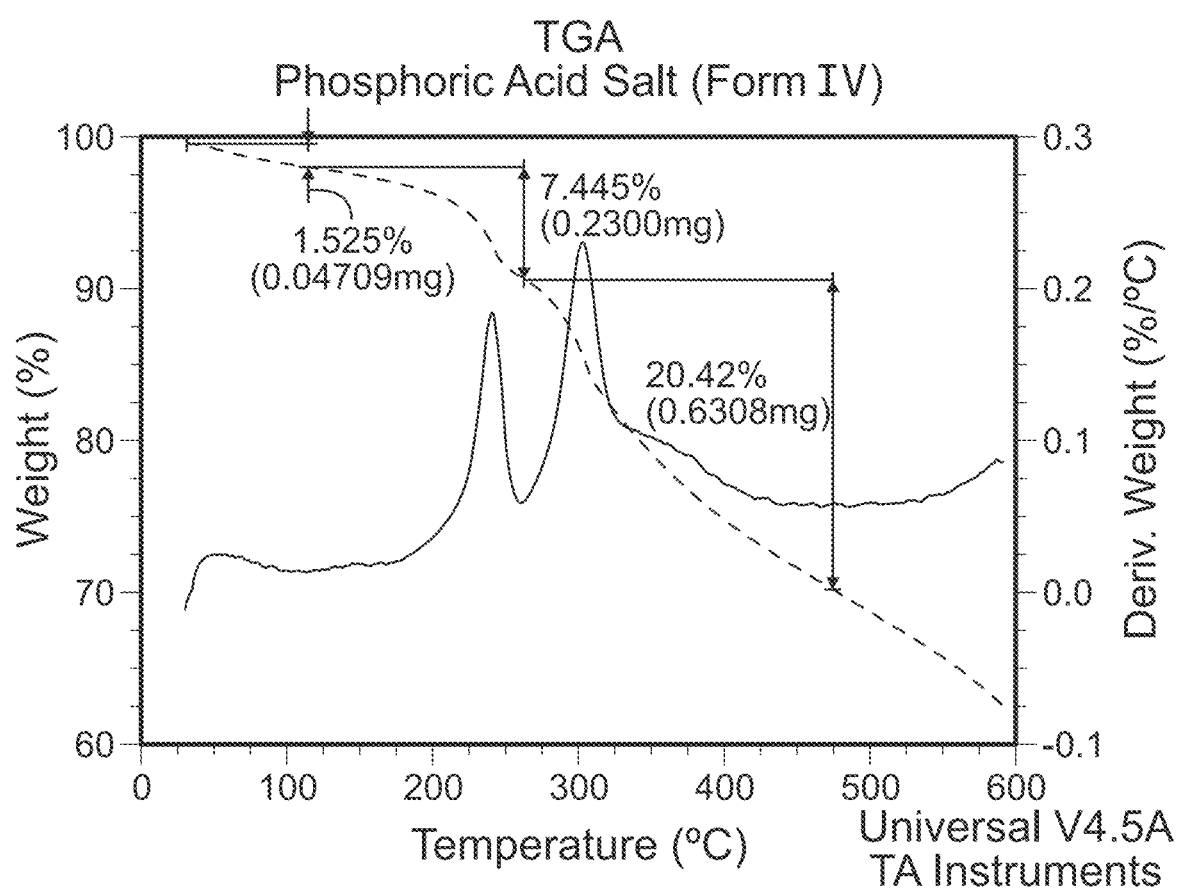
FIG. 15 shows the TGA thermogram of Compound 1 phosphoric acid salt Form IV.

In some embodiments, Compound 1 phosphoric acid salt is a crystalline solid having Form IV. In some embodiments, the crystalline solid having Form IV has at least one characteristic XRPD peak, in terms of 2-theta, selected from about 4.1, about 13.3, about 16.4, about 17.7, about 18.6, about 19.8, about 21.4, and about 23.3 degrees. In some embodiments, the crystalline solid having Form IV has at least two characteristic XRPD peaks, in terms of 2-theta, selected from about 4.1, about 13.3, about 16.4, about 17.7, about 18.6, about 19.8, about 21.4, and about 23.3 degrees. In some embodiments, the crystalline solid having Form IV has at least three characteristic XRPD peaks, in terms of 2-theta, selected from about 4.1, about 13.3, about 16.4, about 17.7, about 18.6, about 19.8, about 21.4, and about 23.3 degrees. In some embodiments, the crystalline solid having Form IV has at least one characteristic XRPD peak, in terms of 2-theta, selected from about 4.1, about 13.3, about 16.4, about 18.6, about 19.8, and about 21.4 degrees. In some embodiments, the crystalline solid having Form IV has at least two characteristic XRPD peaks, in terms of 2-theta, selected from about 4.1, about 13.3, about 16.4, about 18.6, about 19.8, and about 21.4 degrees. In some embodiments, the crystalline solid having Form IV has at least three characteristic XRPD peaks, in terms of 2-theta, selected from about 4.1, about 13.3, about 16.4, about 18.6, about 19.8, and about 21.4 degrees. In some embodiments, the crystalline solid having Form IV has an XRPD pattern as depicted in FIG. 13. In some embodiments, the crystalline solid having Form IV has a melting point of about 245° C. In some embodiments, the crystalline solid having Form IV has a melting point of about 245° C. In some embodiments, the crystalline solid having Form IV has a DSC thermogram substantially as depicted in FIG. 14. In some embodiments, the crystalline solid having Form IV has a TGA thermogram substantially as depicted in FIG. 15.

Figure 16:
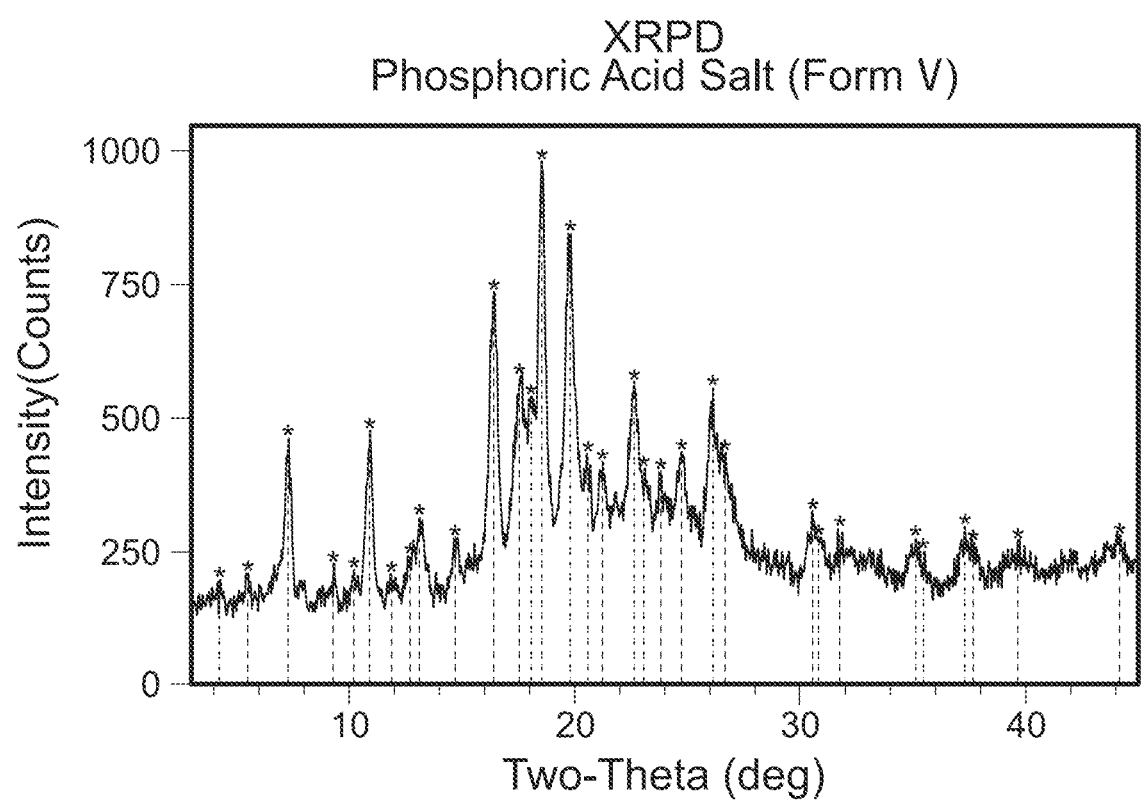
FIG. 16 shows the XRPD pattern of Compound 1 phosphoric acid salt Form V.
Figure 17:
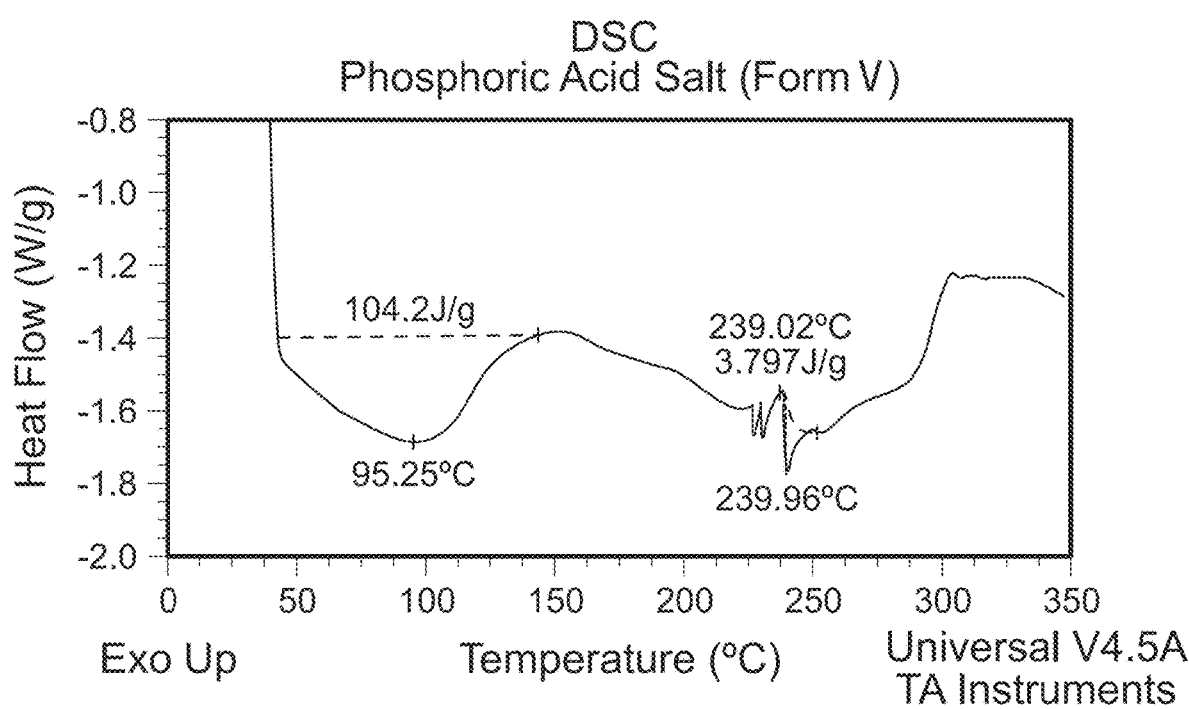
FIG. 17 shows the DSC thermogram of Compound 1 phosphoric acid salt Form V.
Figure 18:
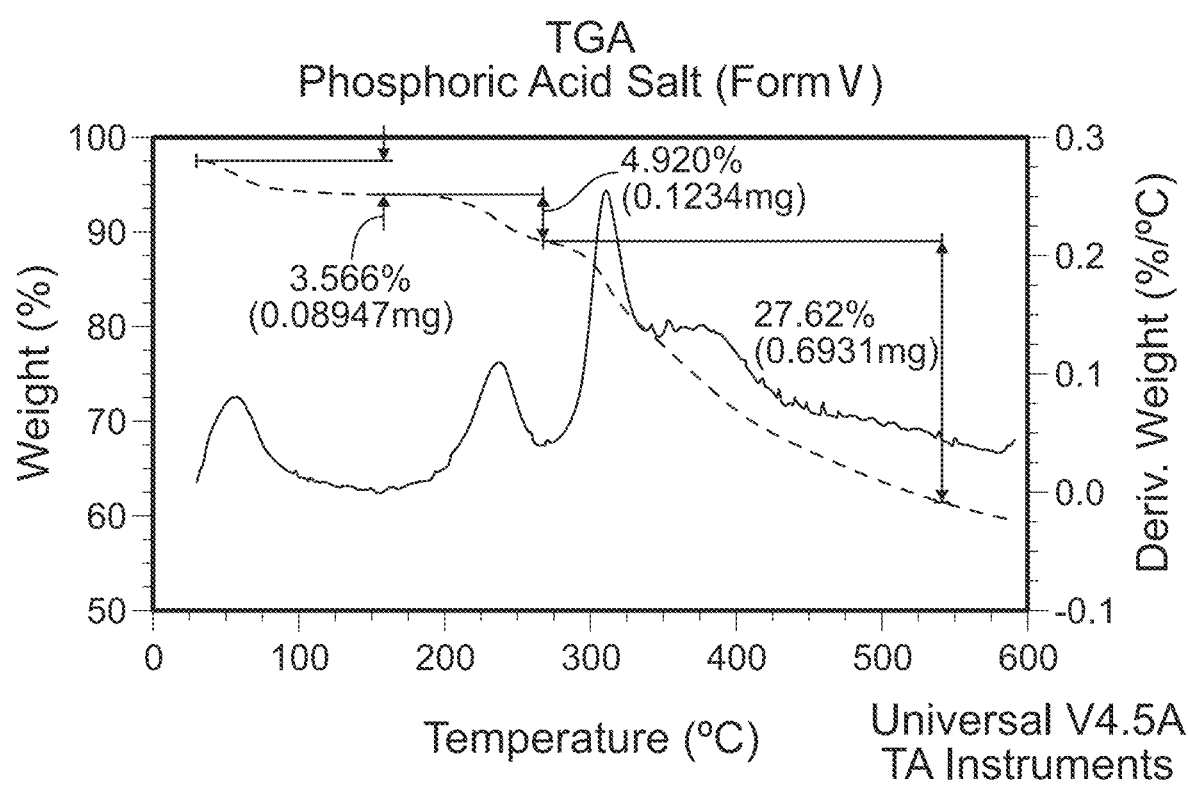
FIG. 18 shows the TGA thermogram of Compound 1 phosphoric acid salt Form V.

In some embodiments, Compound 1 phosphoric acid salt is a crystalline solid having Form V. In some embodiments, the crystalline solid having Form V has at least one characteristic XRPD peak, in terms of 2-theta, selected from about 7.3, about 10.9, about 16.4, about 18.5, about 19.8, about 22.6, and about 26.1 degrees. In some embodiments, the crystalline solid having Form V has at least two characteristic XRPD peaks, in terms of 2-theta, selected from about 7.3, about 10.9, about 16.4, about 18.5, about 19.8, about 22.6, and about 26.1 degrees. In some embodiments, the crystalline solid having Form V has at least three characteristic XRPD peaks, in terms of 2-theta, selected from about 7.3, about 10.9, about 16.4, about 18.5, about 19.8, about 22.6, and about 26.1 degrees. In some embodiments, the crystalline solid having Form V has at least one characteristic XRPD peak, in terms of 2-theta, selected from about 7.3, about 10.9, about 16.4, about 18.5, and about 19.8 degrees. In some embodiments, the crystalline solid having Form V has at least two characteristic XRPD peaks, in terms of 2-theta, selected from about 7.3, about 10.9, about 16.4, about 18.5, and about 19.8 degrees. In some embodiments, the crystalline solid having Form V has at least three characteristic XRPD peaks, in terms of 2-theta, selected from about 7.3, about 10.9, about 16.4, about 18.5, and about 19.8 degrees. In some embodiments, the crystalline solid having Form V has an XRPD pattern as shown on FIG. 16. In some embodiments, the crystalline solid having Form V has an endothermic event at about 95° C. or about 245° C. In some embodiments, the crystalline solid having Form V has a DSC thermogram substantially as depicted in FIG. 17. In some embodiments, the crystalline solid having Form V has a TGA thermogram substantially as depicted in FIG. 18.

Figure 19:
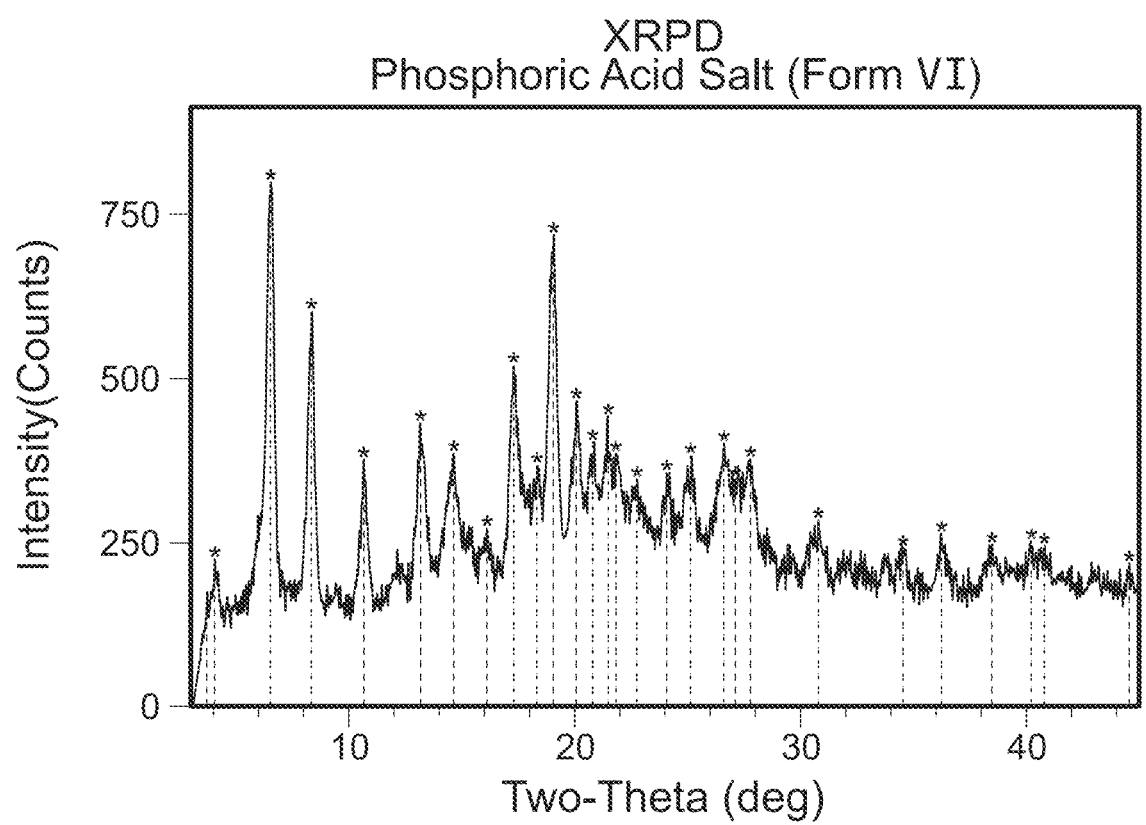
FIG. 19 shows the XRPD pattern of Compound 1 phosphoric acid salt Form VI.
Figure 20:
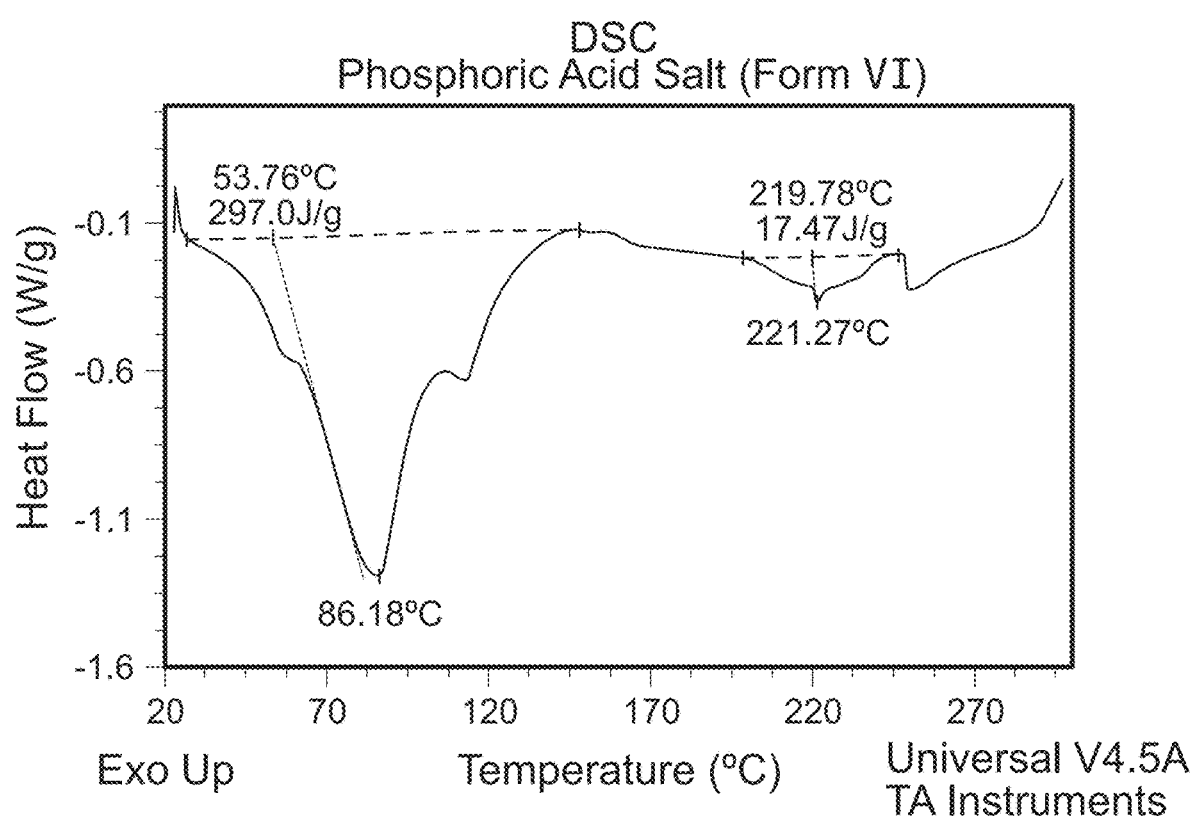
FIG. 20 shows the DSC thermogram of Compound 1 phosphoric acid salt Form VI.
Figure 21:
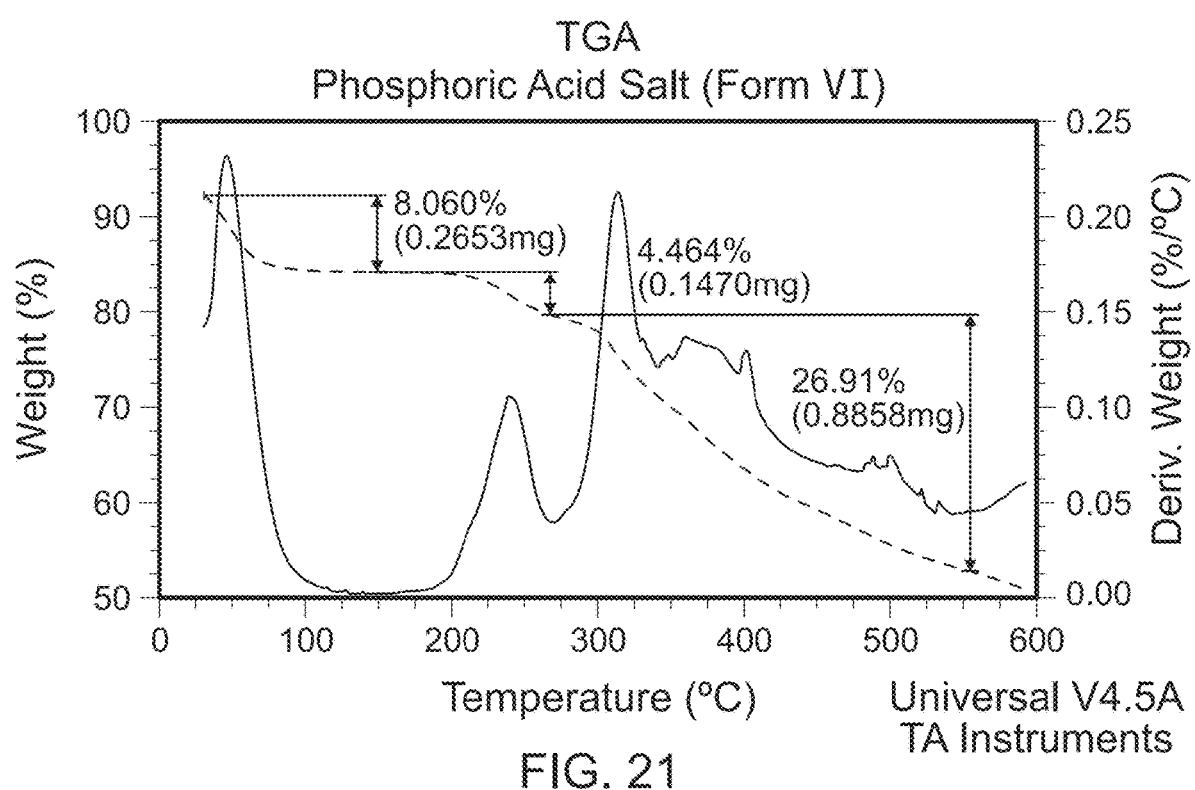
FIG. 21 shows the TGA thermogram of Compound 1 phosphoric acid salt Form VI.

In some embodiments, Compound 1 phosphoric acid salt is a crystalline solid having Form VI. In some embodiments, the crystalline solid having Form VI has at least one characteristic XRPD peak, in terms of 2-theta, selected from about 6.5, about 8.3, about 10.7, about 13.2, about 17.3, and about 19.1 degrees. In some embodiments, the crystalline solid having Form VI has at least two characteristic XRPD peaks, in terms of 2-theta, selected from about 6.5, about 8.3, about 10.7, about 13.2, about 17.3, and about 19.1 degrees. In some embodiments, the crystalline solid having Form VI has at least three characteristic XRPD peaks, in terms of 2-theta, selected from about 6.5, about 8.3, about 10.7, about 13.2, about 17.3, and about 19.1 degrees. In some embodiments, the crystalline solid having Form VI has at least one characteristic XRPD peak, in terms of 2-theta, selected from about 6.5, about 8.3, and about 10.7 degrees. In some embodiments, the crystalline solid having Form VI has at least two characteristic XRPD peaks, in terms of 2-theta, selected from about 6.5, about 8.3, and about 10.7 degrees. In some embodiments, the crystalline solid having Form VI has an XRPD pattern as shown on FIG. 19. In some embodiments, the crystalline solid having Form VI has a melting point of about 86° C. In some embodiments, the crystalline solid having Form VI has an endothermic event at about 86° C. or about 221° C. In some embodiments, the crystalline solid having Form VI has a DSC thermogram substantially as depicted in FIG. 20. In some embodiments, the crystalline solid having Form VI has a TGA thermogram substantially as depicted in FIG. 21.

In some embodiment, the present invention provides a mixture of crystalline solid Form I and one or more solid forms selected from amorphous, Form II, Form III, Form IV, and Form V.

In some embodiments, the mixture of the crystalline solid Form I has greater than about 50%, about 60%, about 70%, about 80%, about 90%, about 95%, about 98%, or about 99% of Form I.

In some embodiment, crystalline solid Form I is prepared in high purity. Purity values indicate the percentage of the amount of sample that is Form I. Purity values can be determined, for example, by HPLC/UV methods. In some embodiments, Form I has a purity greater than about 90%, greater than about 95%, greater than about 97%, greater than about 98%, or greater than about 99%. In some embodiments, Form I is substantially free of impurities, such as organic impurities, inorganic impurities, and/or residual solvents. Examples of organic impurities include e.g., starting materials and process intermediates such as

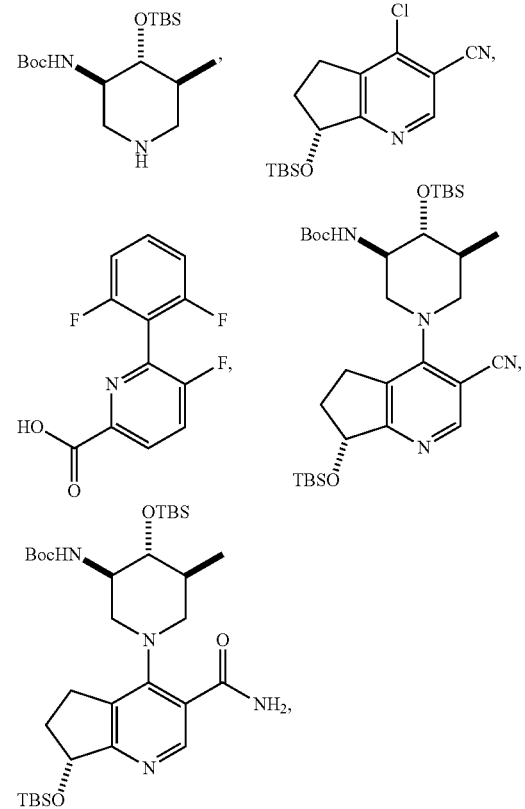

-continued

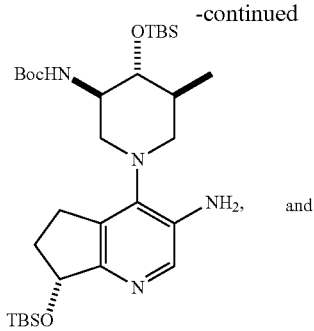

and

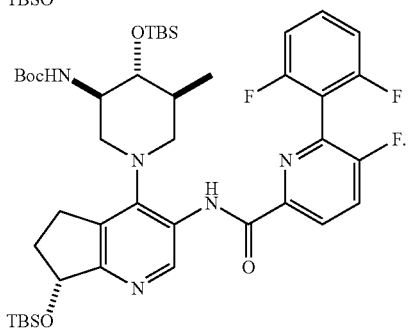

Examples of organic impurities include e.g., process impurities such as

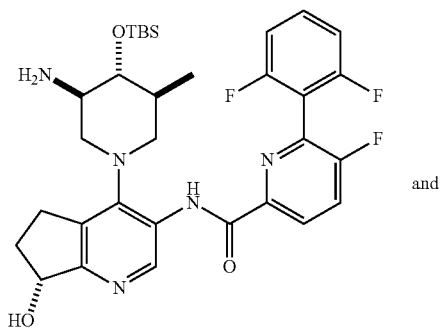

and

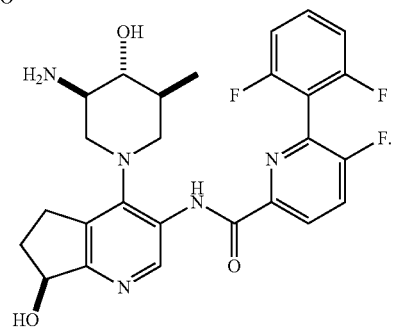

Examples of inorganic impurities include e.g., heavy metals, palladium, and ruthenium. Examples of residual solvents include e.g., acetonitrile, dichloromethane, N,N-dimethylformamide, 1,4-dioxane, n-heptane, methanol, and 2-propanol.

Hydrochloric Acid Salts

Figure 4:
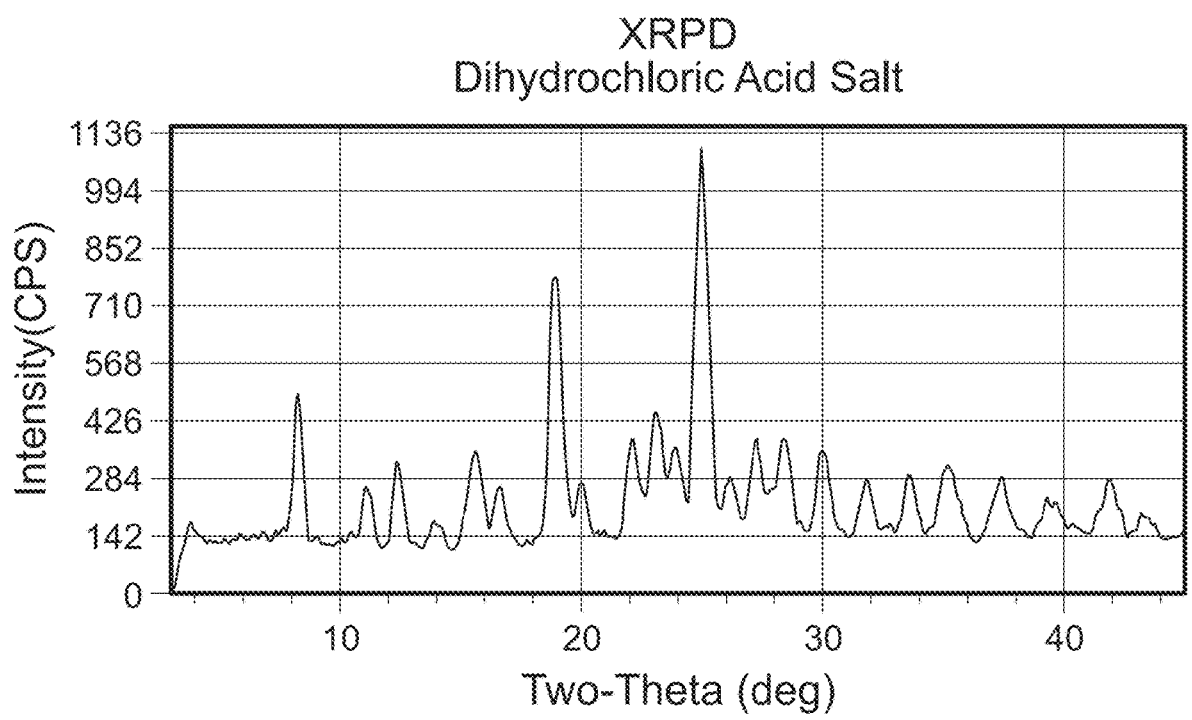
FIG. 4 shows the XRPD pattern of a solid form of Compound 1 dihydrochloric acid salt.
Figure 5:
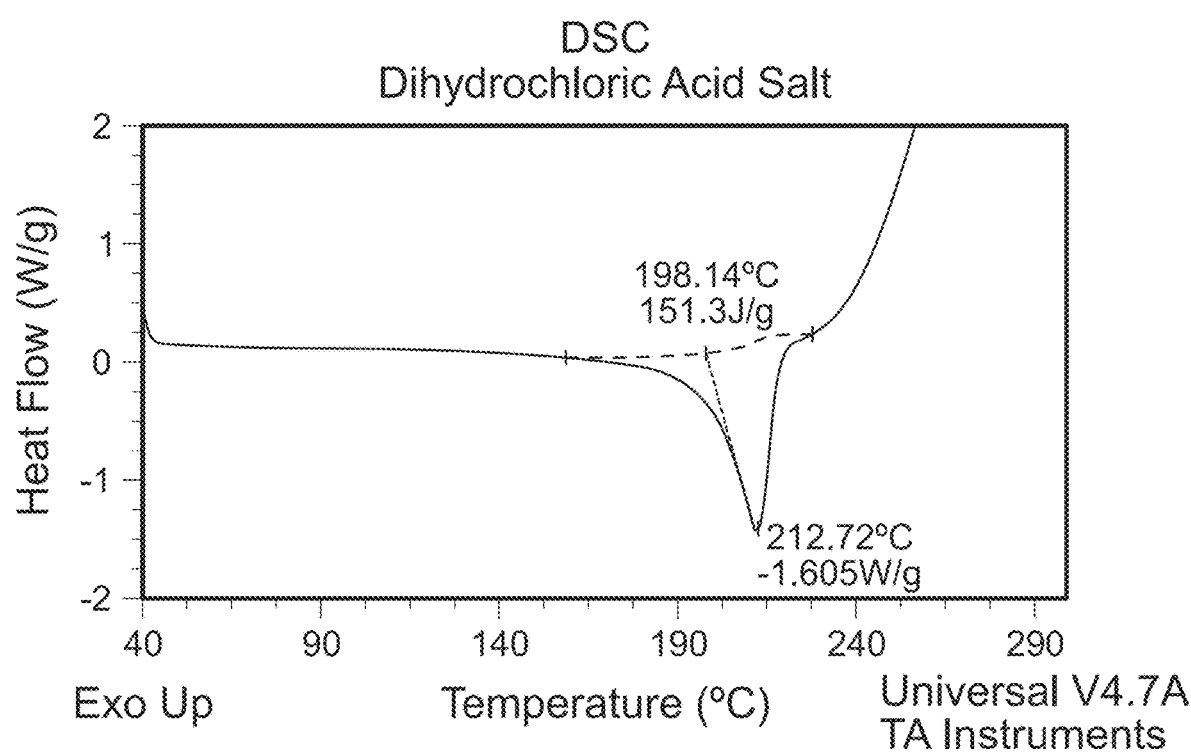
FIG. 5 shows the DSC thermogram of a solid form of Compound 1 dihydrochloric acid salt.
Figure 6:
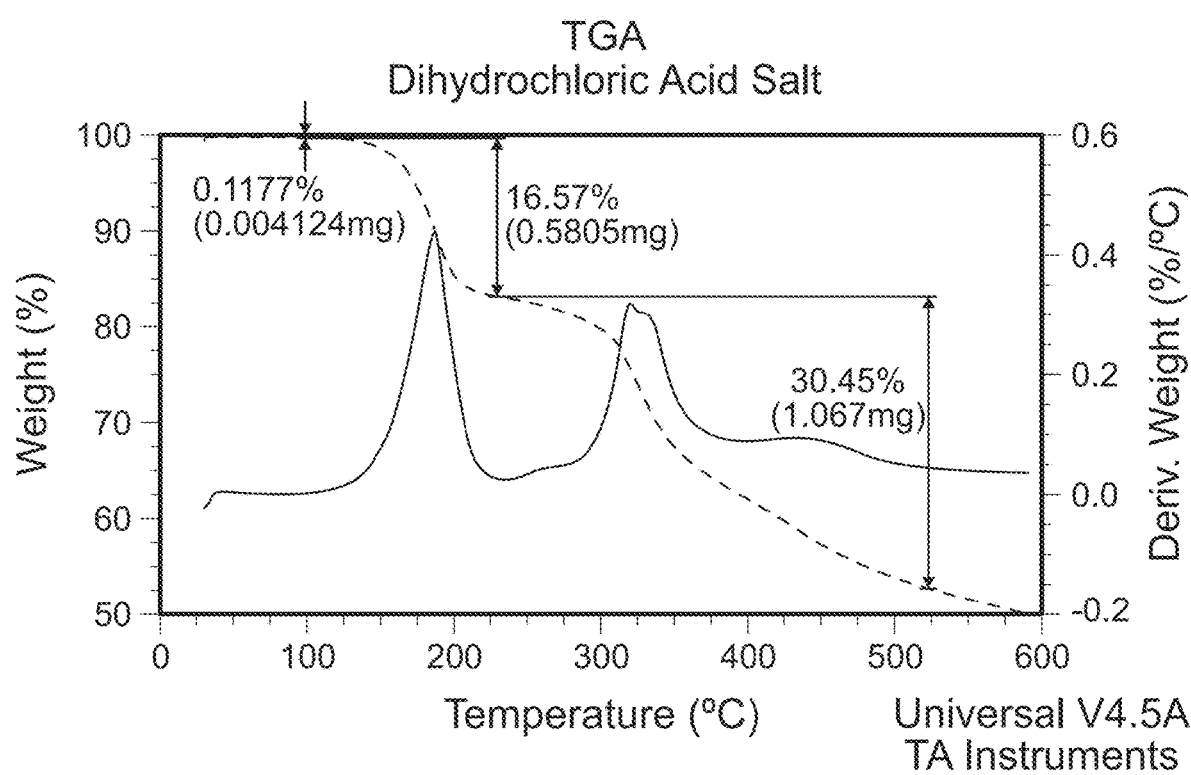
FIG. 6 shows the TGA thermogram of a solid form of Compound 1 dihydrochloric acid salt.

The present invention further provides the dihydrochloric acid salt of Compound 1. In some embodiments, a solid form of the dihydrochloric acid salt has an XRPD pattern as shown on FIG. 4. In some embodiments, a solid form of the dihydrochloric acid salt has a melting point of about 213° C. In some embodiments, a solid form of the dihydrochloric acid salt has an endothermic event at about 213° C. In some embodiments, a solid form of the dihydrochloric acid salt is characterized by a DSC thermogram substantially as depicted in FIG. 5. In some embodiments, a solid form of the dihydrochloric acid salt is characterized by a TGA thermogram substantially as depicted in FIG. 6.

In some embodiments, the dihydrochloric acid salt of Compound 1 is a crystalline solid. In some embodiments, the crystalline solid of Compound 1 dihydrochloric acid salt has at least one characteristic XRPD peak, in terms of 2-theta, selected from about 8.3, about 18.9, and about 25.0 degrees. In some embodiments, the crystalline solid of Compound 1 dihydrochloric acid salt has two or more characteristic XRPD peaks, in terms of 2-theta, selected from about 8.3, about 18.9, and about 25.0 degrees.

Figure 22:
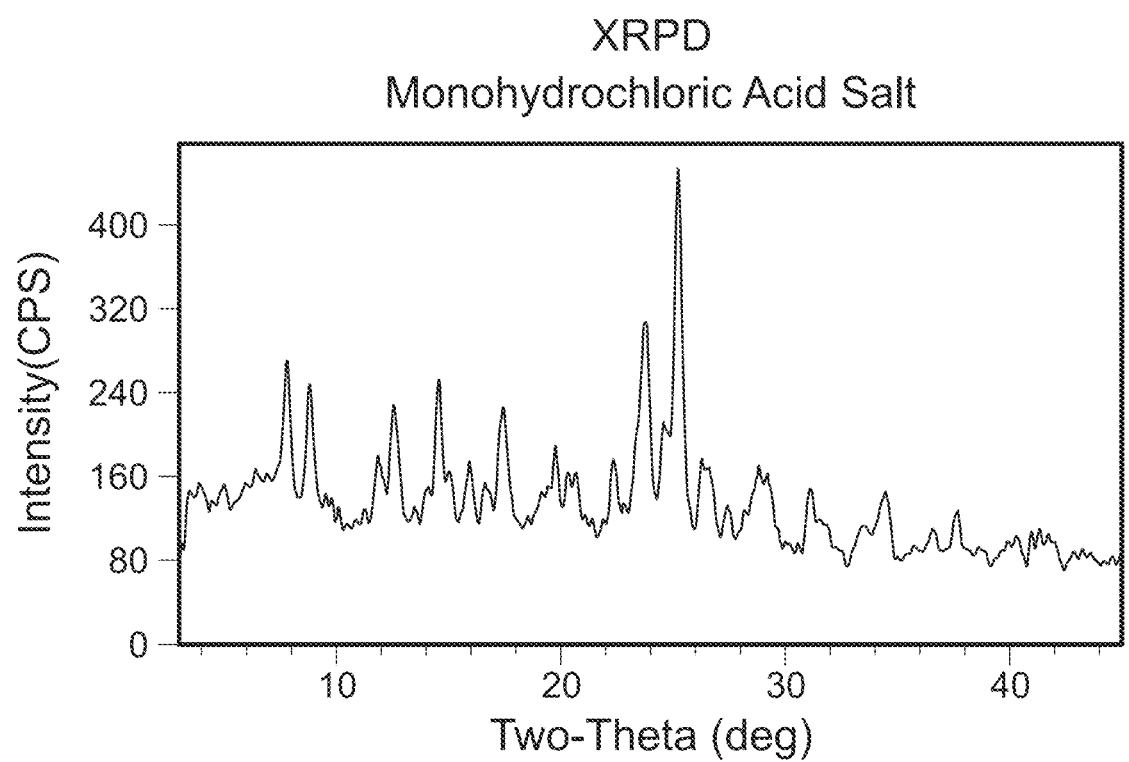
FIG. 22 shows the XRPD pattern of a solid form of Compound 1 mono-hydrochloric acid salt.
Figure 23:
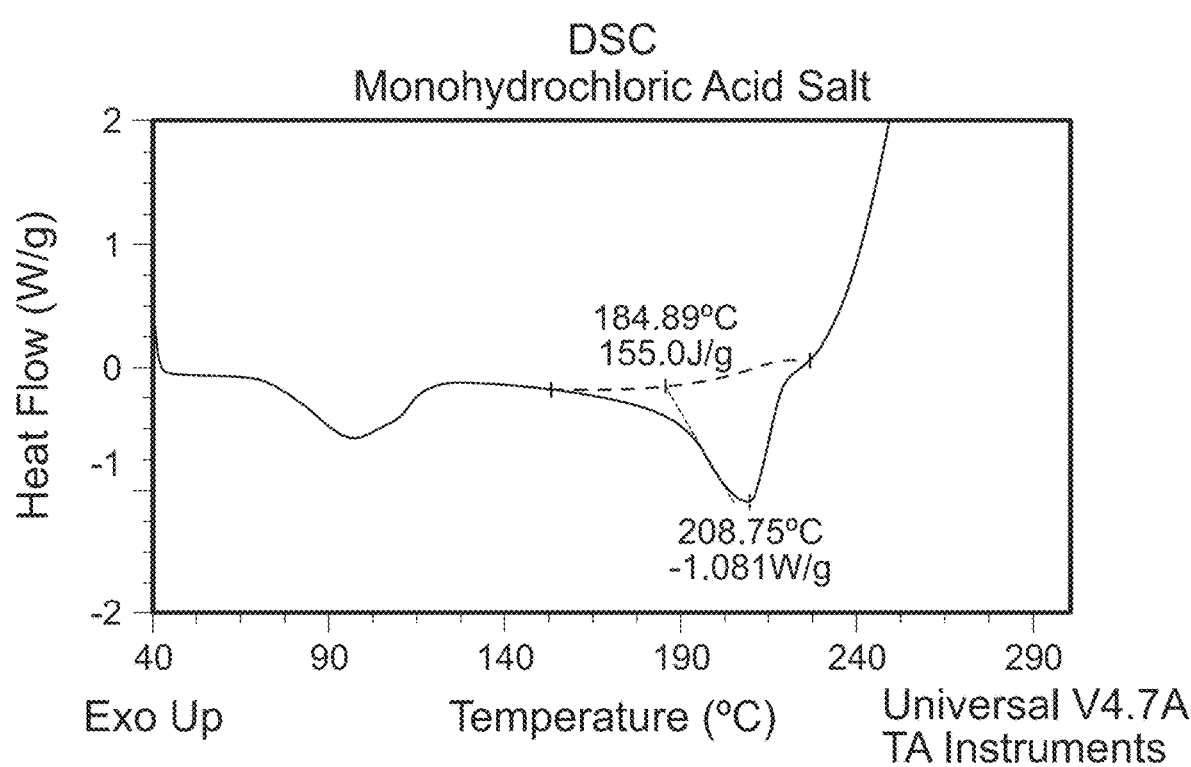
FIG. 23 shows the DSC thermogram of a solid form of Compound 1 mono-hydrochloric acid salt.

The present invention further provides the monohydrochloric acid salt of Compound 1. In some embodiments, a solid form of the monohydrochloric acid salt has an XRPD pattern as shown on FIG. 22. In some embodiments, a solid form of the monohydrochloric acid salt has a melting point of about 209° C. In some embodiments, a solid form of the monohydrochloric acid salt has an endothermic event at about 209° C. In some embodiments, a solid form of the monohydrochloric acid salt is characterized by a DSC thermogram substantially as depicted in FIG. 23.

In some embodiments, the monohydrochloric acid salt of Compound 1 is a crystalline solid. In some embodiments, the crystalline solid of Compound 1 monohydrochloric acid salt has at least one characteristic XRPD peak, in terms of 2-theta, selected from about 7.8, about 8.8, about 12.6, about 14.5, about 17.4, about 23.8, and about 25.2 degrees. In some embodiments, the crystalline solid of Compound 1 monohydrochloric acid salt has two or more characteristic XRPD peaks, in terms of 2-theta, selected from about 7.8, about 8.8, about 12.6, about 14.5, about 17.4, about 23.8, and about 25.2 degrees. In some embodiments, the crystalline solid of Compound 1 monohydrochloric acid salt has three or more characteristic XRPD peaks, in terms of 2-theta, selected from about 7.8, about 8.8, about 12.6, about 14.5, about 17.4, about 23.8, and about 25.2 degrees.

Maleic Acid Salt

Figure 24:
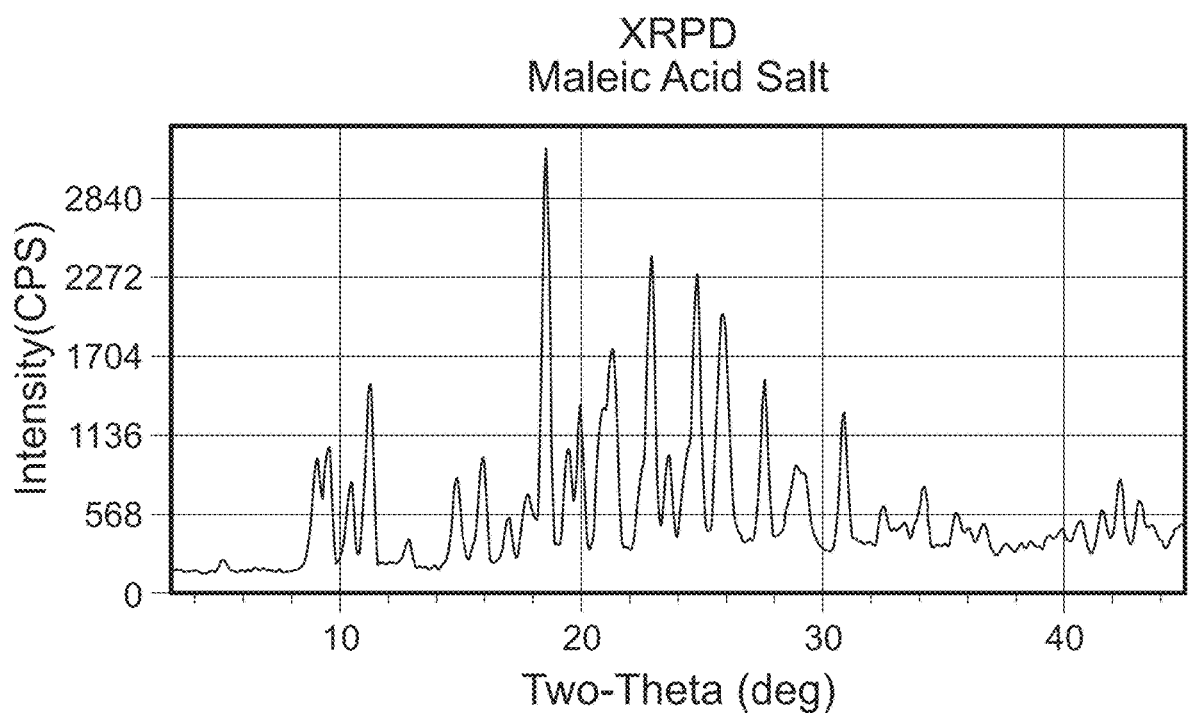
FIG. 24 shows the XRPD pattern of a solid form of Compound 1 maleic acid salt.
Figure 25:
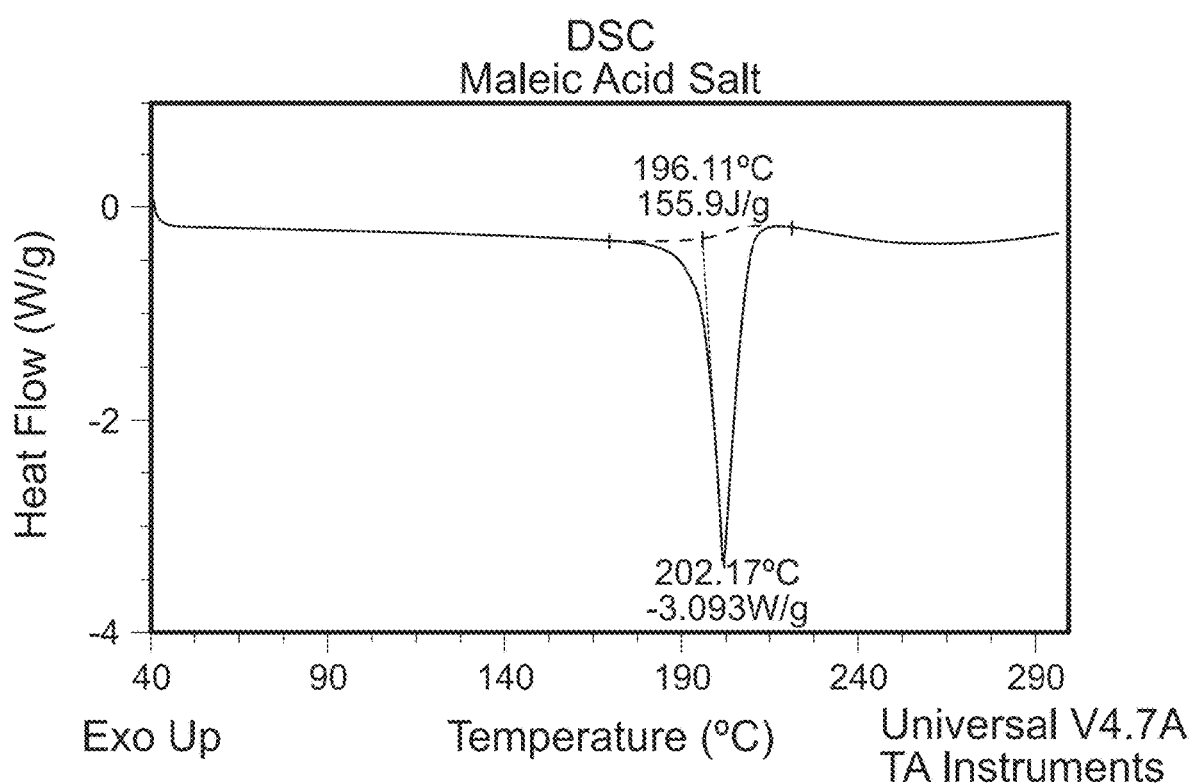
FIG. 25 shows the DSC thermogram of a solid form of Compound 1 maleic acid salt.
Figure 26:
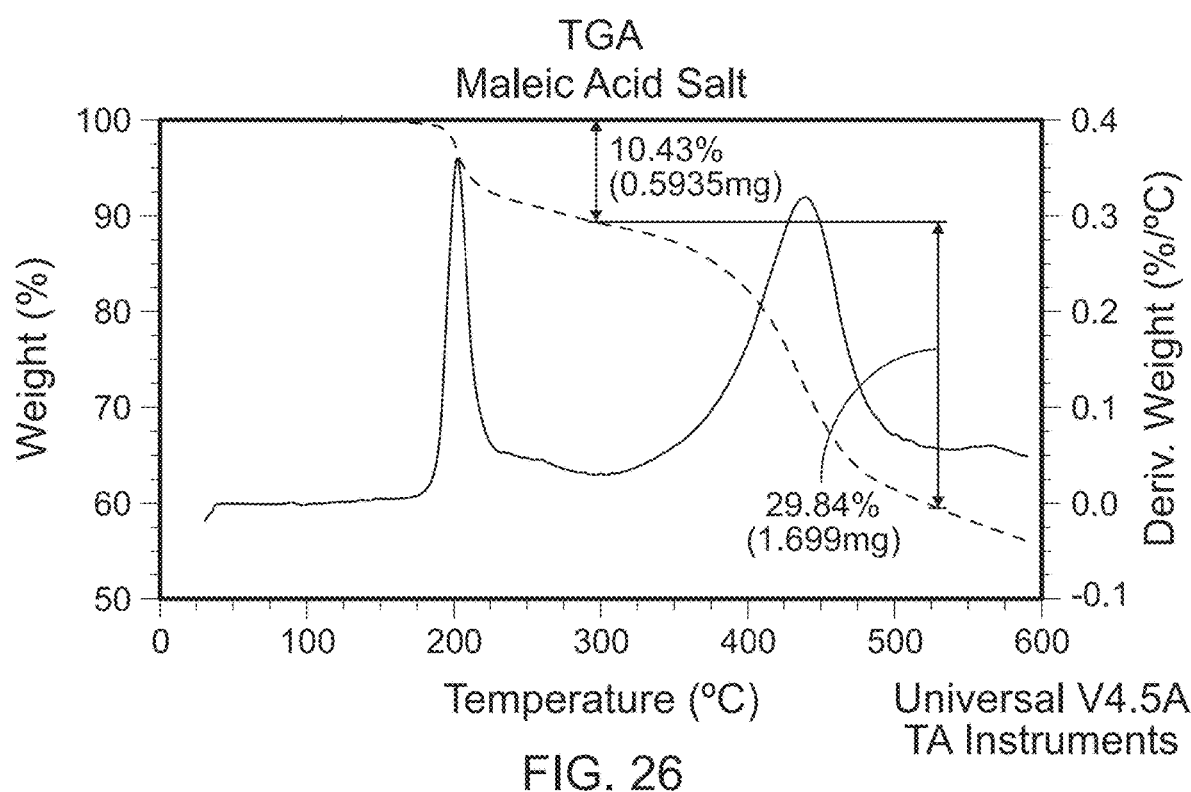
FIG. 26 shows the TGA thermogram of a solid form of Compound 1 maleic acid salt.

The present invention further provides a maleic acid salt of Compound 1. In some embodiments, a solid form of the maleic acid salt has an XRPD pattern as shown on FIG. 24. In some embodiments, a solid form of the maleic acid salt has a melting point of about 202° C. In some embodiments, a solid form of the maleic acid salt has an endothermic event at about 202° C. In some embodiments, a solid form of the maleic acid salt has a DSC thermogram substantially as depicted in FIG. 25. In some embodiments, the maleic acid salt has a TGA thermogram substantially as depicted in FIG. 26.

In some embodiments, the maleic acid salt of Compound 1 is a crystalline solid. In some embodiments, the crystalline solid of Compound 1 maleic acid salt has at least one characteristic XRPD peak, in terms of 2-theta, selected from about 9.0, about 9.5, about 11.2, about 14.8, about 15.9, about 18.5, about 19.5, about 19.9, about 21.3, about 22.9, about 24.8, about 25.8, about 27.6, and about 30.9 degrees. In some embodiments, the crystalline solid of Compound 1 maleic acid salt has at least two characteristic XRPD peaks, in terms of 2-theta, selected from about 9.0, about 9.5, about 11.2, about 14.8, about 15.9, about 18.5, about 19.5, about 19.9, about 21.3, about 22.9, about 24.8, about 25.8, about 27.6, and about 30.9 degrees. In some embodiments, the crystalline solid of Compound 1 maleic acid salt has at least three characteristic XRPD peaks, in terms of 2-theta, selected from about 9.0, about 9.5, about 11.2, about 14.8, about 15.9, about 18.5, about 19.5, about 19.9, about 21.3, about 22.9, about 24.8, about 25.8, about 27.6, and about 30.9 degrees.

Adipic Acid Salt

Figure 27:
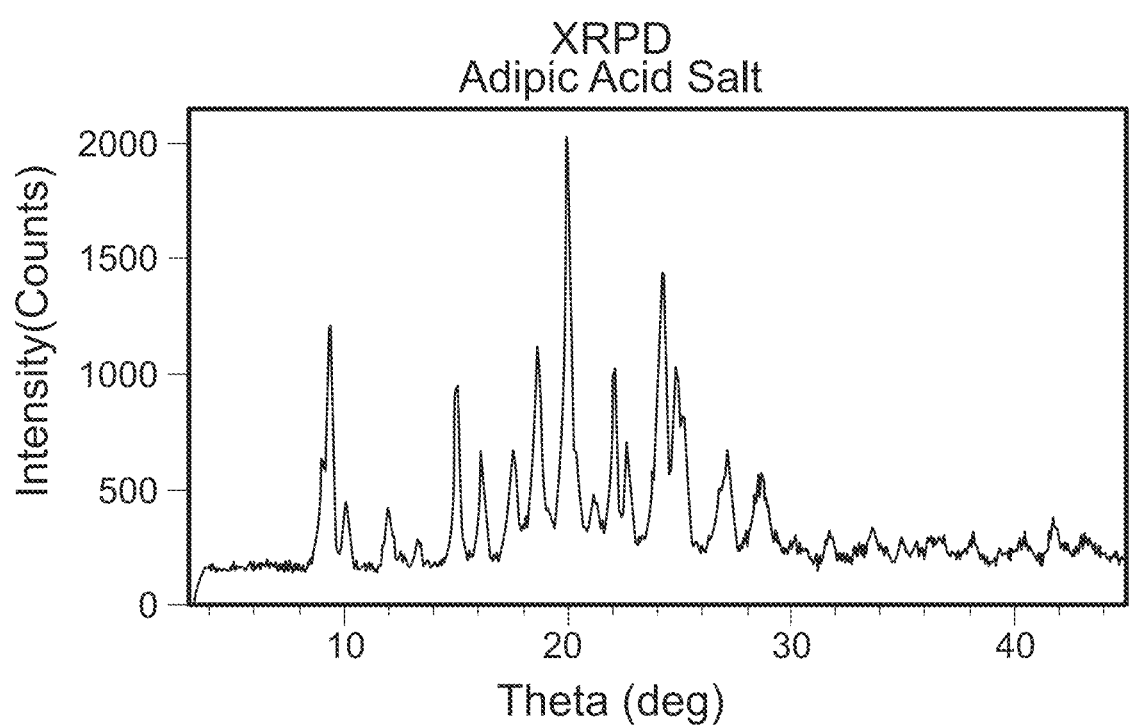
FIG. 27 shows the XRPD pattern of a solid form of Compound 1 adipic acid salt.
Figure 28:
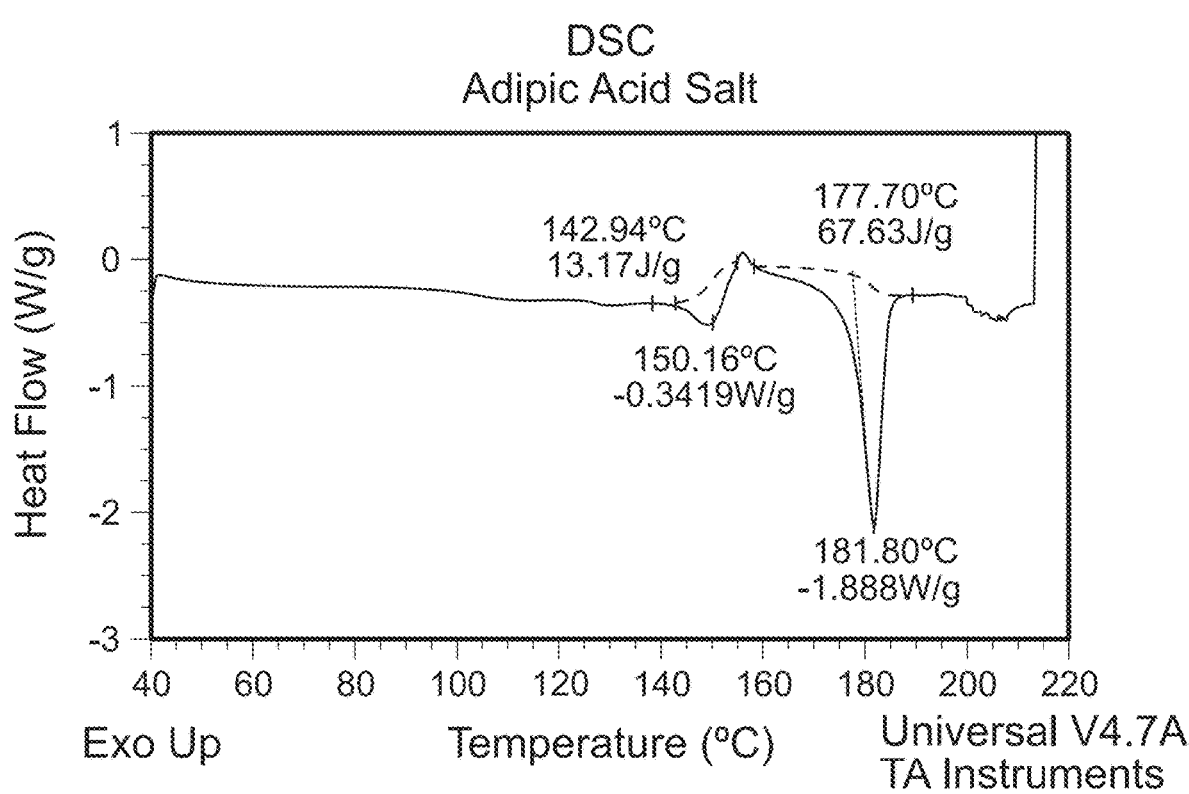
FIG. 28 shows the DSC thermogram of a solid form of Compound 1 adipic acid salt.
Figure 29:
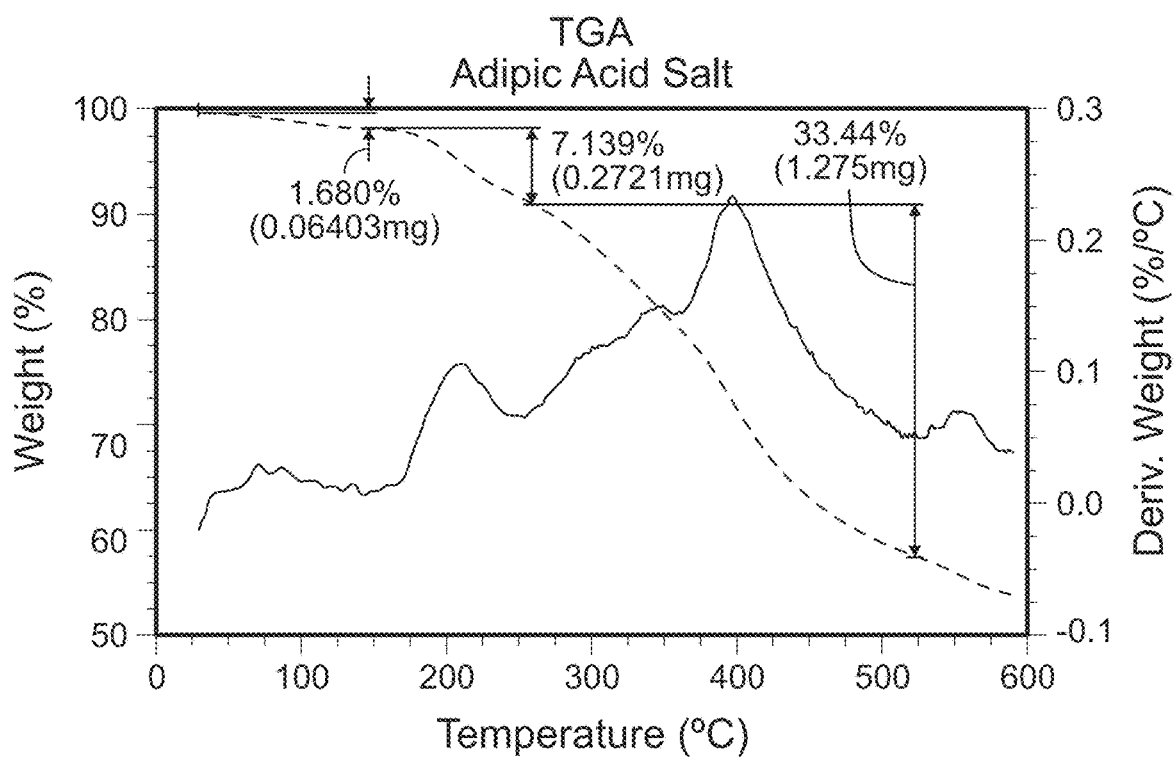
FIG. 29 shows the TGA thermogram of a solid form of Compound 1 adipic acid salt.

The present invention further provides an adipic acid salt of Compound 1. In some embodiments, a solid form of the adipic acid salt has an XRPD pattern as shown on FIG. 27. In some embodiments, a solid form of the adipic acid salt has a melting point of about 182° C. In some embodiments, a solid form of the adipic acid salt has an endothermic event at about 150° C. or about 182° C. In some embodiments, a solid form of the adipic acid salt has a DSC thermogram substantially as depicted in FIG. 28. In some embodiments, the adipic acid salt has a TGA thermogram substantially as depicted in FIG. 29.

In some embodiments, the adipic acid salt of Compound 1 is a crystalline solid. In some embodiments, the crystalline solid of Compound 1 adipic acid salt has at least one characteristic XRPD peak, in terms of 2-theta, selected from about 9.3, about 15.0, about 16.2, about 17.6, about 18.7, about 20.0, about 22.1, about 22.7, about 24.3, about 24.9, about 27.1, and about 28.7 degrees. In some embodiments, the crystalline solid of Compound 1 adipic acid salt has at least two characteristic XRPD peaks, in terms of 2-theta, selected from about 9.3, about 15.0, about 16.2, about 17.6, about 18.7, about 20.0, about 22.1, about 22.7, about 24.3, about 24.9, about 27.1, and about 28.7 degrees. In some embodiments, the crystalline solid of Compound 1 adipic acid salt has at least three characteristic XRPD peaks, in terms of 2-theta, selected from about 9.3, about 15.0, about 16.2, about 17.6, about 18.7, about 20.0, about 22.1, about 22.7, about 24.3, about 24.9, about 27.1, and about 28.7 degrees.

Hydrobromic Acid Salt

Figure 32:
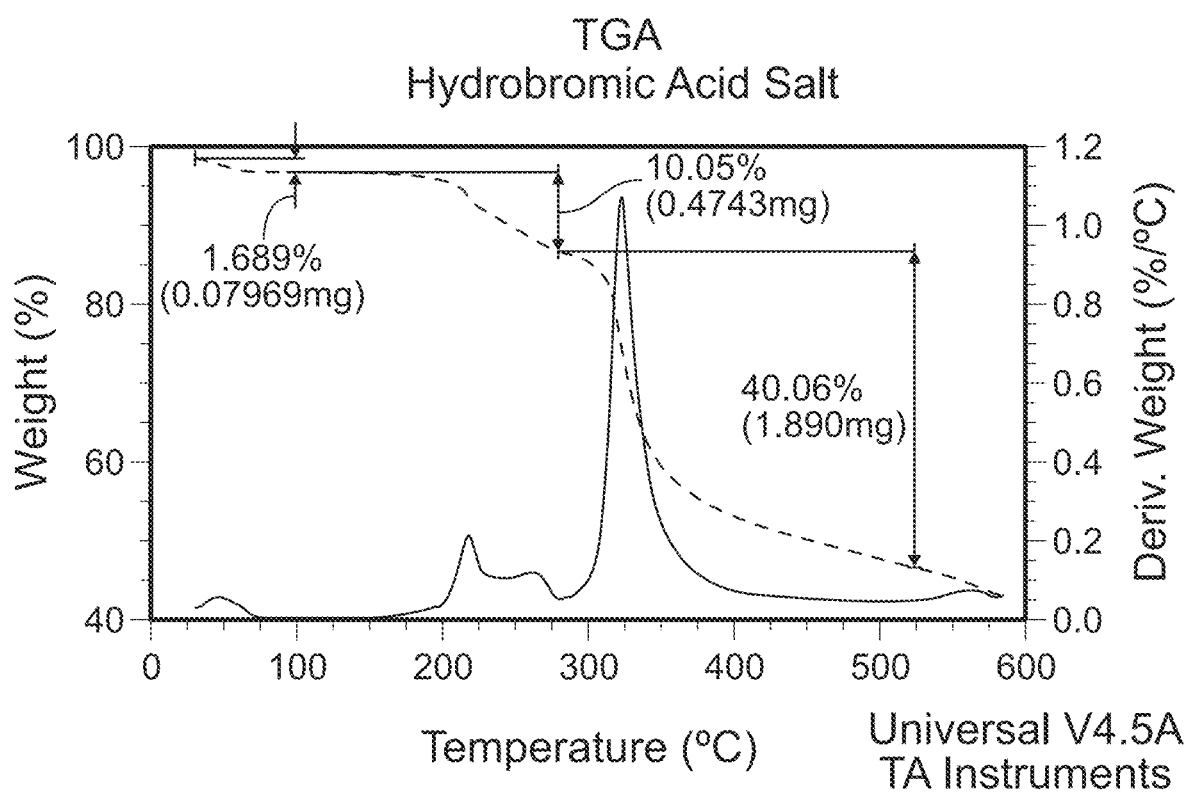
FIG. 32 shows the TGA thermogram of a solid form of Compound 1 hydrobromic acid salt.
Figure 33:
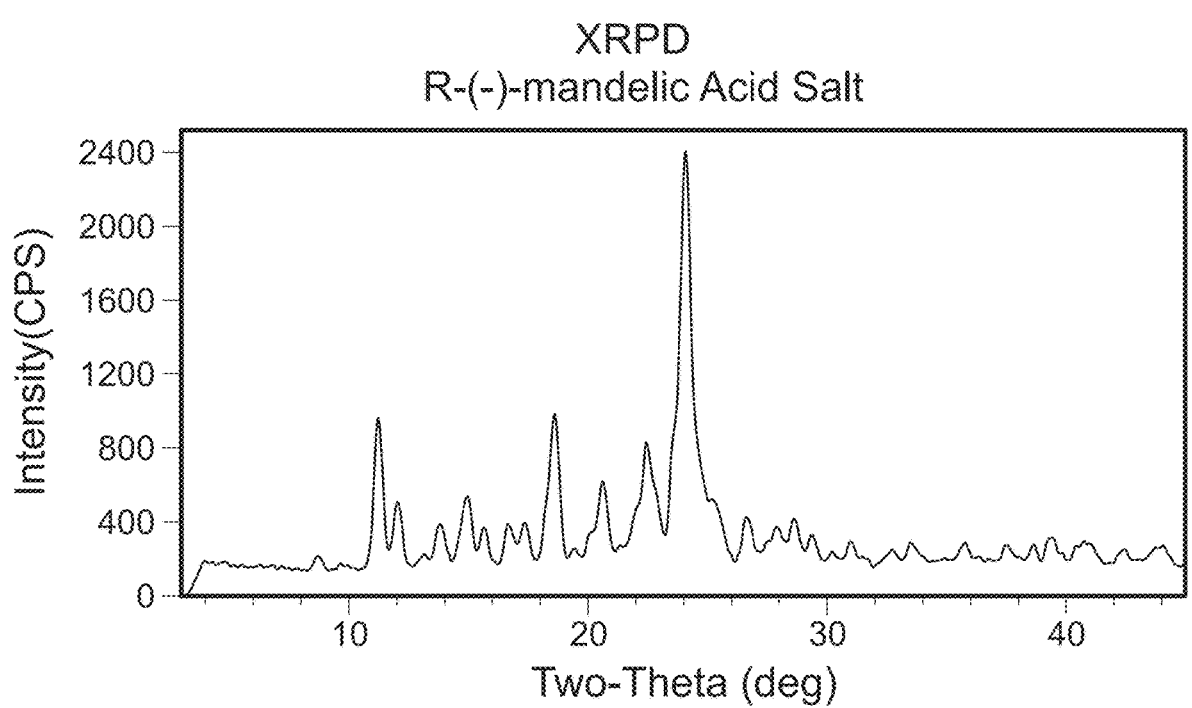
FIG. 33 shows the XRPD pattern of a solid form of Compound 1 R-(−)-mandelic acid salt.
Figure 34:
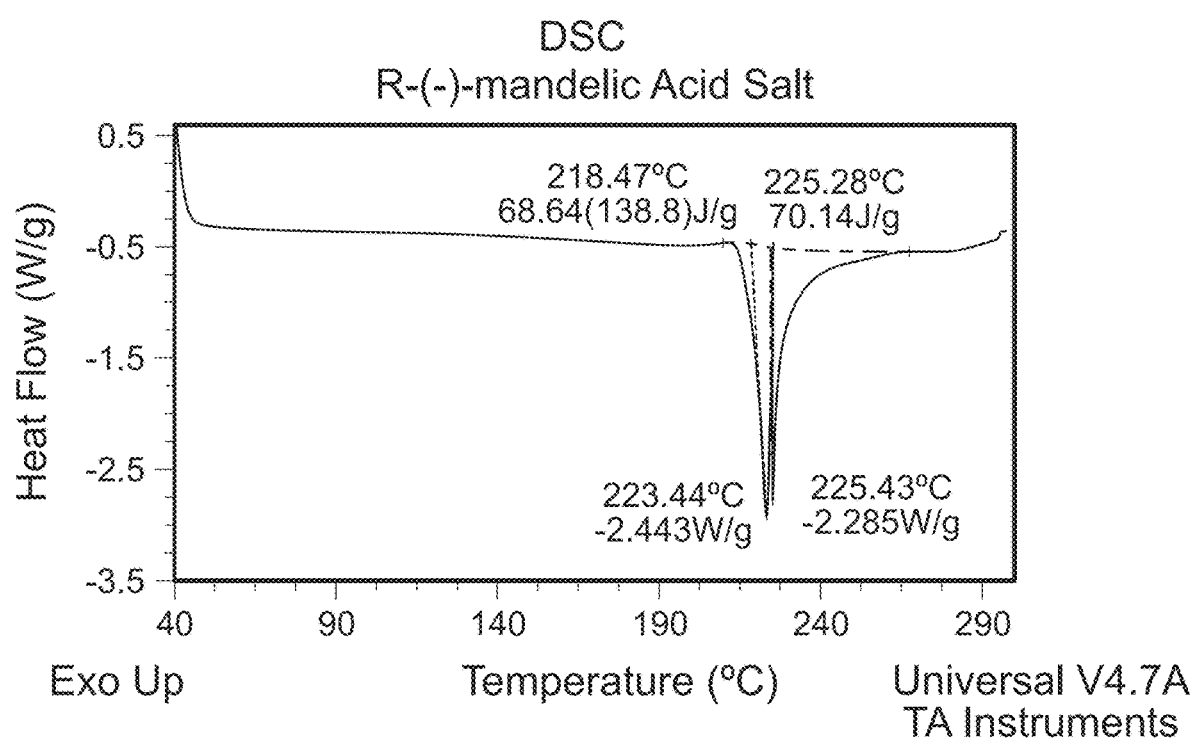
FIG. 34 shows the DSC thermogram of a solid form of Compound 1 R-(−)-mandelic acid salt.

The present invention further provides a hydrobromic acid salt of Compound 1. In some embodiments, a solid form of the hydrobromic acid salt has an XRPD pattern as shown on FIG. 32. In some embodiments, a solid form of the hydrobromic acid salt has a melting point of about 247° C. In some embodiments, a solid form of the hydrobromic acid salt has a DSC thermogram substantially as depicted in FIG. 33. In some embodiments, a solid form of the hydrobromic acid salt has a TGA thermogram substantially as depicted in FIG. 34.

In some embodiments, the hydrobromic acid salt of Compound 1 is a crystalline solid. In some embodiments, the crystalline solid of Compound 1 hydrobromic acid salt has at least one characteristic XRPD peak, in terms of 2-theta, selected from about 6.5, about 9.5, about 12.9, about 16.6, about 17.9, about 19.5, about 21.7, about 22.5, about 23.7, about 24.3, about 26.5, about 27.5, and about 28.3 degrees. In some embodiments, the crystalline solid of Compound 1 hydrobromic acid salt has at least two characteristic XRPD peaks, in terms of 2-theta, selected from about 6.5, about 9.5, about 12.9, about 16.6, about 17.9, about 19.5, about 21.7, about 22.5, about 23.7, about 24.3, about 26.5, about 27.5, and about 28.3 degrees. In some embodiments, the crystalline solid of Compound 1 hydrobromic acid salt has at least three characteristic XRPD peaks, in terms of 2-theta, selected from about 6.5, about 9.5, about 12.9, about 16.6, about 17.9, about 19.5, about 21.7, about 22.5, about 23.7, about 24.3, about 26.5, about 27.5, and about 28.3 degrees.

(R)-(−)-Mandelic Acid Salt

Figure 35:
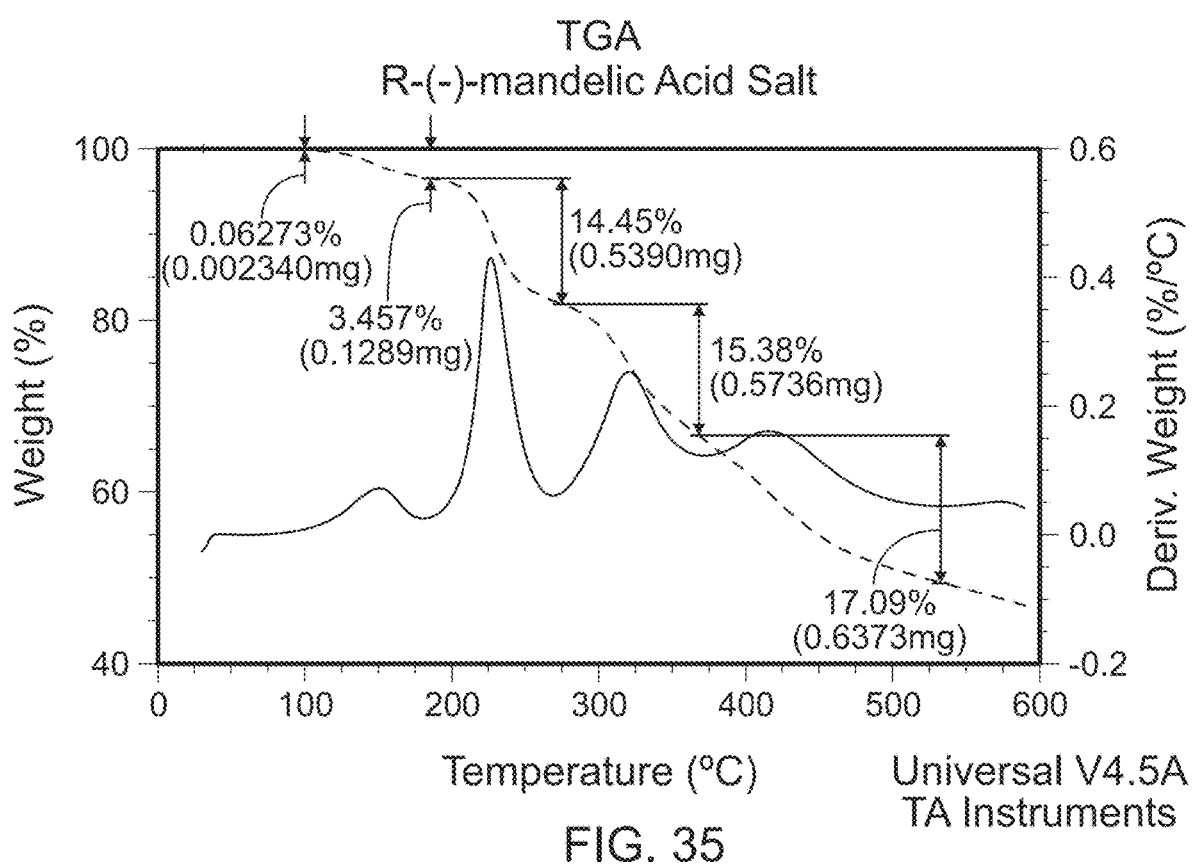
FIG. 35 shows the TGA thermogram of a solid form of Compound 1 R-(−)-mandelic acid salt.

The present invention further provides a (R)-(−)-mandelic acid salt of Compound 1. In some embodiments, a solid form of the (R)-(−)-mandelic acid salt has an XRPD pattern as shown on FIG. 33. In some embodiments, a solid form of the (R)-(−)-mandelic acid salt has a melting point of about 224° C. In some embodiments, a solid form of the (R)-(−)-mandelic acid salt has an endothermic event at about 223° C. or about 225° C. In some embodiments, a solid form of the (R)-(−)-mandelic acid salt has a DSC thermogram substantially as depicted in FIG. 34. In some embodiments, a solid form of the (R)-(−)-mandelic acid salt has a TGA thermogram substantially as depicted in FIG. 35.

In some embodiments, the (R)-(−)-mandelic acid salt of Compound 1 is a crystalline solid. In some embodiments, the crystalline solid of Compound 1 (R)-(−)-mandelic acid salt has at least one characteristic XRPD peak, in terms of 2-theta, selected from about 11.2, about 13.8, about 18.6, about 20.6, about 22.5, and about 24.1 degrees. In some embodiments, the crystalline solid of Compound 1 (R)-(−)-mandelic acid salt has at least two characteristic XRPD peaks, in terms of 2-theta, selected from about 11.2, about 13.8, about 18.6, about 20.6, about 22.5, and about 24.1 degrees. In some embodiments, the crystalline solid of Compound 1 (R)-(−)-mandelic acid salt has at least three characteristic XRPD peaks, in terms of 2-theta, selected from about 11.2, about 13.8, about 18.6, about 20.6, about 22.5, and about 24.1 degrees.

Salicylic Acid Salt

Figure 36:
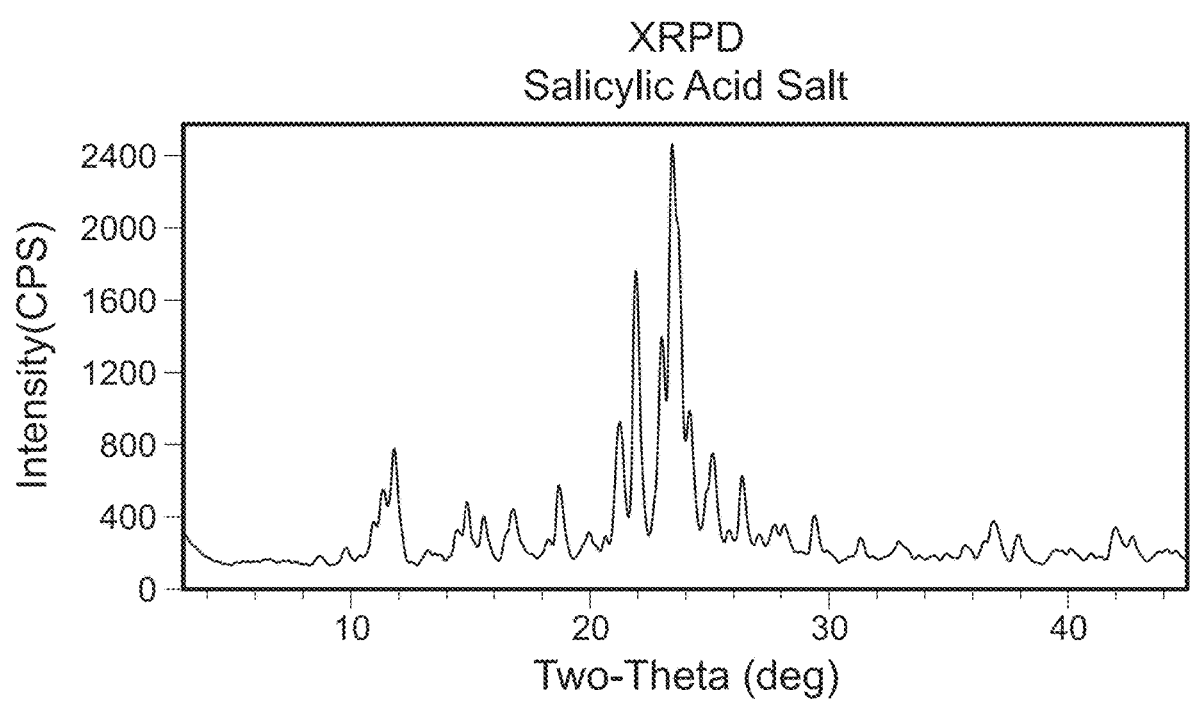
FIG. 36 shows the XRPD pattern of a solid form of Compound 1 salicylic acid salt.
Figure 37:
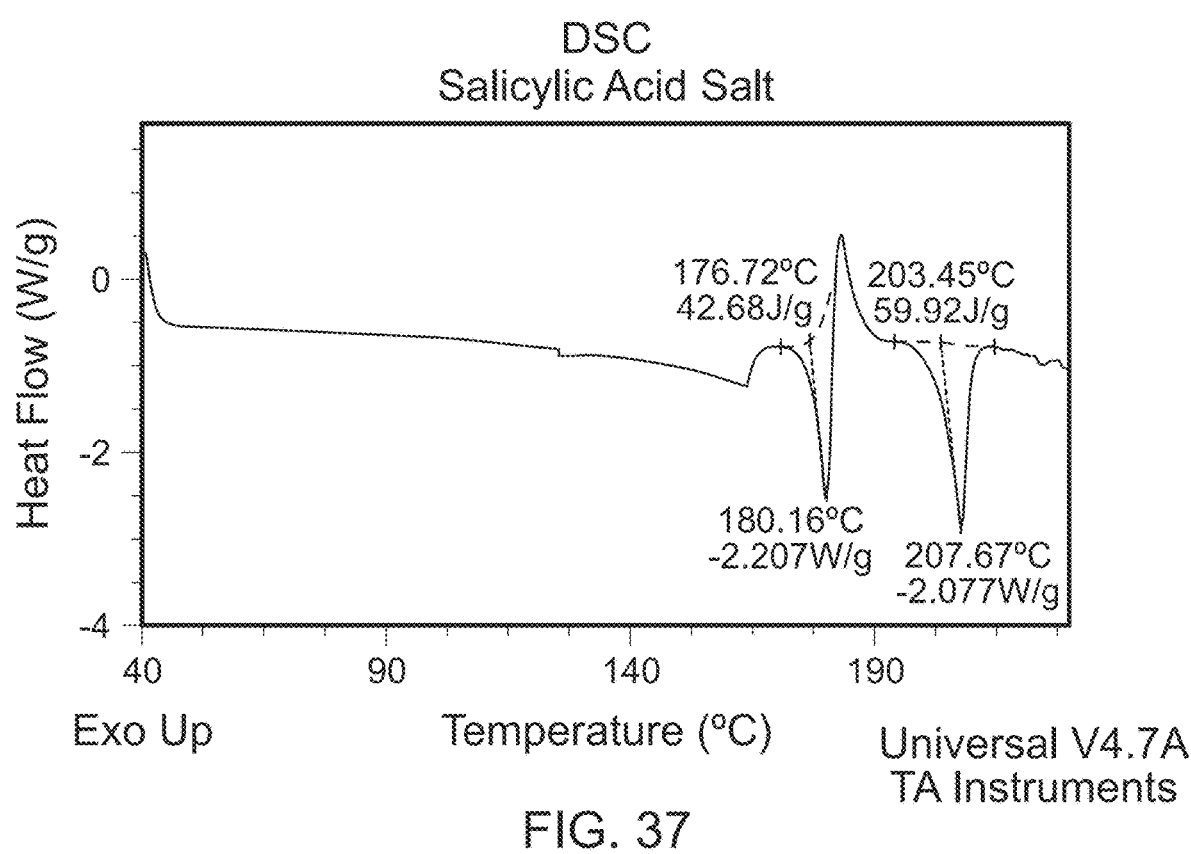
FIG. 37 shows the DSC thermogram of a solid form of Compound 1 salicylic acid salt.

In some embodiments, the salt of Compound 1 is a salicylic acid salt. In some embodiments, a solid form of the salicylic acid salt has an XRPD pattern as shown on FIG. 36. In some embodiments, a solid form of the salicylic acid salt has an endothermic event at about 180° C. or about 208° C. In some embodiments, a solid form of the salicylic acid salt has a DSC thermogram substantially as depicted in FIG. 37.

In some embodiments, the salicylic acid salt of Compound 1 is a crystalline solid. In some embodiments, the crystalline solid of Compound 1 salicylic acid salt has at least one characteristic XRPD peak, in terms of 2-theta, selected from about 21.2 and about 23.5 degrees. In some embodiments, the crystalline solid of Compound 1 salicylic acid salt has at least one characteristic XRPD peak, in terms of 2-theta, selected from about 11.8, about 16.7, about 18.7, about 21.2, about 21.9, about 23.0, about 23.5, and about 24.1 degrees. In some embodiments, the crystalline solid of Compound 1 salicylic acid salt has at least two characteristic XRPD peaks, in terms of 2-theta, selected from about 11.8, about 16.7, about 18.7, about 21.2, about 21.9, about 23.0, about 23.5, and about 24.1 degrees. In some embodiments, the crystalline solid of Compound 1 salicylic acid salt has at least three characteristic XRPD peaks, in terms of 2-theta, selected from about 11.8, about 16.7, about 18.7, about 21.2, about 21.9, about 23.0, about 23.5, and about 24.1 degrees.

Other Salts

The present invention further provides a benzoic acid salt of Compound 1. In some embodiments, a solid form of the benzoic acid salt has an XRPD pattern as shown on FIG. 38. In some embodiments, the benzoic acid salt of Compound 1 is a crystalline solid. In some embodiments, the crystalline solid of Compound 1 benzoic acid salt has at least one characteristic XRPD peak, in terms of 2-theta, selected from about 11.6, about 14.9, about 16.9, about 18.8, about 21.5, about 23.2, about 23.7, and about 24.9 degrees. In some embodiments, the crystalline solid of Compound 1 benzoic acid salt has at least two characteristic XRPD peaks, in terms of 2-theta, selected from about 11.6, about 14.9, about 16.9, about 18.8, about 21.5, about 23.2, about 23.7, and about 24.9 degrees. In some embodiments, the crystalline solid of Compound 1 benzoic acid salt has at least three characteristic XRPD peaks, in terms of 2-theta, selected from about 11.6, about 14.9, about 16.9, about 18.8, about 21.5, about 23.2, about 23.7, and about 24.9 degrees.

The present invention further provides a benzenesulfonic acid salt of Compound 1. In some embodiments, a solid form of the benzenesulfonic acid salt has an XRPD pattern as shown on FIG. 39. In some embodiments, the benzenesulfonic acid salt of Compound 1 is a crystalline solid. In some embodiments, the crystalline solid of Compound 1 benzenesulfonic acid salt has at least one characteristic XRPD peak, in terms of 2-theta, selected from about 6.6, about 9.1, about 12.9, about 13.3, about 14.5, about 18.0, about 23.5, and about 23.9 degrees. In some embodiments, the crystalline solid of Compound 1 benzenesulfonic acid salt has at least two characteristic XRPD peaks, in terms of 2-theta, selected from about 6.6, about 9.1, about 12.9, about 13.3, about 14.5, about 18.0, about 23.5, and about 23.9 degrees. In some embodiments, the crystalline solid of Compound 1 benzenesulfonic acid salt has at least three characteristic XRPD peaks, in terms of 2-theta, selected from about 6.6, about 9.1, about 12.9, about 13.3, about 14.5, about 18.0, about 23.5, and about 23.9 degrees.

The present invention further provides an L-pyroglutamic acid salt of Compound 1. In some embodiments, a solid form of the L-pyroglutamic acid salt has an XRPD pattern as shown on FIG. 40. In some embodiments, the L-pyroglutamic acid salt of Compound 1 is a crystalline solid. In some embodiments, the crystalline solid of Compound 1 L-pyroglutamic acid salt has at least one characteristic XRPD peak, in terms of 2-theta, selected from about 4.4, about 10.7, about 11.5, about 18.0, about 20.7, about 21.2, and about 22.9 degrees. In some embodiments, the crystalline solid of Compound 1 L-pyroglutamic acid salt has at least two characteristic XRPD peaks, in terms of 2-theta, selected from about 4.4, about 10.7, about 11.5, about 18.0, about 20.7, about 21.2, and about 22.9 degrees. In some embodiments, the crystalline solid of Compound 1 L-pyroglutamic acid salt has at least three characteristic XRPD peaks, in terms of 2-theta, selected from about 4.4, about 10.7, about 11.5, about 18.0, about 20.7, about 21.2, and about 22.9 degrees.

The present invention further provides a methanesulfonic acid salt of Compound 1. In some embodiments, a solid form of the methanesulfonic acid salt has an XRPD pattern as shown on FIG. 41. In some embodiments, the methanesulfonic acid salt of Compound 1 is a crystalline solid. In some embodiments, the crystalline solid of Compound 1 methanesulfonic acid salt has at least one characteristic XRPD peak, in terms of 2-theta, selected from about 13.5, about 14.7, about 16.7, about 18.6, about 19.3, about 20.0, about 20.7, about 22.4, about 25.7, about 26.8, about 27.2, and about 28.1 degrees. In some embodiments, the crystalline solid of Compound 1 methanesulfonic acid salt has at least two characteristic XRPD peaks, in terms of 2-theta, selected from about 13.5, about 14.7, about 16.7, about 18.6, about 19.3, about 20.0, about 20.7, about 22.4, about 25.7, about 26.8, about 27.2, and about 28.1 degrees. In some embodiments, the crystalline solid of Compound 1 methanesulfonic acid salt has at least three characteristic XRPD peaks, in terms of 2-theta, selected from about 13.5, about 14.7, about 16.7, about 18.6, about 19.3, about 20.0, about 20.7, about 22.4, about 25.7, about 26.8, about 27.2, and about 28.1 degrees.

The present invention further provides a (1 S)-(+)-10-camphorsulfonic acid salt of Compound 1. In some embodiments, a solid form of the (1S)-(+)-10-camphorsulfonic acid salt has an XRPD pattern as shown on FIG. 42. In some embodiments, the (1S)-(+)-10-camphorsulfonic acid salt of Compound 1 is a crystalline solid. In some embodiments, the crystalline solid of Compound 1 (1S)-(+)-10-camphorsulfonic acid salt has at least one characteristic XRPD peak, in terms of 2-theta, selected from about 7.1, about 10.9, about 13.6, about 16.1, about 17.7, about 18.8, about 19.9, and about 23.2 degrees. In some embodiments, the crystalline solid of Compound 1 (1S)-(+)-10-camphorsulfonic acid salt has at least two characteristic XRPD peaks, in terms of 2-theta, selected from about 7.1, about 10.9, about 13.6, about 16.1, about 17.7, about 18.8, about 19.9, and about 23.2 degrees. In some embodiments, the crystalline solid of Compound 1 (1S)-(+)-10-camphorsulfonic acid salt has at least three characteristic XRPD peaks, in terms of 2-theta, selected from about 7.1, about 10.9, about 13.6, about 16.1, about 17.7, about 18.8, about 19.9, and about 23.2 degrees.

The present invention further provides a fumaric acid salt. In some embodiments, a solid form of the fumaric acid salt has an XRPD pattern as shown on FIG. 43. In some embodiments, the fumaric acid salt is amorphous.

The present invention further provides a sulfuric acid salt of Compound 1. In some embodiments, a solid form of the sulfuric acid salt has an XRPD pattern as shown on FIG. 44. In some embodiments, the sulfuric acid salt is amorphous.

The present invention further provides an L-tartaric acid salt of Compound 1. In some embodiments, the L-tartaric acid salt is amorphous. A solid form of the L-tartaric acid salt has an XRPD pattern shown in FIG. 45.

The present invention further provides a D-tartaric acid salt of Compound 1. In some embodiments, the D-tartaric acid salt is amorphous. A solid form of the L-tartaric acid salt has an XRPD pattern shown in FIG. 46.

Synthetic Preparation of Phosphoric Acid Salts

Generally, the phosphoric acid salts of the invention can be prepared by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (referred to herein as "Compound 1" or "Compound 1 free base") with phosphoric acid. In some embodiments, the phosphoric acid is provided in molar excess relative to Compound 1 free base. In some embodiments, the combining of Compound 1 free base and phosphoric acid is carried out in the presence of a solvent. In some embodiments, the solvent comprises water, methanol, 2-propanol, or a mixture thereof. In some embodiments, the combining can be carried out at elevated temperature such as, for example, about 40 to about 80, about 50 to about 70, or about 55 to about 65° C. In some embodiments, the Compound 1 phosphoric acid salt product obtained from the combining is substantially crystalline. In some embodiments, the crystalline product comprises one or more of Forms I, II, III, IV, V, and VI. In some embodiments, the crystalline product comprises Form I. In some embodiments, the crystalline product substantially comprises Form I. In some embodiments, the Compound 1 phosphoric acid salt product obtained from the combining of phosphoric acid with Compound 1 is substantially amorphous or contains amorphous solid.

Compound 1 free base, a precursor to the phosphate salt, can be prepared by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide dihydrochloric acid salt (referred to herein as "Compound 1 dihydrochloric acid salt" or "Compound 1 dihydrochloride") with sodium carbonate. In some embodiments, the sodium carbonate is provided in molar excess with respect to Compound 1 dihydrochloride. In some embodiments, the combining of Compound 1 dihydrochloric acid and sodium carbonate is carried out in the presence of solvent. In some embodiments, the solvent comprises water, methylene chloride, or a mixture thereof. In some embodiments, the combining is carried out at room temperature or at elevated temperature. Example reaction temperatures include about 20 to about 40, about 20 to about 30, and about 23 to about 27° C.

Compound 1 dihydrochloric acid salt can be prepared by reacting tert-butyl {(3R,4R,5S)-4-{[tert-butyl(dimethyl)silyl]oxy}-1-[(7R)-7-{[tert-butyl(dimethyl)silyl]oxy}-3-({[6-(2,6-difluorophenyl)-5-fluoropyridin-2-yl]carbonyl}amino)-6,7-dihydro-5H-cyclopenta[b]pyridin-4-yl]-5-methylpiperidin-3-yl}carbamate (25):

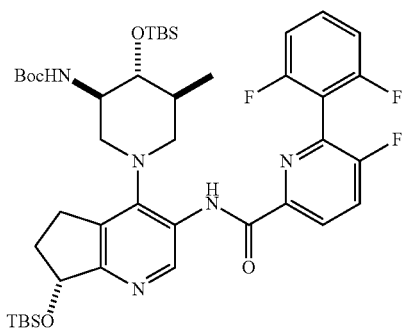

25 with hydrogen chloride. In some embodiments, the hydrogen chloride is provided in molar excess such as, for example, between about 2 and about 30, between about 5 and about 25, between about 10 and about 20, or about 15 equivalents with respect to (25). In some embodiments, the reacting with hydrogen chloride is carried out in the presence of a solvent. In some embodiments, the solvent comprises 1,4-dioxane, methanol, or a mixture thereof. In some embodiments, the reaction with hydrogen chloride is carried out at room temperature.

The intermediate (25) can be prepared by coupling tert-butyl ((3R,4R,5S)-1-(3-amino-7-{[tert-butyl(dimethyl)silyl]oxy}-6,7-dihydro-5H-cyclopenta[b]pyridin-4-yl)-4-{[tert-butyl(dimethyl)silyl]oxy}-5-methylpiperidin-3-yl)carbamate:

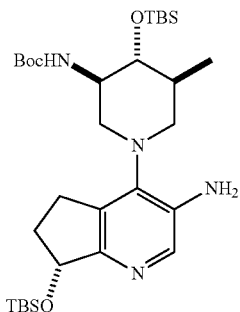

23 with 6-(2,6-difluorophenyl)-5-fluoropyridine-2-carboxylic acid:

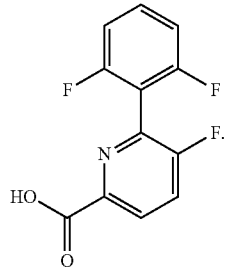

24

In some embodiments, (24) is provided in slight molar excess (e.g., about 1.1 to about 1.5 eq, or about 1.2 eq) with respect to (23). In some embodiments, the coupling is carried out in the presence of N,N-diisopropylethylamine (DIEA) and N,N,N',N'-tetramethyl-O-(7-azabenzotriazol-1-yl)uronium hexafluorophosphate (HATU). In some embodiments, the DIEA is provided in molar excess with respect to (23) (e.g., about 3 to 6 eq, or about 5 eq). In some embodiments, the HATU is provided in molar excess with respect to (23) (e.g., about 1.5 to 3.5 eq, or about 2.4 eq). In further embodiments, the coupling is carried out in the presence of a solvent. In some embodiments, the solvent comprises dimethylformamide (DMF). In some embodiments, the coupling is carried out at about 10 to about 40, or about 15 to about 30° C.

The intermediate (23) can be prepared by mixing tert-butyl ((3R,4R,5S)-1-((7R)-3-(aminocarbonyl)-7-{[tert-butyl(dimethyl)silyl]oxy}-6,7-dihydro-5H-cyclopenta[b]pyridin-4-yl)-4-{[tert-butyl(dimethyl)silyl]oxy}-5-methylpiperidin-3-yl)carbamate:

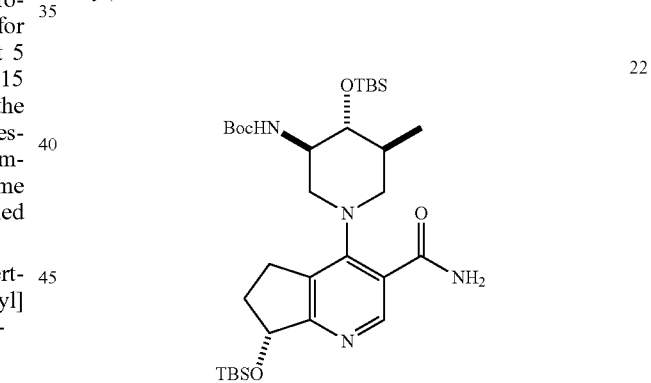

22 with tetra-N-butylammonium bromide (TBAB) in the presence of sodium hydroxide. In some embodiments, the TBAB is provided in an amount of about 1 eq with respect to (22). In some embodiments, the sodium hydroxide is provided in molar excess (e.g., about 1.1 to about 7 eq, or about 2 to about 4 eq, or about 4.5 eq with respect to (22). In some embodiments, the mixing is carried out in the presence of 1,3-dibromo-5,5-dimethylhydantoin. In some embodiments, the amount of 1,3-dibromo-5,5-dimethylhydantoin provided is less than 1 eq (e.g., about 0.1 to about 0.9 eq, or about 0.3 to about 0.8 eq, or about 0.7 eq) with respect to (22). In some embodiments, the mixing is carried out in the presence of solvent. In some embodiments, the solvent comprises tetrahydrofuran (THF). In some embodiments, the mixing is carried out at a temperature which is below room temperature, such as at about 0 to about 20, about 0 to about 15, or about 5 to about 10° C.

The intermediate (22) can be prepared by reacting tert-butyl [(3R,4R,5S)-4-{[tert-butyl(dimethyl)silyl]oxy}-1-((7R)-7-{[tert-butyl(dimethyl)silyl]oxy}-3-cyano-6,7-dihydro-5H-cyclopenta[b]pyridin-4-yl)-5-methylpiperidin-3-yl]carbamate:

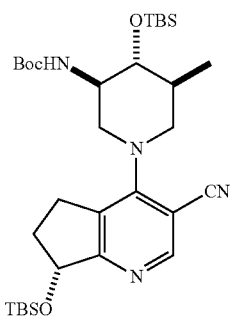

21 with acetaldoxime. In some embodiments, the reacting with acetaldoxime is carried out in the presence of a palladium catalyst such as [1,1'-bis(diphenylphosphino)ferrocene]-dichloropalladium(II)(Pd(dppf)$_2$Cl$_2$ complexed with dichloromethane. In some embodiments, the acetaldoxime is provided in molar excess (e.g., about 2 to about 20 eq, about 5 to about 15 eq, or about 10 eq). In some embodiments, the total amount of acetaldoxime is delivered to the reaction mixture in portions. In some embodiments, the reacting with acetaldoxime is carried out in the presence of a solvent. In some embodiments, the solvent comprises water, ethanol, or a mixture thereof. In some embodiments, the reacting is carried out at elevated temperature (e.g., about 50 to about 150, about 70 to about 100, or about 90° C.).

The intermediate (21) can be prepared by reacting (7R)-7-{[tert-butyl(dimethyl)silyl]oxy}-4-chloro-6,7-dihydro-5H-cyclopenta[b]pyridine-3-carbonitrile:

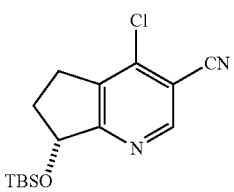

20 with tert-butyl ((3R,4R,5S)-4-{[tert-butyl(dimethyl)silyl]oxy}-5-methylpiperidin-3-yl)carbamate (9), or hydrochloric acid salt thereof (9 HCl):

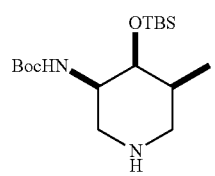

9 in the presence of N,N-diisopropylethylamine (DIEA). In some embodiments, intermediate (9) is provided in slight molar excess (e.g., 1.05 eq) relative to (20). In some embodiments, the DIEA is provided in molar excess (e.g., about 2 to about 6 eq, or about 4 eq) relative to (20). In some embodiments, the reacting of (20) with (9) is carried out in the presence of a solvent. In some embodiments, the solvent comprises dimethylsulfoxide. In some embodiments, the reacting is carried out at room temperature or at elevated temperature (e.g., at about 30 to about 150, or at about 100° C.).

The intermediate (R)-7-(tert-butyldimethylsilyloxy)-4-chloro-6,7-dihydro-5H-cyclopenta[b]pyridine-3-carbonitrile (20) can be prepared by reacting (R)-7-(tert-butyldimethylsilyloxy)-4-chloro-6,7-dihydro-5H-cyclopenta[b]pyridine-3-carbaldehyde (19):

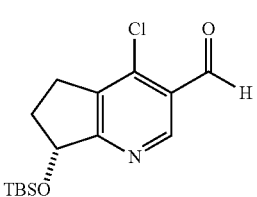

19 with ammonia and iodine. In some embodiments, the reacting is carried out in the presence of a solvent. In some embodiments the solvent comprises water, THF, or a mixture thereof. In some embodiments the reacting is carried out at a temperature below room temperature, for example between about 10 and 22° C. In some embodiments, the ammonia and iodine are provided in molar excess.

The intermediate (R)-7-(tert-butyldimethylsilyloxy)-4-chloro-6,7-dihydro-5H-cyclopenta[b]pyridine-3-carbaldehyde (19) can be prepared by combining (R)-7-(tert-butyldimethylsilyloxy)-4-chloro-6,7-dihydro-5H-cyclopenta[b]pyridine (18):

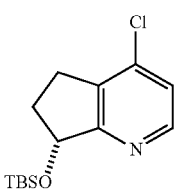

18 with n-butyl lithium in the presence of 2,2,6,6-tetramethylpiperidine followed by adding N,N-dimethylformamide (DMF). In some embodiments, the combining is carried out below room temperature such as, for example, from −100 to −10° C. In some embodiments, the combining is carried out in a solvent. In some embodiments, the solvent comprises THF, hexane, or a mixture thereof.

The intermediate (R)-7-(tert-butyldimethylsilyloxy)-4-chloro-6,7-dihydro-5H-cyclopenta[b]pyridine (18) can be prepared by reacting (R)-4-chloro-6,7-dihydro-5H-cyclopenta[b]pyridin-7-ol (17):

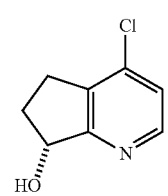

17 with tert-butyldimethylsilyl chloride and 1H-imidazole. In some embodiments, the reacting is carried out at a temperature below room temperature, such as at about −15 to 15 or about −15 to 0° C. In some embodiments, the reacting is carried out in the presence of a solvent such as methylene chloride or other organic solvent. In some embodiments, the tert-butyldimethylsilyl chloride is provided in an amount of about 1 equivalent with respect to (17). In some embodiments, the 1H-imidazole is provided in molar excess with respect to (17).

The intermediate (R)-4-chloro-6,7-dihydro-5H-cyclopenta[b]pyridin-7-ol (17) can be prepared by reacting 4-chloro-5H-cyclopenta[b]pyridin-7(6H)-one (16):

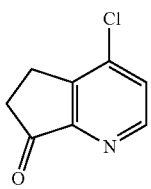

16 with formic acid in the presence of RuCl(p-cymene)[(R,R)-Ts-DPEN] and triethylamine (TEA). In some embodiments, the reacting is carried out in the presence of a solvent such as methylene chloride or other organic solvent. In some embodiments, the reacting is carried out at a temperature below room temperature. In some embodiments, the RuCl(p-cymene)[(R,R)-Ts-DPEN] is provided in a catalytic amount. In some embodiments, the TEA is provided in molar excess relative to (16). In some embodiments, the formic acid is provided in molar excess relative to (16).

The intermediate 4-chloro-5H-cyclopenta[b]pyridin-7(6H)-one (16) can be prepared by reacting 4-chloro-6,7-dihydro-5H-cyclopenta[b]pyridin-7-ol (15):

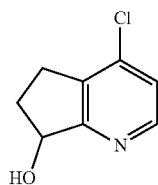

15 with pyridine-sulfur trioxide in the presence of N,N-diisopropylethylamine. In some embodiments, (15) and N,N-diisopropylethylamine are combined prior to addition of pyridine-sulfur trioxide. In some embodiments, the reacting is carried out in the presence of solvent. In some embodiments, the solvent comprises methylene chloride or other organic solvent. In some embodiments, the reaction is carried out below room temperature, such as at about 0° C. In some embodiments, the N,N-diisopropylethylamine is provided in molar excess relative to (15). In some embodiments, the pyridine-sulfur trioxide is provided in molar excess relative to (15).

The intermediate 4-chloro-6,7-dihydro-5H-cyclopenta[b]pyridin-7-ol (15) can be prepared by reacting 4-chloro-6,7-dihydro-5H-cyclopenta[b]pyridin-7-yl acetate (14):

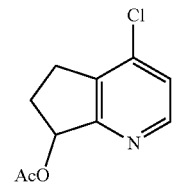

14 wherein Ac is acetyl, with potassium carbonate. In some embodiments, the reacting is carried out in the presence of solvent such as methanol, water, other polar solvent, or mixture thereof. In some embodiments, the reacting is carried out below room temperature, such as at about 0° C. In some embodiments, the potassium carbonate is provided in molar excess relative to (14).

The intermediate 4-chloro-6,7-dihydro-5H-cyclopenta[b]pyridin-7-yl acetate (14) can be prepared by reacting 4-chloro-6,7-dihydro-5H-cyclopenta[b]pyridine 1-oxide (13):

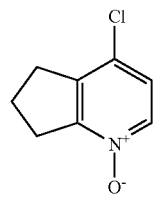

13 with acetic anhydride. In some embodiments, the reacting is carried out in the presence of an organic solvent, wherein the organic solvent comprises toluene or other non-polar solvent. In some embodiments, the reacting is carried out at elevated temperature, such as at about 50 to about 150, or about 70 to about 90, or about 80 to about 85° C. In some embodiments, the acetic anhydride is provided in molar excess relative to (13).

The intermediate 4-chloro-6,7-dihydro-5H-cyclopenta[b]pyridine 1-oxide (13) can be prepared by reacting 4-chloro-6,7-dihydro-5H-cyclopenta[b]pyridine (12):

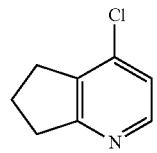

12 with urea hydrogen peroxide (UHP) in the presence of a catalyst. In some embodiments, the catalyst is a transition metal catalyst such as methyltrioxorhemium(VII). In some embodiments, the catalyst is provided in a catalytic amount (e.g., <0.1 eq relative to (12)). In some embodiments, the reacting is carried out in the presence of solvent. In some embodiments, the solvent comprises methanol or other polar solvent. In some embodiments, the reacting is carried out at room temperature. In some embodiments, the UHP is provided in an amount of about 1 to about 2 equivalents, or in an amount of about 1.5 equivalents with respect to (12).

The intermediate 4-chloro-6,7-dihydro-5H-cyclopenta[b]pyridine (12) can be prepared by reacting 6,7-dihydro-5H-cyclopenta[b]pyridine 1-oxide (11):

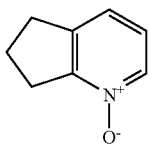

11 with phosphoryl chloride. In some embodiments, the phosphoryl chloride is provided in an amount of about 2-4 equivalents, or about 3 equivalents with respect to (11). In some embodiments, the reacting is carried out in the presence of an organic solvent, where the organic solvent comprise, for example, toluene. In some embodiments, the reacting is carried out at elevated temperature such as at about 50 to about 100, or about 70 to about 90, or about 80 to about 85° C.

The intermediate 6,7-dihydro-5H-cyclopenta[b]pyridine 1-oxide (11) can be prepared by reacting 6,7-dihydro-5H-cyclopenta[b]pyridine (10):

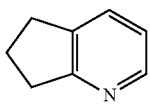

10 with urea hydrogen peroxide UHP in the presence of a catalyst. In some embodiments, the catalyst is a transition metal catalyst such as methyltrioxorhenium(VII). In some embodiments, the catalyst is provided in a catalytic amount (e.g., <0.1 eq relative to (10)). In some embodiments, the reacting is carried out at about room temperature. In some embodiments the UHP is provided in an amount of about 2-4 eq or about 3 eq with respect to (10). In some embodiments, the reacting is carried out in the presence of solvent, such as a solvent comprising methanol or other polar organic solvent. In some embodiments, the present invention relates to an intermediate compound selected from:

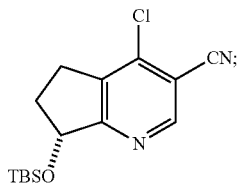

20

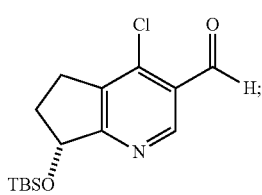

19

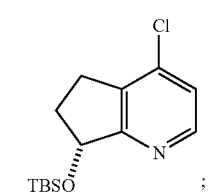

18

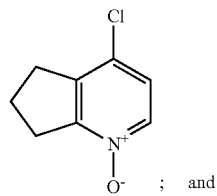

13

; and

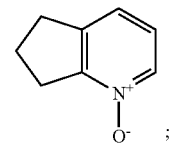

11

;

wherein TBS is tert-butyl(dimethyl)silyl.

In some embodiments, the present invention relates to an intermediate compound selected from:

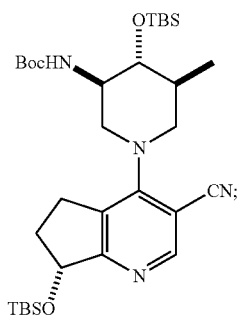

21

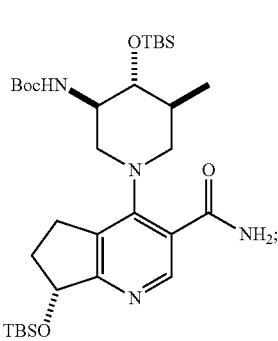

22

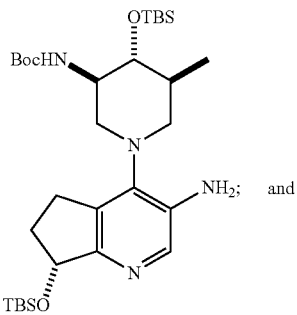

23

; and

-continued

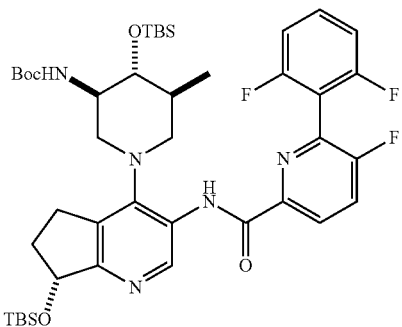

wherein TBS is tert-butyl(dimethyl)silyl and Boc is tert-butyloxycarbonyl.

In some embodiments, the intermediate compound is

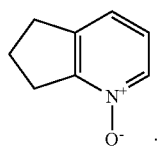

11

In some embodiments, the intermediate compound is

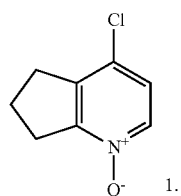

13

In some embodiments, the intermediate compound is

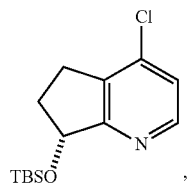

18 wherein TBS is tert-butyl(dimethyl)silyl.

In some embodiments, the intermediate compound is

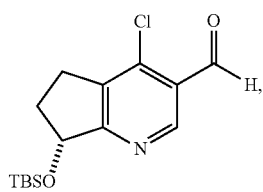

19 wherein TBS is tert-butyl(dimethyl)silyl.

In some embodiments, the intermediate compound is

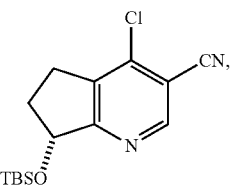

20 wherein TBS is tert-butyl(dimethyl)silyl.

In some embodiments, the intermediate compound is

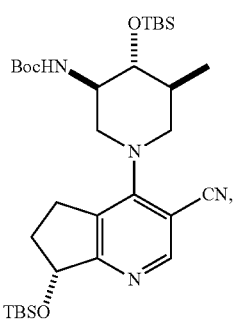

21 wherein TBS is tert-butyl(dimethyl)silyl and Boc is tert-butyloxycarbonyl.

In some embodiments, the intermediate compound is

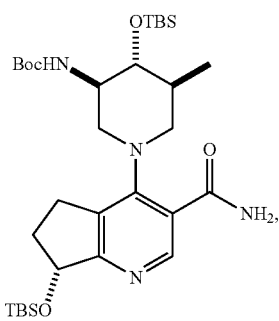

22 wherein TBS is tert-butyl(dimethyl)silyl and Boc is tert-butyloxycarbonyl.

In some embodiments, the intermediate compound is

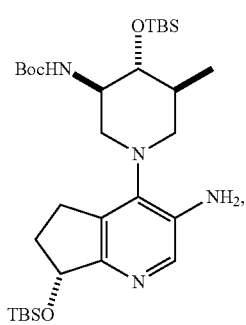

23 wherein TBS is tert-butyl(dimethyl)silyl and Boc is tert-butyloxycarbonyl.

In some embodiments, the intermediate compound is

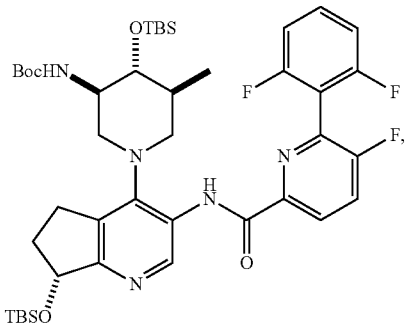

wherein TBS is tert-butyl(dimethyl)silyl and Boc is tert-butyloxycarbonyl.

In some embodiments, the present invention provides a method of preparing Compound 1 phosphoric acid salt, comprising:
reacting Compound 10 with urea hydrogen peroxide and methyltrioxorhenium(VII) to form Compound 11;
reacting Compound 11 with phosphoryl chloride to form Compound 12;
reacting Compound 12 with urea hydrogen peroxide and methyltrioxorhemium(VII) to form Compound 13;
reacting Compound 13 with acetic anhydride to form Compound 14;
reacting Compound 14 with potassium carbonate to form Compound 15;
reacting Compound 15 with pyridine-sulfur trioxide in the presence of N,N-diisopropylethylamine to form Compound 16;
reacting Compound 16 with formic acid in the presence of RuCl(p-cymene)[(R,R)-Ts-DPEN] and triethylamine (TEA) to form Compound 17;
reacting Compound 17 with tert-butyldimethylsilyl chloride and 1H-imidazole to form Compound 18;
combining Compound 18 with n-butyl lithium in the presence of 2,2,6,6-tetramethylpiperidine followed by adding N,N-dimethylformamide (DMF) to form Compound 19;
reacting Compound 19 with ammonia and iodine to form Compound 20;
reacting Compound 20 with Compound 9, or hydrochloric acid salt thereof, in the presence of N,N-diisopropylethylamine (DIEA) to form Compound 21;
reacting compound 21 with acetaldoxime to form Compound 22;
mixing Compound 22 with tetra-N-butylammonium bromide (TBAB) in the presence of sodium hydroxide to form Compound 23;
coupling Compound 23 with Compound 24 to form Compound 25;
reacting Compound 25 with hydrogen chloride to form Compound 1 dihydrochloric acid salt;
combining Compound 1 dihydrochloric acid salt with sodium carbonate to form Compound 1 free base; and
combining Compound 1 free base with phosphoric acid to form Compound 1 phosphoric acid salt.

In some embodiments, the present invention provides a method of preparing Compound 1 phosphoric acid salt, comprising:
reacting Compound 19 with ammonia and iodine to form Compound 20;
reacting Compound 20 with Compound 9, or hydrochloric acid salt thereof, in the presence of N,N-diisopropylethylamine (DIEA) to form Compound 21;
reacting compound 21 with acetaldoxime to form Compound 22;
mixing Compound 22 with tetra-N-butylammonium bromide (TBAB) in the presence of sodium hydroxide to form Compound 23;
coupling Compound 23 with Compound 24 to form Compound 25;
reacting Compound 25 with hydrogen chloride to form Compound 1 dihydrochloric acid salt;
combining Compound 1 dihydrochloric acid salt with sodium carbonate to form Compound 1 free base; and
combining Compound 1 free base with phosphoric acid to form Compound 1 phosphoric acid salt.

In some embodiments, the present invention provides a method of preparing Compound 20, comprising:
reacting Compound 10 with urea hydrogen peroxide and methyltrioxorhenium(VII) to form Compound 11;
reacting Compound 11 with phosphoryl chloride to form Compound 12;
reacting Compound 12 with urea hydrogen peroxide and methyltrioxorhemium(VII) to form Compound 13;
reacting Compound 13 with acetic anhydride to form Compound 14;
reacting Compound 14 with potassium carbonate to form Compound 15;
reacting Compound 15 with pyridine-sulfur trioxide in the presence of N,N-diisopropylethylamine to form Compound 16;
reacting Compound 16 with formic acid in the presence of RuCl(p-cymene)[(R,R)-Ts-DPEN] and triethylamine (TEA) to form Compound 17;
reacting Compound 17 with tert-butyldimethylsilyl chloride and 1H-imidazole to form Compound 18;
combining Compound 18 with n-butyl lithium in the presence of 2,2,6,6-tetramethylpiperidine followed by adding N,N-dimethylformamide (DMF) to form Compound 19; and
reacting Compound 19 with ammonia and iodine to form Compound 20.

As used herein, the term "reacting" is used as known in the art and generally refers to the bringing together of chemical reagents in such a manner so as to allow their interaction at the molecular level to achieve a chemical or physical transformation. In some embodiments, the reacting involves at least two reagents. In some embodiments, the reacting step of a synthetic process may involve one or more substances in addition to the reagents such as solvent and/or a catalyst. The reacting steps of the processes described herein can be conducted for a time and under conditions suitable for preparing the identified product. The terms "combining" and "mixing" with respect to reagents of a chemical reaction are used interchangeably with the term "reacting" herein. The term "coupling" also can be considered interchangeable with "reacting" but may be used in conjunction with a reaction step that involves the linking of two organic fragments.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis*, 4$^{th}$ Ed., John Wiley & Sons: New York, 2006, which is incorporated herein by reference in its entirety.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the reaction step, suitable solvent(s) for that particular reaction step can be selected. Appropriate solvents include water, alkanes (such as pentanes, hexanes, heptanes, cyclohexane, etc., or a mixture thereof), aromatic solvents (such as benzene, toluene, xylene, etc.), alcohols (such as methanol, ethanol, isopropanol, etc.), ethers (such as dialkylethers, methyl tert-butyl ether (MTBE), tetrahydrofuran (THF), dioxane, etc.), esters (such as ethyl acetate, butyl acetate, etc.), halogenated hydrocarbon solvents (such as dichloromethane (DCM), chloroform, dichloroethane, tetrachloroethane), dimethylformamide (DMF), dimethylsulfoxide (DMSO), acetone, acetonitrile (ACN), hexamethylphosphoramide (HMPA) and N-methyl pyrrolidone (NMP). Such solvents can be used in either their wet or anhydrous forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Preparation of Phosphate Salt Crystalline Forms I-VI

Form I can be prepared, for example, by precipitating the solid form from a solution comprising N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt. In some embodiments, the solution comprises a solvent that comprises 2-propanol. In other embodiments, the solution comprises a solvent that comprises acetonitrile and/or ethanol. The precipitating can be carried out at any suitable temperature, such as about room temperature or at elevated temperature. The precipitating can be carried out by any means which concentrates the solution, such as by evaporation, addition of anti-solvent, or cooling.

Form II can be prepared, for example, by precipitating the solid form from a solution of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt in a solvent comprising dimethylformamide (DMF). The precipitating can be carried out by any means which concentrates the solution, such as by evaporation, addition of anti-solvent, or cooling. In some embodiments, the precipitating is carried out by evaporation under air at about room temperature (e.g., about 25° C.).

Form III can be prepared by precipitating the solid form from a solution of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt in a solvent comprising dimethylformamide (DMF), wherein the precipitating can be carried out at elevated temperature, such as at about 30° C. to about 70° C., at about 40° C. to about 60° C., or at about 50° C.

Form IV can be prepared by precipitating the solid form from an aqueous solution of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt. In some embodiments, the precipitating is carried out by evaporation under air at elevated temperature such as, for example, between about 30° C. and about 70° C., between about 40° C. and about 60° C., or between about 45° C. and about 55° C.

Form V can be prepared by precipitating the solid form from an aqueous solution of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt by cooling the solution. In some embodiments, the aqueous solution is at a temperature of about 30 to about 40° C., or about 35° C. prior to cooling. In some embodiments, the solution is cooled to about 4-5° C. In some embodiments, the cooling is carried out by quench-cooling.

Form VI can be prepared by filtering a slurry of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-

6-(2,6-difluorophenyl)-5-fluoropyridine-2-carboxamide phosphoric acid salt in water to obtain a filtrate and then cooling the filtrate. (e.g., to below about 10° C., or to about 4-5° C.).

Synthetic Preparation of Other Salt Forms

The dihydrochloric acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with hydrochloric acid. In some embodiments, the combining is carried out in the presence of a solvent, such as a solvent comprising 2-propanol and/or 2-propyl acetate. In some embodiments, the hydrochloric acid is provided in molar excess with respect to Compound 1 free base. In some embodiments, the molar ratio of Compound 1 free base to hydrochloric acid is from about 1:2 to about 1:2.5. In some embodiments, the ratio of Compound 1 free base to hydrochloric acid is about 1:2.34.

The monohydrochloric acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with hydrochloric acid. In some embodiments, the combining is carried out in the presence of solvent such as a solvent comprising 2-propanol and/or 2-propyl acetate. In some embodiments, the molar ratio of Compound 1 free base to hydrochloric acid is from about 1:1 to about 1:1.5. In some embodiments, the molar ratio of Compound 1 free base to hydrochloric acid is about 1:1.12.

The maleic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with maleic acid. In some embodiments, combining is carried out in the presence of a solvent such as a solvent comprising 2-propanol. In some embodiments, the molar ratio of Compound 1 free base to maleic acid is from about 1:1 to about 1:1.5. In some embodiments, the molar ratio of Compound 1 free base to maleic acid is about 1:1.21. In some embodiments, the method comprises adding seed crystals to induce precipitation.

The adipic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with adipic acid. In some embodiments, the combining is carried out in the presence of a solvent such as a solvent comprising 2-propanol and/or heptane. In some embodiments, the molar ratio of Compound 1 free base to adipic acid is from about 1:2 to about 1:3. In some embodiments, the molar ratio of Compound 1 free base to adipic acid is about 1:2.49.

Hydrobromic acid salts can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with hydrobromic acid. In some embodiments, the combining is carried out in the presence of a solvent such as a solvent comprising 2-propanol and/or water. In some embodiments, the molar ratio of Compound 1 free base to hydrobromic acid is from about 1:2 to about 1:3 during the combining. In some embodiments, the molar ratio of Compound 1 free base to hydrobromic acid is about 1:2.4. In some embodiments, the hydrobromic acid salt is a dihydrobromic acid salt. In further embodiments, the hydrobromic acid salt is a monohydrobromic acid salt.

The mandelic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with (R)-(−)-mandelic acid. In some embodiments, the combining is carried out in the presence solvent, such as a solvent comprising 2-propanol. In some embodiments, the molar ratio of Compound 1 free base to (R)-(−)-mandelic acid is from about 1:1 to about 1:1.5 during the combining. In some embodiments, the molar ratio of Compound 1 free base to (R)-(−)-mandelic acid is about 1:1.06.

The salicylic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with salicylic acid, optionally in the presence of a solvent. In some embodiments, the solvent comprises isopropyl alcohol. In some embodiments, the acid is provided in molar excess with respect to Compound 1 free base. In some embodiments, the molar ratio of Compound 1 free base to salicylic acid is from about 1:1 to about 1:1.5 or about 1:1 to about 1:1.2. In some embodiments, the molar ratio of Compound 1 free base to salicylic acid is about 1:1.16. In some embodiments, the combining is carried out at about room temperature.

The benzoic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with benzoic acid, optionally in the presence of a solvent. In some embodiments, the solvent comprises isopropyl alcohol. In some embodiments, the acid is provided in molar excess with respect to Compound 1 free base. In some embodiments, the molar ratio of Compound 1 free base to benzoic acid is from about 1:1 to about 1:1.5 or about 1:1 to about 1:1.2. In some embodiments, the molar ratio of Compound 1 free base to benzoic acid is about 1:1.16. In some embodiments, the combining is carried out at about room temperature.

The benzenesulfonic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with benzenesulfonic acid optionally in the presence of a solvent. In some embodiments, the solvent comprises isopropyl alcohol. In some embodiments, the acid is provided in molar excess with respect to Compound 1 free base. In some embodiments, the molar ratio of Compound 1 free base to benzenesulfonic acid is from about 1:1 to about 1:1.5 or about 1:1 to about 1:1.2. In some embodiments, the molar ratio of Compound 1 free base to benzenesulfonic acid is about 1:1.1. In some embodiments, the combining is carried out at about room temperature.

The L-pyroglutamic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with L-pyroglutamic acid optionally in the presence of a solvent In some embodiments, the solvent comprises isopropyl alcohol. In some embodiments, the solvent comprises isopropyl alcohol and heptane. In some embodiments, the acid is provided in molar excess with respect to Compound 1 free base. In some embodiments, the molar ratio of Compound 1 free base to L-pyroglutamic acid is from about 1:1 to about 1:1.5 or about 1:1 to about 1:1.2. In some embodiments, the molar ratio of Compound 1 free base to L-pyroglutamic acid is about 1:1.12. In some embodiments, the combining is carried out at about room temperature.

The methanesulfonic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with methanesulfonic acid optionally in the presence of a solvent. In some embodiments, the solvent comprises isopropyl alcohol. In some embodiments, the solvent comprises isopropyl alcohol and ethanol. In some embodiments, the solvent comprises isopropyl alcohol, ethanol, and heptane. In some embodiments, the acid is provided in molar excess with respect to Compound 1 free base. In some embodiments, the molar ratio of Compound 1 free base to methanesulfonic acid is from about 1:1 to about 1:1.5 or about 1:1 to about 1:1.2. In some embodiments, the molar ratio of Compound 1 free base to methanesulfonic acid is about 1:1.1. In some embodiments, the combining is carried out at about room temperature.

The (1S)-(+)-10-camphorsulfonic acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with (1S)-(+)-10-camphorsulfonic acid optionally in the presence of a solvent. In some embodiments, the solvent comprises isopropyl alcohol. In some embodiments, the solvent comprises isopropyl alcohol and heptane. In some embodiments, the acid is provided in molar excess with respect to Compound 1 free base. In some embodiments, the molar ratio of Compound 1 free base to (1S)-(+)-10-camphorsulfonic acid is from about 1:1 to about 1:1.5 or about 1:1 to about 1:1.2. In some embodiments, the molar ratio of Compound 1 free base to (1S)-(+)-10-camphorsulfonic acid is about 1:1.1. In some embodiments, the combining is carried out at about room temperature.

The fumaric acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with fumaric acid optionally in the presence of a solvent. In some embodiments, the solvent comprises isopropyl alcohol. In some embodiments, the solvent comprises isopropyl alcohol and heptane. In some embodiments, the acid is provided in molar excess with respect to Compound 1 free base. In some embodiments, the molar ratio of Compound 1 free base to fumaric acid is about 1:1.16. In some embodiments, the combining is carried out at about room temperature.

The sulfuric acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with sulfuric acid optionally in the presence of a solvent. In some embodiments, the solvent comprises isopropyl alcohol. In some embodiments, the acid is provided in molar excess with respect to Compound 1 free base. In some embodiments, the molar ratio of Compound 1 free base to sulfuric acid is from about 1:1 to about 1:1.5 or about 1:1 to about 1:1.2. In some embodiments, the molar ratio of Compound 1 free base to sulfuric acid is about 1:1.1. In some embodiments, the combining is carried out at about room temperature.

The L-tartaric acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with L-tartaric acid optionally in the presence of a solvent. In some embodiments, the solvent comprises isopropyl alcohol. In some embodiments, the solvent comprises isopropyl alcohol and heptane. In some embodiments, the acid is provided in molar excess with respect to Compound 1 free base. In some embodiments, the molar ratio of Compound 1 free base to L-tartaric acid is from about 1:1 to about 1:1.5 or about 1:1 to about 1:1.2. In some embodiments, the molar ratio of Compound 1 free base to L-tartaric acid is about 1:1.16. In some embodiments, the combining is carried out at about room temperature.

The D-tartaric acid salt can be prepared, for example, by combining N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) with D-tartaric acid optionally in the presence of a solvent. In some embodiments, the solvent comprises isopropyl alcohol. In some embodiments, the solvent comprises isopropyl alcohol and heptane. In some embodiments, the acid is provided in molar excess with respect to Compound 1 free base. In some embodiments, the molar ratio of Compound 1 free base to D-tartaric acid is from about 1:1 to about 1:1.5 or about 1:1 to about 1:1.2. In some embodiments, the molar ratio of Compound 1 free base to D-tartaric acid is about 1:1.16. In some embodiments, the combining is carried out at about room temperature.

Methods of Use

Compound 1 and the salts described herein can inhibit the activity of one or more members of the Pim kinase family and, thus, is useful in treating diseases and disorders associated with activity of Pim kinases. For example, Compound 1 and its salts can inhibit one or more of Pim1, Pim2 and Pim3. Thus, the present disclosure provides methods of treating a Pim kinase-associated disease or disorder in an individual (e.g., patient) by administering to the individual in need of such treatment a therapeutically effective amount or dose of Compound 1 phosphoric acid salt, or any of the embodiments thereof, or a pharmaceutical composition thereof. The present disclosure also provides a Compound 1 phosphoric acid salt, or any of the embodiments thereof, or a pharmaceutical composition thereof, for use in treating a Pim kinase-associated disease or disorder. Also provided is the use of Compound 1 phosphoric acid salt, or any of the embodiments thereof, or a pharmaceutical composition thereof, in the manufacture of a medicament for treating a Pim kinase-associated disease or disorder.

A Pim kinase-associated disease can include any disease, disorder or condition that is directly or indirectly linked to expression or activity of the Pim kinase, including overexpression and/or abnormal activity levels. Abnormal activity levels can be determined by comparing activity level in normal, healthy tissue or cells with activity level in diseased cells. A Pim kinase-associated disease can also include any disease, disorder or condition that can be prevented, ameliorated, inhibited or cured by modulating Pim kinase activity. In some embodiments, the disease is characterized by the abnormal activity or expression (e.g., overexpression) of one or more Pim1, Pim2 and Pim3. In some embodiments, the disease is characterized by mutant Pim1, Pim2 or Pim3. A Pim kinase associated disease can also refer to any disease, disorder or condition wherein modulating the expression or activity of one or more Pim kinases is beneficial.

Pim kinase associated diseases that can be treated according to the invention include cancer, including, in particular, cancers in which Pim kinases are upregulated or an oncogene, e.g., Myc or BCL2, is activated. Pim kinase associated diseases include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Pim kinase associated diseases also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Pim kinase associated diseases that can be treated according to the invention also include myeloproliferative disorders such as polycythemia vera (PV), essential thrombocythemia (ET), chronic myelogenous leukemia (CML) and the like. The myeloproliferative disorder can be myelofibrosis such as primary myelofibrosis (PMF), post-polycythemia vera/essential thrombocythemia myelofibrosis (Post-PV/ET MF), post-essential thrombocythemia myelofibrosis (Post-ET MF) or post-polycythemia vera myelofibrosis (Post-PV MF).

Pim kinase-associated diseases that can be treated according to the invention also include immune disorders such as autoimmune diseases. The immune disorders include multiple sclerosis, rheumatoid arthritis, allergy, food allergy, asthma, lupus, inflammatory bowel disease and ulcerative colitis.

Pim kinase-associated diseases that can be treated according to the invention also include atherosclerosis.

The salts of the invention can also be used to inhibit disease processes in which Pim-kinases are involved, including angiogenesis and tumor metastasis.

Due to the fact that Pim kinases are regulated by the JAK/STAT pathway, the salts of the invention are useful to treat diseases in which modulating JAK/STAT signaling is beneficial. Thus, other diseases that can be treated include Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft versus host disease, Sjogren's syndrome, glomerulonephritis and diabetes mellitus (type I).

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the salts of the present invention may be useful in preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the Pim inhibitor of the present invention can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the Pim inhibitor provided herein for treatment of diseases such as cancer include an FGFR inhibitor (FGFR1, FGFR2, FGFR3 or FGFR4), a JAK inhibitor (JAK1 and/or JAK2, e.g., ruxolitinib, baricitinib or INCB39110), an IDO inhibitor (e.g., epacadostat and NLG919), a TDO inhibitor, a PI3K-delta inhibitor, a PI3K-gamma inhibitor, a CSF1R inhibitor, a TAM receptor tyrosine kinases (Tyro-3, Axl, and Mer), an angiogenesis inhibitor, an interleukin receptor inhibitor and an adenosine receptor antagonist or combinations thereof. Additionally, the Pim inhibitors of the invention can be combined with inhibitors of kinases associated with the PIK3/Akt/mTOR signaling pathway, such as PI3K, Akt (including Akt1, Akt2 and Akt3) and mTOR kinases.

In some embodiments Pim inhibitors of the invention can be combined with inhibitors selective for JAK1 and/or JAK2 (e.g., ruxolitinib, baricitinib, momelotinib, filgotinib, pacritinib, INCB039110, INCB052793, INCB054707, CYT387, ABT494, AZD1480, XL019, CEP-33779, AZ 960, TG101209, and gandotinib). In some embodiments Pim inhibitors of the invention can be combined with inhibitors selective for JAK1 (e.g. INCB039110, INCB052793, INCB054707, and ABT494) such as those disclosed in e.g., WO 2010/135650, WO 2011/028685, WO 2011/112662, WO 2012/068450, WO 2012/068440, WO 2012/177606, WO 2013/036611, WO 2013/026025, WO 2014/138168, WO 2013/173720, WO 2015/021153, WO 2014/071031, WO 2014/106706, WO 2015/131031, WO 2015/168246, and WO 2015/184305. In some embodiments Pim inhibitors of the invention can be combined with inhibitors selective for JAK2 (e.g., pacritinib, AZD1480, XL019, CEP-33779, AZ 960, TG101209, and gandotinib).

In some embodiments Pim inhibitors of the invention can be combined with inhibitors selective for PI3K delta (e.g., idelalisib, INCB040093, INCB050465, and TGR 1202) such as those disclosed in e.g., WO 2011/0008487, WO 2011/075643, WO 2011/075630, WO 2011/163195, WO 2011/130342, WO 2012/087881, WO 2012/125629, WO 2012/135009, WO 2013/033569, WO2013/151930, WO 2014/134426, WO 2015/191677, and WO 2015/157257.

The Pim inhibitor of the present invention can further be used in combination with other methods of treating cancers, for example by chemotherapy, irradiation therapy, tumor-targeted therapy, adjuvant therapy, immunotherapy, or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, oncolytic virotherapy and immunomodulating small molecules, including thalidomide or JAK1/2 inhibitor and the like. For example, the salts of the invention can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments Pim inhibitors of the invention can be combined with cytarabine.

Other anti-cancer agent(s) include antibody therapeutics such as trastuzumab (Herceptin), antibodies to costimulatory molecules such as CTLA-4, 4-1BB, PD-1 and PD-L1, or antibodies to cytokines (IL-10, TGF-β, etc.). The Pim inhibitors presented herein can further be used in combination with one or more checkpoint inhibitors (e.g., inhibitors of an immune checkpoint molecule). Exemplary immune checkpoint inhibitors include inhibitors against immune checkpoint molecules such as CD27, CD28, CD40, CD122, CD96, CD73, CD47, OX40, GITR, CSF1R, JAK (e.g., JAK1 and/or JAK2), PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, immune checkpoint inhibitors include inhibitors against immune checkpoint molecules such as JAK1 and/or JAK2.

In some embodiments, immune checkpoint inhibitors include inhibitors against immune checkpoint molecules such as CD96.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MED14736, MPDL3280A (also known as RG7446), or MSB0010718C. In some embodiments, the anti-PD-L1 monoclonal antibody is MPDL3280A or MED14736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166. In some embodiments, the anti-GITR antibody is INCAGN01876.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383. In some embodiments, the anti-OX40 antibody is INCAGN01949.

In some embodiments, the inhibitor of an immune checkpoint molecule is an inhibitor of TIM3, e.g., an anti-TIM3 antibody.

In some embodiments Pim inhibitors of the invention can be combined with TIGIT inhibitors.

The Pim inhibitors of the present invention can be used in combination with one or more other anti-cancer agents including BET inhibitors (e.g., INCB054329, OTX015, and CPI-0610), LSD1 inhibitors (e.g., GSK2979552 and INCB059872), HDAC inhibitors (e.g., panobinostat, vorinostat, and entinostat), DNA methyl transferase inhibitors (e.g., azacitidine and decitabine), and other epigenetic modulators.

In some embodiments Pim inhibitors of the invention can be combined with BET inhibitors. In some embodiments Pim inhibitors of the invention can be combined with LSD1 inhibitors. In some embodiments Pim inhibitors of the invention can be combined with HDAC inhibitors. In some embodiments Pim inhibitors of the invention can be combined with DNA methyl transferase inhibitors.

The Pim inhibitors of the present invention can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

One or more anti-inflammatory agents, steroids, immunosuppressants, or therapeutic antibodies can also be combined with the salts of the invention.

When more than one pharmaceutical agent is administered to a patient, they can be administered simultaneously, sequentially, or in combination (e.g., for more than two agents).

Formulation, Dosage Forms and Administration

The salts of the invention can be administered in the form of a pharmaceutical composition. Thus the present disclosure provides a composition comprising the salts of the invention, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, a salt of the invention, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The salts of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; and sweetening agents and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least a salt described herein, and at least one pharmaceutically acceptable carrier. In some embodiments, the composition comprises a salt described herein, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at a salt described herein and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Solid oral dosage forms include, for example, tablets, capsules, and pills.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as for tablets, capsules, pills, or other oral dosage forms, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline® (petroleum jelly) and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications.

Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Example 1

Asymmetric Synthesis of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide Phosphoric Acid Salt

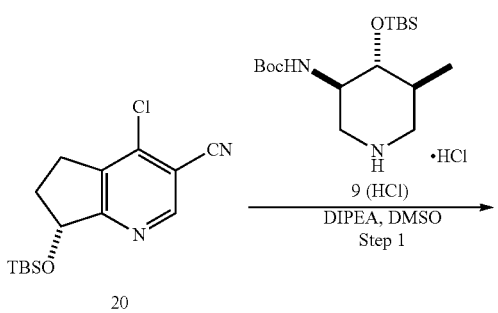

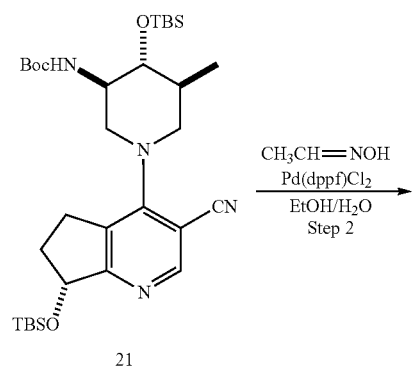

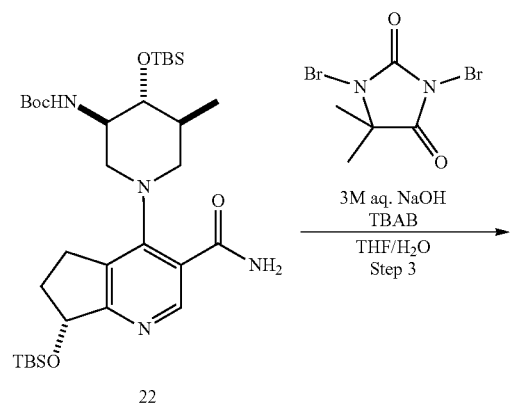

-continued

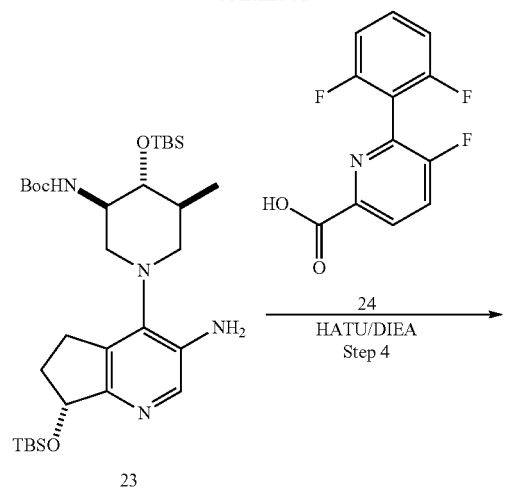

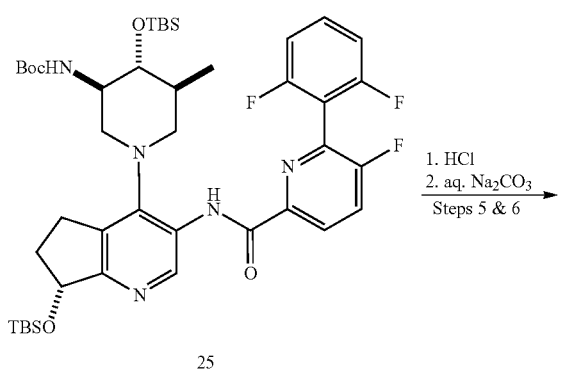

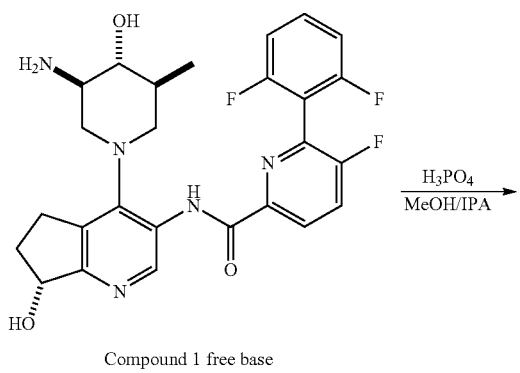

Compound 1 free base

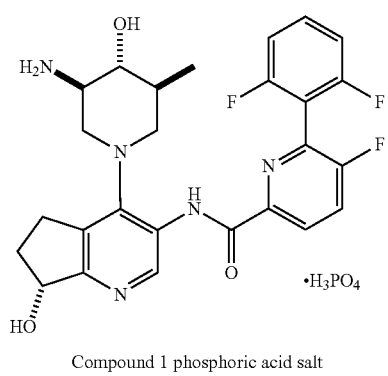

Compound 1 phosphoric acid salt

Step 1. Synthesis of tert-butyl [(3R,4R,5S)-4-{[tert-butyl(dimethyl)silyl]oxy}-1-((7R)-7-{[tert-butyl(dimethyl)silyl]oxy}-3-cyano-6,7-dihydro-5H-cyclopenta[b]pyridin-4-yl)-5-methylpiperidin-3-yl] carbamate (21)

To a stirred solution of (7R)-7-{[tert-butyl(dimethyl)silyl]oxy}-4-chloro-6,7-dihydro-5H-cyclopenta[b]pyridine-3-carbonitrile (20) (see Example 5, 54.0 g, 173 mmol) (99.2% pure by HPLC) in anhydrous dimethyl sulfoxide (DMSO, 162 mL) in a 1-L RBF was added tert-butyl ((3R,4R,5S)-4-{[tert-butyl(dimethyl)silyl]oxy}-5-methylpiperidin-3-yl) carbamate hydrochloride (9 (HCl)) (see U.S. Pat. Pub. No. 2014/0200227, para [0769], 70.0 g, 182.0 mmol, 1.05 equiv) and N,N-diisopropylethylamine (DIEA, 121 mL, 694 mmol, 4 equiv) at room temperature. The resulting reaction mixture was heated at 100° C. (oil bath) for 6 h. When LCMS and HPLC showed the reaction was complete (≥98.5% conversion), the reaction mixture was cooled to room temperature with a water bath, diluted with water (400 mL), extracted with t-butylmethylether (TBME) twice (700 and 400 mL). The organic layers were washed with brine (500 mL), dried over MgSO$_4$, filtered to remove the drying agent and concentrated in vacuo. The residue was purified by filtration chromatography (330 g silica gel column; elution with 5% EtOAc/hexanes over 4 min, followed by 25% EtOAc/hexanes over 6 min to give the desired product, tert-butyl [(3R,4R,5S)-4-{[tert-butyl(dimethyl)silyl]oxy}-1-((7R)-7-{[tert-butyl(dimethyl)silyl]oxy}-3-cyano-6,7-dihydro-5H-cyclopenta[b]pyridin-4-yl)-5-methylpiperidin-3-yl]carbamate (21) (100.6 g, 98.1% pure by HPLC, 92% yield) as an off-white solid. $^1$H NMR (400 MHz, DMSO-d$_6$) δ 8.48 (s, 1H), 6.75 (d, J=9.4 Hz, 1H), 5.01 (dd, J=6.9, 5.2 Hz, 1H), 3.61 (d, J=12.6 Hz, 1H), 3.52 (d, J=12.4 Hz, 1H), 3.48-3.36 (m, 1H), 3.23 (t, J=9.5 Hz, 1H), 3.02 (t, J=11.6 Hz, 2H), 2.84 (t, J=12.5 Hz, 1H), 2.74 (dt, J=15.2, 7.6 Hz, 1H), 2.32 (td, J=12.9, 8.0 Hz, 1H), 1.82 (ddd, J=13.3, 8.1, 4.3 Hz, 1H), 1.75-1.60 (m, 1H), 1.36 (s, 9H), 0.94 (d, J=6.5 Hz, 3H), 0.87 (s, 9H), 0.84 (s, 9H), 0.13 (s, 3H), 0.08 (s, 6H), 0.06 (s, 3H) ppm; LCMS (EI) m/z 617.4 (C$_{32}$H$_{57}$N$_4$O$_4$Si$_2$, (M+H)$^+$).

Step 2. Synthesis of tert-butyl ((3R,4R,5S)-1-((7R)-3-(aminocarbonyl)-7-{[tert-butyl(dimethyl)silyl]oxy}-6,7-dihydro-5H-cyclopenta[b]pyridin-4-yl)-4-{[tert-butyl(dimethyl)silyl]oxy}-5-methylpiperidin-3-yl) carbamate (22)

To a stirred solution of tert-butyl [(3R,4R,5S)-4-{[tert-butyl(dimethyl)silyl]oxy}-1-((7R)-7-{[tert-butyl(dimethyl)silyl]oxy}-3-cyano-6,7-dihydro-5H-cyclopenta[b]pyridin-4-yl)-5-methylpiperidin-3-yl]carbamate (21) (65.0 g, 105 mmol) in ethanol (195 mL) in a 2-L RBF was added [1,1′-bis(diphenylphosphino)ferrocene]dichloropalladium(II) (Pd(dppf)$_2$C$_2$ complexed with dichloromethane (1:1); 1.721 g, 2.107 mmol, 0.02 equiv), acetaldoxime (32.8 mL, 527 mmol, 5.0 equiv), and water (65 mL) at room temperature. The resulting reaction mixture was degassed and refilled with N$_2$ three times before being heated to reflux (oil bath; temperature at approximately 90° C.) for 6 h. An additional amount of acetaldoxime (32.8 mL, 527 mmol, 5.0 equiv) was added. The reaction mixture was then heated to reflux (oil bath; temperature at approximately 90° C.) for another 16 h. When LCMS and HPLC showed the reaction was complete (≥96.5% conversion), the hot reaction mixture was treated with water (390 mL) before being gradually cooled down to room temperature. The resulting slurry was stirred at room temperature for an additional 30 min before being collected by filtration. The wet cake was washed with water (3×100 mL) before re-slurry in a mixture of acetonitrile and water (400 mL; acetonitrile to water: 1 to 3 by volume). The solids were collected by filtration, washed with water (3×100 mL), and dried under house vacuum at room temperature overnight to afford the desired product, tert-butyl ((3R,4R,5S)-1-((7R)-3-(aminocarbonyl)-7-{[tert-butyl(dimethyl)silyl]oxy}-6,7-dihydro-5H-cyclopenta[b]pyridin-4-yl)-4-{[tert-butyl(dimethyl)silyl]oxy}-5-methylpiperidin-3-yl)carbamate (22), as a light brown powder, which was directly used in the subsequent reaction without further purification.

$^1$H NMR (400 MHz, DMSO-d$_6$) δ 8.16 (s, 1H), 7.84 (s, 1H), 7.46 (s, 1H), 6.66 (d, J=9.6 Hz, 1H), 5.01 (dd, J=6.8, 4.7 Hz, 1H), 3.48-3.36 (m, 1H), 3.23-3.07 (m, 3H), 3.01-2.88 (m, 1H), 2.82 (t, J=11.7 Hz, 1H), 2.74-2.58 (m, 2H), 2.35 (dt, J=12.3, 6.0 Hz, 1H), 1.84 (dt, J=13.1, 6.6 Hz, 1H), 1.72-1.56 (m, 1H), 1.35 (s, 9H), 0.90 (d, J=6.6 Hz, 3H), 0.87 (s, 9H), 0.84 (s, 9H), 0.14 (s, 3H), 0.08 (s, 3H), 0.07 (s, 3H), 0.06 (s, 3H); LCMS (EI) m/z 635.4 (C$_{32}$H$_{59}$N$_4$O$_5$Si$_2$, (M+H)$^+$).

Step 3. Synthesis of tert-butyl ((3R,4R,5S)-1-(3-amino-7-{[tert-butyl(dimethyl)silyl]oxy}-6,7-dihydro-5H-cyclopenta[b]pyridin-4-yl)-4-{[tert-butyl(dimethyl)silyl]oxy}-5-methylpiperidin-3-yl)carbamate (23)

To a stirred solution of tert-butyl ((3R,4R,5S)-1-((7R)-3-(aminocarbonyl)-7-{[tert-butyl(dimethyl)silyl]oxy}-6,7-dihydro-5H-cyclopenta[b]pyridin-4-yl)-4-{[tert-butyl(dimethyl)silyl]oxy}-5-methylpiperidin-3-yl)carbamate (22) (66.9 g, 105 mmol) in tetrahydrofuran (THF, 470.0 mL) in a 2-L 3 neck RBF at 0° C. was added tetra-N-butylammonium bromide (34.30 g, 105.4 mmol, 1.0 equiv) and a solution of 3.0 M sodium hydroxide in water (158.0 mL, 474.1 mmol, 4.5 equiv). 1,3-Dibromo-5,5-dimethylhydantoin (21.52 g, 73.75 mmol, 0.7 equiv) was then added portion-wise over 44 min to control the reaction temperature at 5 to 10° C. The resulting dark brown solution was stirred at 5 to 10° C. for an additional 20 min. When LCMS showed the reaction was complete, the reaction mixture was diluted with MTBE (100 mL), quenched with a 10% aqueous solution of Na$_2$S$_2$O$_3$ (300 mL) and water (200 mL). The two phases were separated, and the aqueous phase was extracted with MTBE (2×600 mL). The combined organic layers were washed with water (500 mL), dried over MgSO$_4$, filtered to remove the drying agent and concentrated in vacuo to afford the crude product as a brown foamy solid (63.7 g). The crude product was purified by filtration chromatography (330 g silica gel column; elution with 20% EtOAc/hexanes for 6 min, followed by 45% EtOAc/hexanes for 8 min, followed by recrystallization from heptane (180 mL) to afford the desired product, tert-butyl ((3R,4R,5S)-1-(3-amino-7-{[tert-butyl(dimethyl)silyl]oxy}-6,7-dihydro-5H-cyclopenta[b]pyridin-4-yl)-4-{[tert-butyl(dimethyl) silyl]oxy}-5-methylpiperidin-3-yl)carbamate (23) (46.2 g, 100.0% pure by HPLC, 72% yield for two steps) as an off-white solid.

$^1$H NMR (400 MHz, DMSO-d$_6$) δ 7.80 (s, 1H), 6.61 (d, J=9.7 Hz, 1H), 4.88 (dd, J=6.8, 3.6 Hz, 1H), 4.81 (s, 2H), 3.52 (td, J=9.8, 4.6 Hz, 1H), 3.14 (t, J=9.5 Hz, 1H), 3.04-2.84 (m, 3H), 2.85-2.68 (m, 2H), 2.48-2.42 (m, 1H), 2.23 (dq, J=13.2, 6.9 Hz, 1H), 1.79 (dq, J=12.6, 4.4 Hz, 2H), 1.35 (s, 9H), 0.89 (d, J=6.6 Hz, 3H), 0.85 (s, 18H), 0.10 (s, 3H), 0.08 (s, 3H), 0.06 (s, 3H), −0.00 (s, 3H); LCMS (EI) m/z 607.4 (C$_{31}$H$_{59}$N$_4$O$_4$Si$_2$, (M+H)$^+$).

Step 4. Synthesis of tert-butyl {(3R,4R,5S)-4-{[tert-butyl(dimethyl)silyl]oxy}-1-[(7R)-7-{[tert-butyl(dimethyl)silyl]oxy}-3-({[6-(2,6-difluorophenyl)-5-fluoropyridin-2-yl]carbonyl}amino)-6,7-dihydro-5H-cyclopenta[b]pyridin-4-yl]-5-methylpiperidin-3-yl}carbamate (25)

To a stirred solution of tert-butyl ((3R,4R,5S)-1-(3-amino-7-{[tert-butyl(dimethyl)silyl]oxy}-6,7-dihydro-5H-cyclopenta[b]pyridin-4-yl)-4-{[tert-butyl(dimethyl)silyl]oxy}-5-methylpiperidin-3-yl)carbamate (23) (100.0 g, 164.8 mmol) and 6-(2,6-difluorophenyl)-5-fluoropyridine-2-carboxylic acid (24) (see U.S. Pat. Pub. No. 2014/0200227, para [0625] 50.05 g, 197.7 mmol, 1.2 equiv) in anhydrous N,N-dimethylformamide (DMF, 320.0 mL) was added N,N-diisopropylethylamine (DIEA, 137.8 mL, 790.8 mmol, 4.8 equiv) at room temperature. After stirring at room temperature for 10 min, the reaction mixture was treated with N,N,N',N'-tetramethyl-O-(7-azabenzotriazol-1-yl)uronium hexafluorophosphate (HATU, 150.3 g, 395.4 mmol, 2.4 equiv) portion-wise to control the temperature at 15 to 30° C. The reaction mixture was then stirred at room temperature for 30 min. When LCMS and HPLC showed the reaction was complete, the reaction mixture was filtered into water (1300 mL) with stirring. The resulting slurry was stirred at room temperature for an additional 30 min. The solids were collected by filtration and washed with a mixture of 50% acetonitrile and water (50% by volume; 2×200 mL). The wet solid was then treated with acetonitrile (420 mL) and the resulting slurry was heated at 70° C. until a clear solution is generated. Water (320 mL) was added slowly to the solution at 70° C. and the resulting mixture was gradually cooled to room temperature and stirred at room temperature for 30 min. The solids were collected by filtration, washed with a mixture of acetonitrile and water (50% by volume; 320 mL) and dried in a vacuum oven at 50° C. for overnight to afford the desired product, tert-butyl {(3R,4R,5S)-4-{[tert-butyl(dimethyl)silyl]oxy}-1-[(7R)-7-{[tert-butyl(dimethyl)silyl]oxy}-3-({[6-(2,6-difluorophenyl)-5-fluoropyridin-2-yl]carbonyl}amino)-6,7-dihydro-5H-cyclopenta[b]pyridin-4-yl]-5-methylpiperidin-3-yl}carbamate (25) (131.8 g, 99.7% pure by HPLC, 95% yield) as white powder.

$^1$H NMR (400 MHz, DMSO-d$_6$) δ 10.39 (s, 1H), 8.95 (s, 1H), 8.36 (dd, J=8.7, 4.0 Hz, 1H), 8.19 (t, J=8.9 Hz, 1H), 7.67-7.55 (m, 1H), 7.27 (t, J=8.5 Hz, 3H), 6.46 (d, J=9.6 Hz, 1H), 5.00 (dd, J=6.8, 4.2 Hz, 1H), 3.40 (dd, J=9.3, 5.9 Hz, 1H), 3.05 (t, J=9.4 Hz, 2H), 2.93 (t, J=10.8 Hz, 4H), 2.82 (dt, J=15.8, 8.1 Hz, 1H), 2.56 (t, J=11.7 Hz, 1H), 2.40-2.26 (m, 1H), 1.92-1.79 (m, 1H), 1.54 (s, OH), 1.32 (s, 9H), 0.87 (s, 11H), 0.84 (s, 9H), 0.71 (d, J=6.5 Hz, 4H), 0.14 (s, 4H), 0.07 (s, 3H), 0.04 (s, 4H), 0.01 (s, 3H); LCMS (EI) m/z 842.4 (C$_{43}$H$_{63}$F$_3$N$_5$O$_5$Si$_2$, (M+H)$^+$).

Step 5. Synthesis of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide Dihydrochloric Acid (Compound 1 Dihydrochloric Acid Salt)

A solution of 4.0 M hydrogen chloride in 1,4-dioxane (13.9 L, 55600 mmol, 15.0 equiv) was added into a slurry of tert-butyl {(3R,4R,5S)-4-{[tert-butyl(dimethyl)silyl]oxy}-

1-[(7R)-7-{[tert-butyl(dimethyl)silyl]oxy}-3-({[6-(2,6-difluorophenyl)-5-fluoropyridin-2-yl]carbonyl}amino)-6,7-dihydro-5H-cyclopenta[b]pyridin-4-yl]-5-methylpiperidin-3-yl}carbamate (25) (3121.0 g, 3706.0 mmol) in methanol (19.5 L) at room temperature. The internal temperature rose from 17.3 to 36.8° C. during addition of the HCL solution in 1,4-dioxane. The resulting light yellow solution was stirred at room temperature for 22 h and solids (2 HCl salt) started to precipitate out of the solution within 2 h. When LCMS and HPLC indicated the reaction was complete, the solids were collected by filtration, washed with heptane (5 L), and dried on the filter under vacuum overnight to afford the desired product, N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide dihydrochloride (Compound 1 dihydrochloric acid salt) (2150.0 g, 99.1% pure by HPLC, 98% yield) as white powder. $^1$H NMR (400 MHz, DMSO-$d_6$) δ 10.57 (s, 1H), 8.57 (s, 3H), 8.36 (dd, J=8.7, 4.1 Hz, 1H), 8.22 (t, J=8.8 Hz, 1H), 7.69 (ddd, J=15.1, 8.5, 6.7 Hz, 1H), 7.34 (t, J=8.1 Hz, 2H), 5.27 (t, J=7.0 Hz, 1H), 4.02 (d, J=11.1 Hz, 1H), 3.44 (d, J=11.3 Hz, 1H), 3.29 (t, J=12.2 Hz, 1H), 3.13 (q, J=8.5, 7.4 Hz, 2H), 3.09-2.97 (m, 2H), 2.77 (t, J=12.3 Hz, 1H), 2.56-2.50 (m, 1H), 1.95 (dq, J=14.9, 7.7, 7.2 Hz, 1H), 1.66-1.50 (m, 1H), 0.70 (d, J=6.5 Hz, 3H); LCMS (EI) m/z 514.2 ($C_{26}H_{27}F_3N_5O_3$, (M+H)$^+$).

Step 6. Synthesis of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 Free Base)

A 200 L glass reactor was assembled with overhead stirring, condenser, thermocouple, addition funnel, and a nitrogen inlet and the apparatus was purged with nitrogen. Sodium carbonate (18,264 g) and potable water (86.2 L) were charged to the reactor and stirred for about 50 minutes until a solution was obtained. Methylene chloride (107.8 L) was charged to the reactor. N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide dihydrochloride (Compound 1 dihydrochloric acid salt) (4300 g) was charged over about 27 minutes to the reactor while maintaining the temperature at about 27° C. and the reaction mixture was stirred at about 23° C. for about 22 hours until a clear solution was obtained. The phases were separated, and the aqueous phase was extracted with methylene chloride (26.9 L). The combined organic phases were washed twice with potable water (26.9 L per wash) and concentrated under reduced pressure at about 54° C. to afford the desired product, N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base, 3838 g), as a light yellow solid, which was directly used in the subsequent reaction without further purification. LCMS (EI) m/z 514.2 ($C_{26}H_{27}F_3N_5O_3$, (M+H)$^+$).

Step 7. Synthesis of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide Phosphoric Acid (Compound 1 Phosphoric Acid Salt)

A 100 L glass reactor was assembled with overhead stirring, condenser, thermocouple, addition funnel, and a nitrogen inlet and the apparatus was purged with nitrogen. Separately, a phosphoric acid solution was prepared by thoroughly mixing an aqueous solution of 85% $H_3PO_4$ (980 g) and 2-propanol (IPA, 5.7 L) at room temperature. The phosphoric acid solution was polish filtered through an in-line filter. Separately, methanol (19.0 L), USP purified water (1.9 L), and 2-propanol were polish filtered through an in-line filter. Filtered methanol (19.0 L), N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 free base) (3800 g), filtered USP purified water (1.9 L), and filtered 2-propanol (15.2 L) were charged sequentially to the reactor. The reaction mixture was heated to about 56° C. Filtered phosphoric acid solution (5.8 L) was charged to the reactor over about 45 minutes while maintaining the temperature at about 59° C. The container was rinsed into the reaction mixture with filtered 2-propanol (5.8 L) while maintaining the temperature at about 62° C. Filtered 2-propanol (15.2 L) was charged while maintaining the temperature at about 58° C., and the reaction mixture was stirred at about 57° C. for about 1.5 hours. The reaction mixture was cooled to about 26° C. and stirred at about 17° C. for about 3.5 hours. The reaction mixture was filtered and the filter cake was washed sequentially with filtered 2-propanol (22.8 L) and filtered heptane (prepared separately by polish filtering 22.8 L of heptane through an in-line filter). The product was dried on the filter and then dried under reduced pressure at 20-54° C. to afford the desired product, N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt (Compound 1 phosphoric acid salt) (3952 g, >99.0% pure by HPLC, 87.3% yield) as a white to off-white crystalline solid.

$^1$H NMR (400 MHz, DMSO-$d_6$) δ 10.43 (s, 1H), 9.25 (s, 1H), 8.38 (dd, J=8.7, 4.1 Hz, 1H), 8.20 (t, J=8.8 Hz, 1H), 7.66 (ddd, J=15.2, 8.4, 6.7 Hz, 1H), 7.32 (t, J=8.6 Hz, 2H), 7.19 (s, 2H), 4.82 (dd, J=6.9, 4.5 Hz, 1H), 3.22 (d, J=6.9 Hz, 1H), 3.18-2.99 (m, 3H), 2.87 (d, J=8.0 Hz, 2H), 2.79-2.67 (m, 1H), 2.59 (t, J=11.5 Hz, 1H), 2.27 (dt, J=13.5, 6.6 Hz, 1H), 1.92-1.74 (m, 1H), 1.58-1.39 (m, 1H), 0.70 (d, J=6.5 Hz, 3H) ppm; $^{13}$C NMR (100 MHz, DMSO-$d_6$) δ 163.1, 160.5, 159.5 (dd, $J_{CF}$=249.4, 6.6 Hz), 159.0 (d, $J_{CF}$=261.8 Hz), 146.0 (d, $J_{CF}$=4.2), 144.6, 136.1 ($J_{CF}$=18.6), 140.8, 132.8 (t, $J_{CF}$=10.6 Hz), 130.6, 128.5, 126.2 (d, $J_{CF}$=20.5), 125.4 (d, $J_{CF}$=6.4), 112.4 (d, $J_{CF}$=20.8 Hz), 110.7 (td, $J_{CF}$=19.5, 3.6 Hz), 74.9, 72.8, 55.7, 54.0, 52.4, 37.7, 33.1, 26.9, 14.4 ppm; $^{19}$F NMR (376 MHz, DMSO-$d_6$) δ −117.26 (m, 1F), −113.77 (m, 2F) ppm; LCMS (EI) m/z 514.2 ($C_{26}H_{27}F_3N_5O_3$, (M+H)$^+$).

Results of quantitative elemental microanalysis for carbon, hydrogen, and nitrogen on Compound 1 phosphoric acid salt are in agreement with the proposed empirical formula ($C_{26}H_{29}F_3N_5O_7P$). Anal. Calcd for $C_{26}H_{29}F_3N_5O_7P$: C, 51.07; H, 4.78; N, 11.45. Found: C, 51.16; H, 4.70; N, 11.56.

Example 2

X-Ray Powder Diffraction (XRPD) of Compound 1 Phosphoric Acid Salt Form I

Form I of crystalline N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt, (see Example 1, Step 7) was characterized by XRPD. The X-Ray Power Diffraction (XRPD) was obtained from Rigaku Mini-Flex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min. The XRPD pattern is shown in FIG. 1 and XRPD data is provided in Table 1.

TABLE 1

| XRPD Data Form I | | |
|---|---|---|
| 2-Theta (°) | Height | H % |
| 4.6 | 1078 | 100 |
| 8.7 | 52 | 4.8 |
| 9.4 | 377 | 35 |
| 12.5 | 160 | 14.8 |
| 13.1 | 926 | 85.9 |
| 14.0 | 62 | 5.8 |
| 16.2 | 937 | 86.9 |
| 17.4 | 534 | 49.6 |
| 17.9 | 717 | 66.5 |
| 18.8 | 708 | 65.7 |
| 19.4 | 616 | 57.1 |
| 20.3 | 199 | 18.5 |
| 21.1 | 960 | 89.1 |
| 22.3 | 294 | 27.3 |
| 23.0 | 700 | 65 |
| 24.8 | 746 | 69.3 |
| 25.2 | 315 | 29.2 |
| 25.8 | 109 | 10.1 |
| 26.4 | 364 | 33.8 |
| 27.6 | 165 | 15.3 |
| 28.9 | 84 | 7.8 |
| 29.4 | 92 | 8.6 |
| 30.2 | 136 | 12.6 |
| 30.7 | 77 | 7.2 |
| 33.3 | 99 | 9.2 |
| 34.1 | 165 | 15.3 |
| 34.9 | 168 | 15.5 |
| 35.5 | 199 | 18.5 |
| 36.0 | 56 | 5.2 |
| 37.0 | 49 | 4.5 |
| 37.6 | 64 | 5.9 |
| 38.2 | 246 | 22.8 |
| 38.6 | 80 | 7.4 |
| 39.8 | 67 | 6.3 |
| 40.1 | 64 | 5.9 |
| 40.9 | 66 | 6.2 |
| 41.7 | 119 | 11 |
| 42.1 | 84 | 7.8 |
| 43.7 | 82 | 7.6 |
| 43.9 | 43 | 4 |

Example 3

Differential Scanning Calorimetry (DSC) of Compound 1 Phosphoric Acid Salt (Form I)

The crystalline solid, N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt, (see Example 1, Step 7) was characterized by DSC. The DSC was obtained from TA Instruments Differential Scanning Calorimetry, Model Q200 with autosampler. The DSC instrument conditions were as follows: 30-350° C. at 10° C./min; Tzero aluminum sample pan and lid; and nitrogen gas flow at 50 mL/min. The DSC thermogram is shown in FIG. 2. The DSC thermogram revealed a major endothermal event (believed to be a melting/decomposition) at an onset temperature of 238.8° C. with a peak temperature of 247.1° C. and a small endothermal event at an onset temperature of 193.1° C. with a peak temperature at 198.4° C. Multiple lots of Form I were characterized by DSC, each having a thermogram with a major endothermal peak occurring within the range of 249.7 to 254.7° C.

Example 4

Thermogravimetric Analysis (TGA) of Compound 1 Phosphoric Acid Salt (Form I)

The crystalline solid, N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide phosphoric acid salt, (see Example 1, Step 7) was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan. The TGA thermogram is shown in FIG. 3. A weight loss of about 2% below 200° C. was observed and believed to be associated with loss of moisture and residual solvents. Karl-Fischer analysis of various synthetic lots of Form I was conducted, each experiment revealing a water content within the range of 1.40-1.50% indicating that Form I may be a hydrate, such as a hemihydrate.

Example 5

Asymmetric Synthesis of (7R)-7-{[tert-Butyl(dimethyl)silyl]oxy}-4-chloro-6,7-dihydro-5H-cyclopenta[b]pyridine-3-carbonitrile (20)

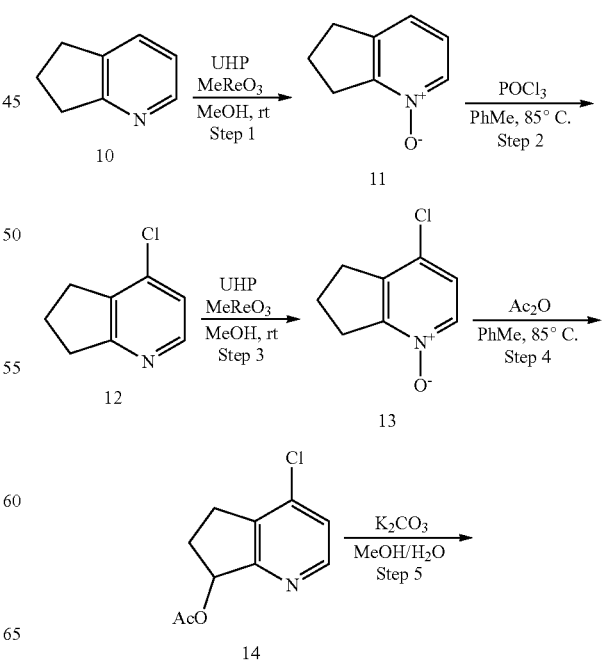

-continued

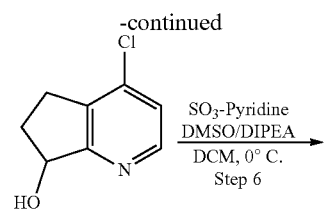
15

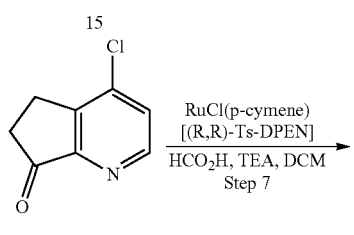
16

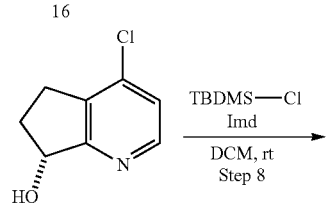
17

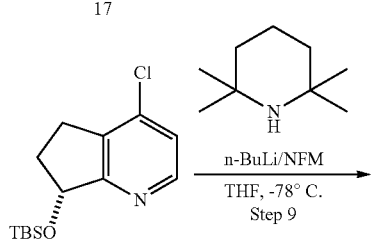
18

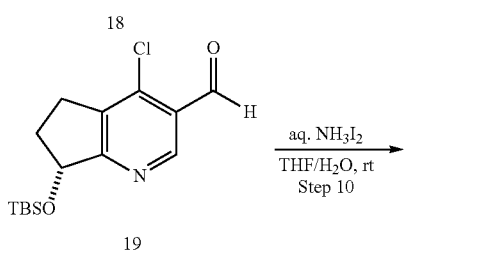
19

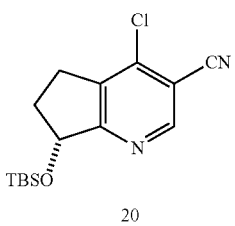 [SMILES: CC(C)(C)[Si](C)(C)O[C@@H]1CCc2c1ncc(C#N)c2Cl]
20

Step 1. 6,7-Dihydro-5H-cyclopenta[b]pyridine 1-oxide (11)

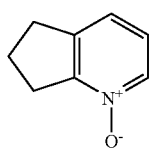

To a mixture of 6,7-dihydro-5H-cyclopenta[b]pyridine (10) (10.0 g, 83.9 mmol) in methanol (50 mL) was added urea hydrogen peroxide adduct (UHP, 24 g, 250 mmol, 3.0 equiv.) and methyltrioxorhenium(VII) (80 mg, 0.3 mmol, 0.0036 equiv.) at room temperature. The resulting mixture was stirred at room temperature overnight before being concentrated under reduced pressure to remove methanol. After no more distillate was observed, methylene chloride (100 mL) was added and the concentration was continued. The resulting residue was treated with methylene chloride (100 mL) and stirred at room temperature for 10 minutes. The solids were filtered and extracted with methylene chloride for 3 times (3×50 mL). The combined filtrates were dried with anhydrous sodium sulfate ($Na_2SO_4$) and sodium bisulfite ($NaHSO_3$) before being filtered through a silica gel pad ($SiO_2$). The pad was rinsed with 10% MeOH in $CH_2CH_2$ (100 mL) for 3 times. The combined filtrates were concentrated to give the desired product, 6,7-dihydro-5H-cyclopenta[b]pyridine 1-oxide (11, 11.5 g, 99% yield) as off-white solid, which was used in the subsequent reaction without further purification. For 11: $^1$HNMR (300 MHz, $CDCl_3$) δ 8.05 (d, J=6.0 Hz, 1H), 7.08 (m, 2H), 3.15. (t, J=6.0 Hz, 2H), 3.00. (t, J=6.0 Hz, 2H), 2.16 (m, 2H) ppm; LCMS (EI) m/z 136 ($C_8H_9NO$, $(M+H)^+$).

Step 2. 4-Chloro-6,7-dihydro-5H-cyclopenta[b]pyridine (12)

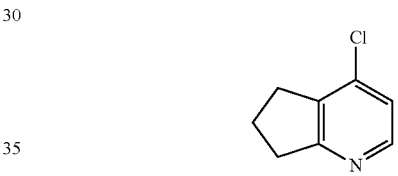

6,7-Dihydro-5H-cyclopenta[b]pyridine 1-oxide (11, 12.0 g, 84.3 mmol) was slowly added into phosphoryl chloride ($POCl_3$, 24 mL, 250 mmol, 3.0 equiv) and toluene (48 mL) at 80-85° C. (internal temperature) with about 0.2 g per portion over 2 hours. After the completion of addition, the reaction mixture was continued to stir at 80-85° C. (internal temperature) for 3 hours. The excess amount of $POCl_3$ and toluene was removed under reduced pressure at 60° C. The resulting residue was then poured to a cooled mixture of ice (50 g) and the saturated aqueous sodium carbonate solution ($Na_2CO_3$, 50 mL). The pH of the mixture was adjusted to 8 using 25% aqueous sodium hydroxide solution (NaOH, about 30 mL). The mixture was then extracted with methylene chloride (3×100 mL). The combined organic extracts were dried over anhydrous $Na_2SO_4$ and filtered through a pad of silica gel ($SiO_2$, 36 g) and charcoal (6 g, on the top of silica gel). The pad was rinsed with ethyl acetate (4×100 mL) until no desired product came out from the silica gel pad. The combined filtrates were then concentrated under reduced pressure to give the crude desired product (12, 10.93 g). To the mixture of crude 4-chloro-6,7-dihydro-5H-cyclopenta[b]pyridine (12, 10.7 g, 69.6 mmol) in THF (50 mL) was added 3-chlorobenzoic acid (11 g, 73 mmol) at room temperature. The mixture was then stirred at room temperature until 3-chlorobenzoic acid was dissolved. The mixture was concentrated under reduced pressure to generate the crude salt as solids, which was treated with hexanes (32 mL). The resulting suspension was stirred at room temperature for 10 minutes. The solids were collected by filtration, washed with hexanes (2×32 mL). More solids were collected from the filtrates. The combined wet solids (about 18 g) were dissolved in methylene chloride (100 mL) and treated with the saturated aqueous $Na_2CO_3$ solution (2×20 mL). The aqueous layers were back extracted with methylene chloride (50 mL). The combined organic extracts were dried with anhydrous $Na_2SO_4$, filtered and concentrated to give the purified desired product, 4-chloro-6,7-dihydro-5H-cyclopenta[b]pyridine (12, 7.1 g), as dark oil. For 12: $^1$HNMR (300 MHz, $CDCl_3$) δ 8.20 (d, J=3.0 Hz, 1H), 7.02 (d, J=3.0 Hz, 1H), 3.06. (t, J=6.0 Hz, 2H), 2.98. (t, J=6.0 Hz, 2H), 2.12 (m, 2H) ppm; LCMS (EI) m/z 154/156 ($C_8H_8ClN$, $(M+H)^+$).

Step 3. 4-Chloro-6,7-dihydro-5H-cyclopenta[b]pyridine 1-oxide (13)

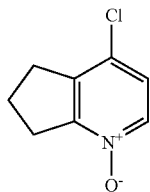

To a mixture of 4-chloro-6,7-dihydro-5H-cyclopenta[b]pyridine (12, 100.0 g, 618.4 mmol) in methanol (500 mL) was added urea hydrogen peroxide adduct (UHP, 1.5 eq, 87.3 g, 928 mmol, 1.5 equiv) and methyltrioxorhenium(VII) (925 mg, 3.71 mmol, 0.006 equiv) at room temperature. The resulting mixture was stirred at room temperature for 3 hours. The reaction mixture was concentrated under reduced pressure to remove methanol. Methylene chloride (500 mL) was added and the concentration was continued. The resulting residue was treated with methylene chloride (500 mL) and the resulting mixture was stirred for 30 minutes. The solids were filtered and extracted with methylene chloride for (4×500 mL). The combined filtrates were dried with anhydrous sodium sulfate ($Na_2SO_4$) and sodium bisulfite ($NaHSO_3$). The mixture was then filtered through a pad of silica gel ($SiO_2$, 180 g) and the activated charcoal (10 g). The pad was rinsed with 10% MeOH in $CH_2CH_2$ (500 mL) 3 times. The combined filtrates were concentrated under reduced pressure to give the desired product, 4-chloro-6,7-dihydro-5H-cyclopenta[b]pyridine 1-oxide (13, 104 g), as off-white solids. For 13: $^1$HNMR (300 MHz, DMSO-$d_6$) δ 8.04 (d, J=6.0 Hz, 1H), 7.34 (d, J=6.0 Hz, 1H), 2.98. (m, 4H), 2.08 (m, 2H) ppm; LCMS (EI) m/z 170/172 ($C_8H_8ClNO$, $(M+H)^+$).

Step 4. 4-Chloro-6,7-dihydro-5H-cyclopenta[b]pyridin-7-yl acetate (14)

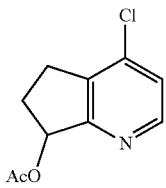 [SMILES: CC(=O)OC1CCc2c(Cl)ccnc21]

4-Chloro-6,7-dihydro-5H-cyclopenta[b]pyridine 1-oxide (13) (65.0 g, 340 mmol) was added to the mixture of acetic anhydride ($Ac_2O$, 98 mL, 1000 mmol) and toluene (325 mL) in portions (6 g per portion) at 80-85° C. over 1 hour. After the addition was complete, the resulting mixture was stirred at 80-85° C. for 3 hours. When the reaction completion was indicated by LCMS and/or HPLC, the reaction mixture was concentrated under reduced pressure to remove acetic anhydride and toluene. The crude desired product, 4-chloro-6,7-dihydro-5H-cyclopenta[b]pyridin-7-yl acetate (14), obtained was used directly in the subsequent reaction without further purification. For 14: $^1$HNMR (300 MHz, DMSO-$d_6$) δ 8.38 (d, J=6.0 Hz, 1H), 7.21 (d, J=6.0 Hz, 1H), 6.14. (m, 1H), 3.08 (m, 1H), 2.93 (m, 1H), 2.64 (m, 1H), 2.10 (s, 3H), 2.07 (m, 1H) ppm; LCMS (EI) m/z 212/214 ($C_{10}H_{10}ClNO_2$, $(M+H)^+$).

Step 5. 4-Chloro-6,7-dihydro-5H-cyclopenta[b]pyridin-7-ol (15)

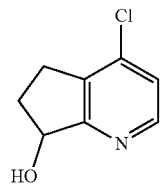

To a mixture of 4-chloro-6,7-dihydro-5H-cyclopenta[b]pyridin-7-yl acetate (14, 73 g, 340 mmol, telescoped from the last step) in MeOH (130 mL) and water (130 mL) was added potassium carbonate ($K_2CO_3$, 130 g, 920 mmol) at 0° C. The resulting mixture was gradually warmed to room temperature and stirred at room temperature for 4 hours. The reaction mixture was then concentrated under reduced pressure to remove methanol. The precipitated solids were collected by filtration, washed with water (3×100 mL), and dried to give the first portion of the crude product (15). The aqueous layers were extracted with DCM (3×300 mL). The combined organic extracts were dried over anhydrous $Na_2SO_4$, filtered and concentrated to give the second portion of the crude product (15). The crude desired product, 4-chloro-6,7-dihydro-5H-cyclopenta[b]pyridin-7-ol (15, 61.9 g, 93% yield for 2 steps) obtained from two portions as dark brown oil, was directly used in the subsequent reaction without further purification. For 15: $^1$HNMR (300 MHz, DMSO-$d_6$) δ 8.34 (d, J=3.0 Hz, 1H), 7.18 (d, J=3.0 Hz, 1H), 5.26. (t, J=3.0 Hz, 1H), 3.08 (m, 1H), 2.86 (m, 1H), 2.60 (m, 1H), 2.09 (m, 1H) ppm; LCMS (EI) m/z 170/172 ($C_8H_8ClNO$, $(M+H)^+$).

Step 6. 4-Chloro-5H-cyclopenta[b]pyridin-7(6H)-one (16)

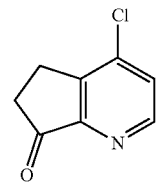 [SMILES: O=C1CCc2c(Cl)ccnc21]

To the solution of 4-chloro-6,7-dihydro-5H-cyclopenta[b]pyridin-7-ol (15, 110.3 g, 650.32 mmol) in methylene chloride (800 mL) was added N,N-diisopropylethylamine (339.5 g, 2627.0 mmol) at room temperature. After the mixture was cooled to 0° C., pyridine-sulfur trioxide (1:1) (200.0 g, 1256.6 mmol) in dimethyl sulfoxide (DMSO, 800 g) was added dropwise over 35 minutes and the resulting mixture was stirred at 0° C. for 1 hour. The reaction progress was monitored by HPLC and about 30% of starting material 15 was left. Additional amounts of pyridine-sulfur trioxide (1:1) (138 g, 866.8 mmol) and N,N-diisopropylethylamine (79.8 g, 617 mmols) were added, and the reaction mixture was stirred under an ice bath for another 2 hours. Water (1000 mL) was added to the reaction mixture, and the resulting mixture was concentrated under reduced pressure to remove methylene chloride. The resulting residue was carefully poured into saturated aqueous NaHCO$_3$ (2000 mL). The solids were collected by filtration, washed with water (2×200 mL), and dried to give the first portion of the crude desired product (16). The aqueous filtrate was extracted with methylene chloride (2×200 mL). The combined organic extracts were dried over anhydrous Na$_2$SO$_4$, filtered and concentrated to give the second portion of the crude desired product (16). The combined crude desired product was purified by silica gel flash chromatography (SiO$_2$, eluted with 0 to 50% ethyl acetate/hexane) to provide the desired product, 4-chloro-5H-cyclopenta[b]pyridin-7 (6H)-one (16, 87 g, 80% yield), as yellow to brown oil, which solidified upon standing in vacuum. For 16: $^1$HNMR (300 MHz, DMSO-d$_6$) δ 8.68 (d, J=6.0 Hz, 1H), 7.48 (d, J=6.0 Hz, 1H), 3.18 (m, 2H), 2.81 (m, 2H) ppm; LCMS (EI) m/z 168/170 (C$_8$H$_6$ClNO, (M+H)$^+$).

Step 7. (R)-4-Chloro-6,7-dihydro-5H-cyclopenta[b]pyridin-7-ol (17)

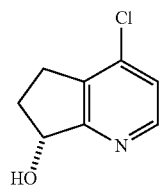

To the solution of 4-chloro-5H-cyclopenta[b]pyridin-7 (6H)-one (16, 138.0 g, 823.4 mmol) and triethylamine (TEA, 573.8 mL, 4117 mmol) in methylene chloride (1100 mL) was added RuCl(p-cymene)[(R,R)-Ts-DPEN] (1.31 g, 2.06 mmol) at room temperature. The resulting mixture was degased, cooled down to 5-10° C., and stirred at 5-10° C. under nitrogen. Formic acid (155.3 mL, 4117 mmol) was then added slowly (internal temperature) to the reaction mixture at 7-14° C. After the addition, the reaction mixture gradually warmed to room temperature and stirred at room temperature for 22 hours. When LC/MS and HPLC showed the reaction was complete, the reaction mixture was quenched with the saturated aqueous sodium bicarbonate (NaHCO$_3$) solution (1000 mL) and water (1500 mL). The two layers were separated, and the aqueous layer was extracted with methylene chloride (3×500 mL). The organic layers were combined, dried over anhydrous Na$_2$SO$_4$, filtered and concentrated to give the crude desired product, (R)-4-chloro-6,7-dihydro-5H-cyclopenta[b]pyridin-7-ol (17, assumed 100% yield) as yellow to brown oil, which was directly used for the subsequent reaction without further purification. For 17: $^1$HNMR (300 MHz, DMSO-d$_6$) δ 8.33 (d, J=6.0 Hz, 1H), 7.19 (d, J=6.0 Hz, 1H), 5.27 (m, 1H), 3.08 (m, 1H), 2.86 (m, 1H), 2.57 (m, 1H), 2.10 (m, 1H) ppm; LCMS (EI) m/z 170/172 (C$_8$H$_8$ClNO, (M+H)$^+$).

Step 8. (R)-7-(tert-Butyldimethylsilyloxy)-4-chloro-6,7-dihydro-5H-cyclopenta[b]pyridine (18)

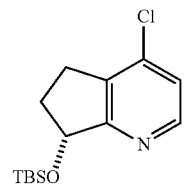 [SMILES: CC(C)(C)[Si](C)(C)O[C@@H]1CCc2c(Cl)ccnc21]

To the stirred solution of (R)-4-chloro-6,7-dihydro-5H-cyclopenta[b]pyridin-7-ol (17, 172.25 g, 1015.6 mmol) in anhydrous methylene chloride (2500 mL) was added tert-butyldimethylsilyl chloride (172.25 g, 1015.6 mmol) and 1H-imidazole (101.3 g, 1472 mmol) at 0-5° C. The resulting reaction mixture was stirred at room temperature for overnight. When LC/MS and HPLC showed the reaction was complete, the reaction mixture was quenched with water (1000 mL). The two layers were separated, and the aqueous layer was extracted with methylene chloride (3×500 mL). The combined organic layers were dried over anhydrous Na$_2$SO$_4$, filtered and concentrated to give the crude desired product (18). The purification of the crude product on silica gel chromatography (SiO$_2$, eluting with 0-10% ethyl acetate in hexanes) provided the desired product, (R)-7-(tert-butyldimethylsilyloxy)-4-chloro-6,7-dihydro-5H-cyclopenta[b]pyridine (18, 253.0 g, 87.8% yield for 2 steps) as yellow to brown oil. For 18: $^1$HNMR (300 MHz, DMSO-d$_6$) δ 8.36 (d, J=3.0 Hz, 1H), 7.13 (d, J=3.0 Hz, 1H), 5.21 (m, 1H), 3.08 (m, 1H), 2.81 (m, 1H), 2.43 (m, 1H), 2.05 (m, 1H), 0.93 (s, 9H), 0.22 (s, 3H), 0.16 (s, 3H) ppm; LCMS (EI) m/z 284/286 (C$_{14}$H$_{22}$ClNOSi, (M+H)$^+$).

Step 9. (R)-7-(tert-Butyldimethylsilyloxy)-4-chloro-6,7-dihydro-5H-cyclopenta[b]pyridine-3-carbaldehyde (19)

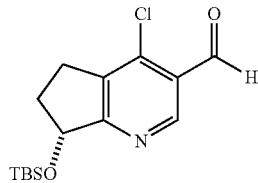 [SMILES: CC(C)(C)[Si](C)(C)O[C@@H]1CCc2c1ncc(C=O)c2Cl]

To the stirred solution of 2,2,6,6-tetramethyl-piperidine (63.0 g, 446 mmol) in anhydrous tetrahydrofuran (THF, 680 mL) at −24° C. to −50° C. was added a solution of 2.5 M n-butyl lithium in hexane (180 mL, 450 mmol). The resulting mixture was warmed up to >−32° C. and stirred at −32° C. to 0° C. for 30 minutes and then cooled to −78° C. (external bath). (R)-7-(tert-butyldimethylsilyloxy)-4-chloro-6,7-dihydro-5H-cyclopenta[b]pyridine (18, 106.0 g, 373 mmol) in anhydrous tetrahydrofuran (380 mL) was added dropwise to the above cooled mixture at −74° C. to −76° C. (internal temperature). After the resulting dark brown solution was stirred at −74° C. (internal temperature) for 90 minutes, anhydrous N,N-dimethylformamide (DMF, 130 g, 1129 mmol) was added and the internal temperature was maintained at −76° C. to −70° C. during addition. The resulting reaction mixture was continued to stir at −74° C. to −72° C. for 2 hours before being quenched with 1 N aqueous HCl solution (500 mL) and water (500 mL). The two phases were separated, and the aqueous phase was extracted with MTBE (2×250 mL). The combined organic phases were washed with brine (2×250 mL) and concentrated under reduced pressure to give the crude product (19). The purification of the crude product on silica gel chromatography (SiO$_2$, eluting with 0-8% ethyl acetate in hexane) provided the desired product, (R)-7-(tert-butyldimethylsilyloxy)-4-chloro-6,7-dihydro-5H-cyclopenta[b]pyridine-3-carbaldehyde (19, 110.7 g, 94% yield), as yellow to brown oil. For 19: $^1$HNMR (300 MHz, CDCl$_3$) δ 10.4 (s, 1H), 8.91 (s, 1H), 5.22 (m, 1H), 3.10 (m, 1H), 2.87 (m, 1H), 2.48 (m, 1H), 2.09 (m, 1H), 0.92 (s, 9H), 0.21 (s, 3H), 0.16 (s, 3H) ppm; LCMS (EI) m/z 312/314 (C$_{15}$H$_{22}$ClNO$_2$Si, (M+H)$^+$).

Step 10. (R)-7-(tert-Butyldimethylsilyloxy)-4-chloro-6,7-dihydro-5H-cyclopenta[b]pyridine-3-carbonitrile (20)

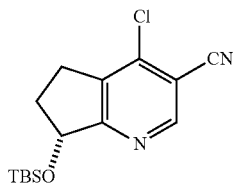 [SMILES: CC(C)(C)[Si](C)(C)O[C@@H]1CCc2c1ncc(C#N)c2Cl]

To a stirred solution of (R)-7-(tert-butyldimethylsilyloxy)-4-chloro-6,7-dihydro-5H-cyclopenta[b]pyridine-3-carbaldehyde (19, 91.3 g, 292 mmol) in tetrahydrofuran (THF, 700 mL) at room temperature was added a solution of 14.8 M ammonia in water (350 mL, 5950 mmol) and iodine (I$_2$, 80.0 g, 315 mmol) under an ice-water bath (the internal temperature was controlled at 16° C. to 22° C.). The resulting reaction mixture was stirred at room temperature for 3 hours before being quenched with a 10% Na$_2$S$_2$O$_3$ aqueous solution (200 mL). The mixture was extracted with ethyl acetate (2 500 mL). The combined organic extracts were washed with water (100 mL), dried over anhydrous Na$_2$SO$_4$, filtered and concentrated under reduced pressure to give the desired product, (R)-7-(tert-butyldimethylsilyloxy)-4-chloro-6,7-dihydro-5H-cyclopenta[b]pyridine-3-carbonitrile (20, 89.9 g, 98% yield) as yellow to brown oil. For 20: $^1$H NMR (300 MHz, CDCl$_3$) δ 8.68 (s, 1H), 5.22 (m, 1H), 3.09 (m, 1H), 2.84 (m, 1H), 2.49 (m, 1H), 2.07 (m, 1H), 0.92 (s, 9H), 0.20 (s, 3H), 0.18 (s, 3H) ppm; LCMS (EI) m/z 309/311 (C$_{15}$H$_{21}$ClN$_2$OSi, (M+H)$^+$).

Example 6

Stability Study of Compound 1 Phosphoric Acid Salt Form I

Compound 1 phosphoric acid salt Form I was subjected to various different environmental conditions to assess stability. Results are shown in Table 2 below. As can be seen from the data, Form I has high stability even in the presence of heat and moisture. Only the heating at 210° C. showed a possible conversion to another solid form, but the conversion was reversible upon exposure to 40° C./75% RH for 4 days.

TABLE 2

| Conditions | Crystalline Form (XRPD) |
|---|---|
| Suspension in 0.5% methyl cellulose in water | Form I |
| 40° C./75% RH for 1 week | Form I |
| 50° C. vacuum dry for 1 day | Form I |
| 100° C. vacuum dry for 1 day | Form I |
| 210° C. vacuum dry for 20 min | Not Form I |
| 210° C. vacuum dry followed by 40° C./75% RH for 4 weeks | Form I |

Example 8

Preparation of Compound 1 Phosphoric Acid Salt Form I

Procedure A-Isopropanol:

To a solution of Compound 1 (25.68 mg, 0.05 mmol) in isopropanol (0.5 mL) was added 0.056 mL of a 0.1 M solution of phosphoric acid (0.12 mmol, 1.12 eq.) in isopropanol. The reaction mixture was stirred overnight. The resultant precipitate was collected by filtration, and the filter cake was air-dried to yield Form I.

Procedure B-Acetonitrile:

Compound 1 (50.35 mg, 0.216 mmol, 1 eq.) was combined with 0.1 mL of acetonitrile, and the mixture was stirred for 2 min to give a clear solution. To the resultant solution was added 0.108 mL of 1M solution of phosphoric acid (0.108 mmol, 1.1 eq.) in isopropanol to give a sticky slurry. The reaction mixture was heated to 78° C. and stirred for 2 h (note: slurry), after which time the reaction mixture was cooled to room temperature and stirred overnight. The resultant precipitate was collected by filtration, and the filter cake was dried to give Form I.

The Karl Fischer titration indicated that the salt of Compound 1 from acetonitrile contained about 1.419% water.

Procedure C-Ethanol:

Compound 1 (50.30 mg, 0.216 mmol, 1 eq.) was combined with 1.2 mL of ethanol, and the mixture was stirred to give a clear solution. To the resultant solution was added 0.108 mL of 1M solution of phosphoric acid (0.108 mmol, 1.1 eq.) in isopropanol to give a slurry. The resultant reaction mixture was heated to 79° C. and stirred to 2 h, after which time the reaction mixture was stirred at 81-83° C. for 2 h (note: slurry). The reaction mixture was cooled to room temperature and stirred for 2 h. The resultant precipitate was separated by filtration and the filter cake was dried to give Form I (55 mg, 91.8%).

Procedure D-Methanol:

Compound 1 (50 mg, 0.216 mmol, 1 eq.) was combined with 0.5 mL of methanol to give a clear solution. To the resultant solution was added 0.95 mL of 1M solution of phosphoric acid (0.95 mmol, 1.25 eq.) in isopropanol to give a sticky slurry. Methanol (0.5 mL) was added and the mixture was stirred for 1 h, after which time the reaction mixture was heated to 78° C. and stirred at that temperature for 2 h (note: slurry). The resultant precipitate was collected by filtration and the filter cake was dried to give Form I (42.6 mg, 91.7%).

The stoichiometric ratio between Compound 1 free base and phosphoric acid was determined by elemental analysis as 1:1. Elemental analysis: Calculated for $C_{26}H_{29}F_3N_5O_7P$: C, 51.07; H, 4.78; N, 11.45; P, 5.07. Found: C, 49.23; H, 4.57; N, 10.85; P, 5.28.

Example 9

Stability Study of Compound 1 Phosphoric Acid Salt Form I Under Phase Equilibration Conditions at 25° C. and 50° C.

Phase equilibration studies were designed to provide information on a predominant crystal form for phase identification. Compound 1 phosphoric acid salt (Form I) was equilibrated in a representative group of solvents at 25±1° C. (chloroform, DMF, 1,4-dioxane, methanol and methanol/20% water, 2-methoxyethanol and 2-methoxyethanol/20% water, MIBK, THF and THF/20% water, acetone, n-BuOH and n-BuOH/20% water, EtOH and EtOH/20% water, isobutyl acetate, 1-propanol and 1-propanol/20% water, isopropanol, water, and MEK) and 50±1° C. (chloroform, DMF, 1,4-dioxane, methanol and methanol/20% water, 2-methoxyethanol and 2-methoxyethanol/20% water, MIBK, THF and THF/20% water, acetone, n-BuOH and n-BuOH/20% water, EtOH and EtOH/20% water, EtOAc, ethyl formate, 1-propanol and 1-propanol/20% water, isopropanol, IPA/MeOH/Water (1.73/0.79/0.08), IPA/water (3/2), water) controlled by IKA® ETS-D5 temperature controller and IKA® RCT basic safety control.

To 3 mL of a solvent or a mixture of solvents (chosen from a list for the respective temperature) was added Compound 1 phosphate (Form I) until a cloudy solution was obtained, then, about 30 mg of Compound 1 phosphate (Form I) was added to the cloudy solution. The mixture was stirred at 25±1° C. or 50±1° C., respectively, for 2-3 days. The solid was filtered and analyzed by XRPD. The material was Form I for phase equilibration at 25±1° C. and 50±1° C. in all of the solvents and solvent mixtures tested, which is the same as the starting material Compound 1 phosphate (Form I).

Example 10

Preparation and Characterization of Compound 1 Phosphoric Acid Salt Form II.

A saturated solution of Compound 1 phosphate Form I (prepared in Example 1, 20 mL) in DMF was evaporated under air without stirring at 25±1° C. to give a solid, which was characterized by XRPD, DSC and TGA as Form II.

Experimental parameters for acquiring the XRPD data are as described in Example 2. The XRPD pattern is shown in FIG. 7 and XRPD data is provided in Table 3.

TABLE 3

| XRPD Data Form II | | |
|---|---|---|
| 2-Theta (°) | Height | H % |
| 4.7 | 2194 | 100 |
| 9.4 | 970 | 44.2 |
| 13.1 | 82 | 3.7 |
| 14.1 | 188 | 8.6 |
| 16.2 | 83 | 3.8 |
| 18.8 | 2026 | 92.4 |
| 19.2 | 171 | 7.8 |
| 21.2 | 446 | 20.3 |
| 22.3 | 107 | 4.9 |
| 23.0 | 123 | 5.6 |
| 24.8 | 305 | 13.9 |
| 26.4 | 99 | 4.5 |
| 26.7 | 139 | 6.3 |
| 27.6 | 113 | 5.1 |
| 28.4 | 83 | 3.8 |

TABLE 3-continued

| XRPD Data Form II | | |
|---|---|---|
| 2-Theta (°) | Height | H % |
| 29.0 | 29 | 1.3 |
| 29.4 | 40 | 1.8 |
| 30.2 | 184 | 8.4 |
| 33.3 | 322 | 14.7 |
| 34.1 | 135 | 6.2 |
| 34.9 | 264 | 12 |
| 38.2 | 136 | 6.2 |
| 38.8 | 48 | 2.2 |
| 39.8 | 85 | 3.9 |
| 43.3 | 166 | 7.6 |

Experimental parameters for acquiring the DSC data are as described in Example 3. The DSC thermogram is shown in FIG. 8 and displays an endothermic event at about 249° C.

Experimental parameters for acquiring the TGA data are as described in Example 4. The TGA thermogram is shown in FIG. 9.

Example 11

Preparation and Characterization of Compound 1 Phosphoric Acid Salt Form III.

A 20 mL saturated solution of Compound 1 phosphate (Form I) in DMF was evaporated under air without string at 50±1° C. to give a solid which was characterized by XRPD, DSC and TGA as Form III.

Experimental parameters for acquiring the XRPD data are as described in Example 2. The XRPD pattern is shown in FIG. 10 and XRPD data is provided in Table 4.

TABLE 4

| XRPD Data Form III | | |
|---|---|---|
| 2-Theta (°) | Height | H % |
| 4.6 | 425 | 85.1 |
| 7.1 | 50 | 9.9 |
| 9.4 | 129 | 25.9 |
| 13.3 | 166 | 33.3 |
| 15.7 | 89 | 17.8 |
| 16.3 | 173 | 34.7 |
| 18.9 | 500 | 100 |
| 19.2 | 289 | 57.9 |
| 21.2 | 290 | 58 |
| 22.5 | 220 | 44.1 |
| 23.1 | 216 | 43.2 |
| 24.3 | 88 | 17.7 |
| 24.9 | 142 | 28.4 |
| 25.6 | 65 | 13.1 |
| 26.7 | 165 | 33.1 |
| 27.7 | 89 | 17.7 |
| 29.1 | 61 | 12.1 |
| 30.4 | 62 | 12.4 |
| 33.4 | 41 | 8.2 |
| 34.2 | 66 | 13.2 |
| 35.0 | 72 | 14.3 |
| 38.3 | 46 | 9.3 |
| 38.8 | 57 | 11.5 |
| 43.4 | 43 | 8.7 |

Experimental parameters for acquiring the DSC data are as described in Example 3. The DSC thermogram is shown in FIG. 11 and displays an endothermic event at about 250° C.

Experimental parameters for acquiring the TGA data are as described in Example 4. The TGA thermogram is shown in FIG. 12.

Example 12

Preparation and Characterization of Compound 1 Phosphoric Acid Salt Form IV.

A 20 mL saturated solution of Compound 1 phosphate Form I in water was evaporated under air without string at 50±1° C. to give a solid which was characterized by XRPD, DSC and TGA as Form IV.

Experimental parameters for acquiring the XRPD data are as described in Example 2. The XRPD pattern is shown in FIG. 13 and XRPD data is provided in Table 5.

TABLE 5

XRPD Data Form IV

| 2-Theta (°) | Height | H % |
|---|---|---|
| 4.1 | 81 | 62.1 |
| 4.9 | 52 | 39.9 |
| 6.9 | 45 | 34.7 |
| 7.4 | 63 | 48.3 |
| 8.0 | 37 | 28.6 |
| 11.0 | 44 | 34 |
| 12.8 | 38 | 29 |
| 13.3 | 96 | 73.9 |
| 16.4 | 130 | 100 |
| 17.7 | 78 | 59.4 |
| 18.1 | 88 | 67.1 |
| 18.6 | 102 | 77.8 |
| 19.0 | 55 | 42 |
| 19.8 | 118 | 90.1 |
| 20.6 | 42 | 32.3 |
| 21.4 | 114 | 87 |
| 22.6 | 46 | 35.5 |
| 23.3 | 81 | 62 |
| 25.0 | 61 | 46.8 |
| 26.7 | 46 | 35.5 |
| 35.7 | 26 | 20.2 |
| 38.4 | 27 | 20.3 |

Experimental parameters for acquiring the DSC data are as described in Example 3. The DSC thermogram is shown in FIG. 14 and displays an endothermic event at about 245° C.

Experimental parameters for acquiring the TGA data are as described in Example 4. The TGA thermogram is shown in FIG. 15.

Example 13

Preparation and Characterization of Compound 1 Phosphoric Acid Salt Form V.

A 100 mL saturated solution of Compound 1 phosphate in water, prepared at 35° C., was quench-cooled to 4-5° C., and kept at the temperature for 1 h to give a thin slurry which was filtered and air-dried for 1 h. The solid was assigned as Compound 1 phosphate Form V and characterized by XRPD, DSC and TGA.

Experimental parameters for acquiring the XRPD data are as described in Example 2. The XRPD pattern is shown in FIG. 16 and XRPD data is provided in Table 6.

TABLE 6

XRPD Data Form V

| 2-Theta (°) | Height | H % |
|---|---|---|
| 4.2 | 50 | 8.5 |
| 5.5 | 53 | 9 |
| 7.3 | 301 | 51.4 |
| 9.3 | 75 | 12.8 |
| 10.2 | 46 | 7.8 |
| 10.9 | 316 | 53.9 |
| 11.9 | 50 | 8.5 |
| 12.7 | 72 | 12.4 |
| 13.1 | 148 | 25.2 |
| 14.7 | 84 | 14.4 |
| 16.4 | 479 | 81.8 |
| 17.5 | 159 | 27.2 |
| 18.1 | 232 | 39.6 |
| 18.5 | 586 | 100 |
| 19.8 | 531 | 90.6 |
| 20.6 | 88 | 15 |
| 21.2 | 102 | 17.3 |
| 22.6 | 244 | 41.6 |
| 23.1 | 91 | 15.5 |
| 23.8 | 81 | 13.9 |
| 24.7 | 120 | 20.6 |
| 26.1 | 252 | 43.1 |
| 26.7 | 161 | 27.5 |
| 30.5 | 116 | 19.7 |
| 30.8 | 61 | 10.5 |
| 31.8 | 69 | 11.8 |
| 35.1 | 86 | 14.6 |
| 35.5 | 65 | 11.2 |
| 37.3 | 104 | 17.7 |
| 37.7 | 65 | 11.1 |
| 39.7 | 53 | 9.1 |
| 44.2 | 51 | 8.7 |

Experimental parameters for acquiring the DSC data are as described in Example 3. The DSC thermogram is shown in FIG. 17.

Experimental parameters for acquiring the TGA data are as described in Example 4. The TGA thermogram is shown in FIG. 18.

Example 14

Preparation and Characterization of Compound 1 Phosphoric Acid Salt Form VI.

To 150 mL water was added Compound 1 phosphate to give a slurry which was stirred for 2 h to give a suspension. The suspension was filtered and the filtrate was cooled to 4-5° C. and held at 4-5° C. for 3 days. The suspension was filtered to isolate crystal solid which was characterized by XRPD, DSC and TGA as Form VI.

Experimental parameters for acquiring the XRPD data are as described in Example 2. The XRPD pattern is shown in FIG. 19 and XRPD data is provided in Table 7.

TABLE 7

XRPD Data Form VI

| 2-Theta (°) | Height | H % |
|---|---|---|
| 3.7 | 133 | 21.2 |
| 4.1 | 222 | 35.4 |
| 6.5 | 629 | 100 |
| 8.3 | 437 | 69.5 |
| 10.7 | 216 | 34.4 |
| 13.2 | 230 | 36.6 |
| 14.6 | 171 | 27.3 |
| 16.1 | 61 | 9.7 |
| 17.3 | 263 | 41.8 |
| 18.3 | 59 | 9.4 |
| 19.1 | 444 | 70.7 |
| 20.1 | 171 | 27.2 |
| 20.8 | 77 | 12.2 |

TABLE 7-continued

XRPD Data Form VI

| 2-Theta (°) | Height | H % |
|---|---|---|
| 21.5 | 130 | 20.7 |
| 21.8 | 74 | 11.7 |
| 22.8 | 59 | 9.4 |
| 24.1 | 85 | 13.5 |
| 25.1 | 114 | 18.1 |
| 26.6 | 108 | 17.2 |
| 27.1 | 74 | 11.7 |
| 27.8 | 83 | 13.2 |
| 30.8 | 93 | 14.8 |
| 34.5 | 47 | 7.5 |
| 36.2 | 80 | 12.7 |
| 38.5 | 60 | 9.5 |
| 40.2 | 54 | 8.7 |
| 40.8 | 49 | 7.8 |
| 44.6 | 45 | 7.2 |

Experimental parameters for acquiring the DSC data are as described in Example 3. The DSC thermogram is shown in FIG. 20.

Experimental parameters for acquiring the TGA data are as described in Example 4. The TGA thermogram is shown in FIG. 21.

Example 15

Study of Polymorphism of Compound 1 Phosphate using Anti-Solvent Addition Saturated solutions of Compound 1 phosphate were prepared by adding the Compound 1 phosphate (Form I) to DMF, MeOH, MeOH/20% water and DMSO respectively. An anti-solvent was added to induce precipitation. MTBE, IPAc, EtOAc, MeCN, MIBK, MEK and toluene were selected as the anti-solvents. Experiments that did not produce any particulate solids on anti-solvent addition were not studied further.

In antisolvent addition (see Table 8), Form I was identified from MeOH/IPAc, MeOH/EtOAc, MeOH/MEK, aq. MeOH/MTBE, DMSO/MeCN, DMSO/IPAc, and DMSO/MEK. Form II was identified from MeOH/MeCN, aq. MeOH/MeCN, and aq. MeOH/IPAc. Amorphous was found from MeOH/TBME and MeOH/MIBK.

The XRPD pattern for amorphous Compound 1 phosphate is shown in FIG. 23.

TABLE 8

| Solvent (mL) | Anti-solvent (mL) | Solid state form |
|---|---|---|
| DMF (2 mL) | IPAc (8 mL) | n/a |
| DMF (2 mL) | MTBE (8 mL) | n/a |
| MeOH (2 mL) | MTBE (8 mL) | amorphous |
| MeOH (2 mL) | IPAc (8 mL) | Form I |
| MeOH (2 mL) | EtOAc (8 mL) | Form I |
| MeOH (2 mL) | CH$_2$Cl$_2$ (8 mL) | Clear solution |
| MeOH (2 mL) | MeCN (8 mL) | Form II |
| MeOH (2 mL) | MIBK (8 mL) | amorphous |
| MeOH (2 mL) | MEK (8 mL) | Form I |
| MeOH/20% water (2 mL) | MeCN (8 mL) | Form II |
| MeOH/20% water (2 mL) | MTBE (8 mL) | Form I |
| MeOH/20% water (2 mL) | IPAc (8 mL) | Form II |
| DMSO (0.5 mL) | MeCN (5 mL) | Form I |
| DMSO (0.5 mL) | IPAc (5 mL) | Form I |
| DMSO (0.5 mL) | MEK (5.5 mL) | Form I |
| DMSO (0.5 mL) | Acetone (8 mL) | n/a |
| DMSO (0.5 mL) | Toluene (6 mL) | n/a |

Example 16

Study of Polymorphism of Compound 1 Phosphate Using Reverse Addition

Saturated solutions of Compound 1 phosphate were prepared in DMF, MeOH, MeOH/20% water and DMSO listed in Table 9, and added to a larger volume of a miscible anti-solvent (i.e. MTBE, IPAc, EtOAc, MeCN). Experiments that did not produce any particulate solids upon addition to the anti-solvent were not studied further. Form I was identified from most solvents, except Form II was identified from MeOH/MeCN, aq. MeOH/MeCN, and aq. MeOH/IPAc. Amorphous solid was identified from MeOH/MTBE, MeOH/EtOAc and MeOH/MIBK.

TABLE 9

| Solvent (mL) | Anti-solvent (mL) | Solid state form |
|---|---|---|
| DMF (2 mL) | IPAc (8 mL) | n/a |
| DMF (2 mL) | MTBE (8 mL) | n/a |
| MeOH (2 mL) | MTBE (8 mL) | Amorphous |
| MeOH (2 mL) | IPAc (8 mL) | Form I |
| MeOH (2 mL) | EtOAc (8 mL) | amorphous |
| MeOH (2 mL) | CH$_2$Cl$_2$ (8 mL) | n/a |
| MeOH (2 mL) | MeCN (8 mL) | Form II |
| MeOH (2 mL) | MIBK (8 mL) | Amorphous |
| MeOH (2 mL) | MEK (8 mL) | Form I |
| MeOH/20% water (2 mL) | MeCN (8 mL) | Form II |
| MeOH/20% water (2 mL) | MTBE (8 mL) | Form I |
| MeOH/20% water (2 mL) | IPAc (8 mL) | Form II |
| DMSO (0.5 mL) | IPAc (5 mL) | Form I |
| DMSO (0.5 mL) | MeCN (5 mL) | Form I |
| DMSO (0.5 mL) | MEK (5.5 mL) | Form I |
| DMSO (0.5 mL) | Acetone (8 mL) | n/a |
| DMSO (0.5 mL) | Toluene (6 mL) | n/a |

Example 17

Compound 1 Phosphate Study Using Quench-Cooling

Saturated solutions of Compound 1 phosphate prepared at 35° C. were quench cooled to about −20° C. to −25° C. to induce precipitation of higher energy crystalline forms. Representative solvents were chosen based on solubility data measured at 25° C. and 50° C. (See Example 7). The studied solvents and the crystalline forms resulting from the experiments are shown in Table 10. Form I was identified from aq. THF and aq. EtOH. Form V and Form VI were identified from water.

TABLE 10

| Solvent (mL) | Solid state form |
|---|---|
| DMF | Clear solution |
| MeOH | Clear solution |

TABLE 10-continued

| Solvent (mL) | Solid state form |
| --- | --- |
| MeOH/20% water | Clear solution |
| 2-methoxyethanol | Clear solution |
| 2-methoxyethanol/20% water | Clear solution |
| THF/20% water | Form I |
| EtOH/20% water | Form I |
| 1-PrOH/20% water | Clear solution |
| 2-PrOH/20% water | Clear solution |
| Water (Cooled to 4-5° C.) | Form V |
| Water (Cooled to 4-5° C.) | Form VI |

Example 18

Study of Polymorphism of Compound 1 Phosphate Using Heating and Cooling Cycles

This experiment was designed to search for stable crystalline forms. Saturated solutions were prepared at 50° C., and cooled in a bath slowly by using a programmed circulating bath to give clear solution for all solvents. To the clear solution was added about 10 mg of Compound 1 phosphate Form I to give slurry. The resulting slurry was then heated to 50° C. over 2 hours and then cooled down to 5° C. over 2 hours. This process was repeated for 3 days and the solid was filtered for further analysis. The results are presented in Table 11. Form I was identified for all of the samples.

TABLE 11

| Solvent (mL) | Solid state form |
| --- | --- |
| DMF | Form I |
| Methanol | Form I |
| Methanol/20% water | Form I |
| 2-Methoxyethanol | Form I |
| 2-Methoxyethanol/20% water | Form I |
| THF/20% water | Form I |
| n-BuOH/10% water | Form I |
| EtOH/20% water | Form I |
| n-Propanol/20% water | Form I |
| IPA/30% water | Form I |
| Water | Form I |

Example 19

Study of Polymorphism of Compound 1 Phosphate Using Evaporation

Evaporation studies were carried out to identify the predominant crystal form during uncontrolled precipitation. Experiments that did not result in any particulate solids (i.e. clear thin films and oils) were not studied further (n/a). XRPD was used to characterize the solid-state morphology of the crystalline forms of the evaporation samples at 25±1° C. and 50±1° C. controlled by IKA® ETS-D5 temperature controller and IKA® RCT basic safety control.

The results are presented in Table 12 (25±1° C.) and Table 13 (50±1° C.). Evaporation at 25±1° C. (Table 12) resulted in polymorphic Form II (DMF). Evaporation at 50±1° C. (Table 13) resulted in two polymorphic forms including Form III (DMF) and Form IV (water).

TABLE 12

| Evaporation at 25 ± 1° C. | |
| --- | --- |
| Solvent (mL) | Solid state form |
| MeCN | n/a |
| Chloroform | n/a |
| Dichloromethane | n/a |
| DMF | Form II |
| 1,4-Dioxane/5% water | n/a |
| 1,4-Dioxane | n/a |
| Methanol | n/a |
| Methanol/20% water | Form I |
| 2-Methoxyethanol | Form I |
| MIBK | n/a |
| Toluene | n/a |
| Hexane | n/a |
| THF | n/a |
| Acetone | n/a |
| n-BuOH | n/a |
| MTBE | n/a |
| DMSO | Form I |
| EtOH | n/a |
| EtOAc | n/a |
| Ethyl formate | n/a |
| Heptane | n/a |
| Isobutyl acetate | n/a |
| IPAc | n/a |
| 1-Propanol | n/a |
| IPA | n/a |
| Water | n/a |
| MEK | n/a |

TABLE 13

| Evaporation 50 ± 1° C. | |
| --- | --- |
| Solvent (mL) | Solid state form |
| MeCN | n/a |
| Chloroform | n/a |
| DMF | Form III |
| 1,4-Dioxane | n/a |
| Methanol | Form I |
| MeOH/20% water | Form I |
| 2-Methoxyethanol | Form I |
| MIBK | n/a |
| Toluene | n/a |
| Hexane | n/a |
| THF | n/a |
| Acetone | n/a |
| n-BuOH | n/a |
| MTBE | n/a |
| DMSO | Form I |
| EtOH | n/a |
| EtOAc | n/a |
| Ethyl formate | n/a |
| Heptane | n/a |
| Isobutyl acetate | n/a |
| IPAc | n/a |
| 1-Propanol | n/a |
| IPA | n/a |
| Water | Form IV |
| MEK | n/a |

Example 20

Competitive Stability Study of Compound 1 Phosphate Crystalline Solids in IPA/MeOH/Water/DMSO To evaluate the transformation of Compound 1 phosphate solid forms, competitive slurry experiments were performed as follows: to a saturated solution (1.5 mL) of Compound 1 phosphate Form I in the solvent as listed in Table 14 was added Form I (6 mg), followed by stirring to give a cloudy solution, then 6 mg each of Form II through Form VI were added to the mixture. The slurry was stirred for 2 days at room temperature and analyzed by XRPD. The results in Table 14 revealed that the Compound 1 phosphate Form I appears to be the most stable form in either of the IPA/methanol/water/DMSO mixtures.

TABLE 14

| Solvent (mL) | Solid state form |
|---|---|
| IPA/MeOH/water/DMSO (61.8/28.2/2.9/7.1) | Form I |
| IPA/MeOH/water/DMSO (56.6/28.3/3.0/12.1) | Form I |

Example 22

Karl Fisher Titration of the Compound 1 Phosphate Crystalline Solid Forms

The results of Karl Fisher titration of the Compound 1 phosphate polymorphs Forms I-VI are presented in Table 15.

TABLE 15

| Solid state form | Water % | Notes |
|---|---|---|
| Form I | 1.5 | GMP dried |
| Form II | 1.4 | Sample sealed in vial |
| Form III | 1.4 | Sample sealed in vial |
| Form IV | 3.0 | Sample sealed in vial |
| Form V | 2.4 | Sample sealed in vial |
| Form VI | 15.9 | Almost fresh sample |

Karl-Fischer analysis of Compound 1 phosphate Forms I-VI was conducted. Each experiment revealed a water content within the range of 1.40-15.9% indicating that each of the Forms I-VI may be hydrated.

Example 23

Preparation and Characterization of Compound 1 Dihydrochloric Acid Salt

Compound 1 (55.2 mg, 0.107 mmol) was combined with 0.7 mL isopropyl alcohol (IPA) and stirred for 2 minutes to give a clear solution. Hydrochloric acid solution (0.25 mL, 0.25 mmol, 2.34 eq; 1M HCl in IPA/IPAc from 3.7 M HCl in IPAc) was added to give a slurry which was heated to 50° C. and stirred for 15 min. The resulting mixture was cooled to RT, stirred overnight, filtered and dried under vacuum (6 h) to give the final product (61.8 mg, 98%).

The stoichiometric ratio between Compound 1 and hydrochloric acid was determined by elemental analysis as 1:2. $^1$H NMR indicated the salt contained 7.8% isopropanol, and Karl-Fischer titration indicated a water content of about 0.5$^{86}$%. Elemental Analysis: Calc'd for $C_{29}H_{35}Cl_2F_3N_5O_4$: C, 53.67; H, 5.35; N, 10.80; Cl, 10.95. Found: C, 53.26; H, 5.21; N, 10.57; Cl, 10.83.

Compound 1 dihydrochloric acid salt was characterized by XRPD, DSC and TGA. Experimental parameters for acquiring the XRPD data are as described in Example 2. The XRPD pattern is shown in FIG. 4. Experimental parameters for acquiring the DSC data are as described in Example 3. The DSC thermogram is shown in FIG. 5. The DSC thermogram revealed a major endothermic peak at about 213° C. Experimental parameters for acquiring the TGA data are as described in Example 4. The TGA thermogram is shown in FIG. 6.

XRPD data is provided in Table 17.

TABLE 17

| 2-Theta (°) | Height | H % |
|---|---|---|
| 3.8 | 176 | 19.5 |
| 8.3 | 376 | 41.8 |
| 11.2 | 152 | 16.9 |
| 12.4 | 231 | 25.7 |
| 13.9 | 79 | 8.8 |
| 15.6 | 218 | 24.2 |
| 16.6 | 129 | 14.3 |
| 18.9 | 632 | 70.3 |
| 20.0 | 103 | 11.4 |
| 22.1 | 186 | 20.6 |
| 23.1 | 194 | 21.5 |
| 23.9 | 108 | 12.1 |
| 25.0 | 899 | 100 |
| 26.2 | 95 | 10.6 |
| 27.2 | 167 | 18.6 |
| 28.4 | 197 | 21.9 |
| 30.0 | 228 | 25.3 |
| 31.8 | 150 | 16.7 |
| 33.6 | 163 | 18.2 |
| 35.2 | 184 | 20.5 |
| 37.3 | 150 | 16.7 |
| 39.6 | 69 | 7.6 |
| 41.9 | 148 | 16.5 |
| 43.3 | 63 | 7 |

Example 24

Preparation and Characterization of Compound 1 Monohydrochloric Acid Salt

To a solution of Compound 1 free base (see Example 1, step 6; 0.05 mmol, 25.68 mg) in isopropanol (0.5 mL, 0.1 M) was added 0.056 mL of hydrochloric acid (0.056 mmol, 1.12 eq., 1.0 M solution in IPA/IPAc prepared from 3.7 M HCl in IPAc (isopropyl acetate)). The reaction mixture was stirred overnight. The resultant precipitate was removed by filtration, and the filter cake was washed with MTBE and the solid was dried under vacuum overnight to afford the title salt.

Compound 1 monohydrochloric acid salt was characterized by XRPD and DSC. An XRPD pattern is provided in FIG. 22. Experimental parameters for acquiring the DSC data are as described in Example 3. The DSC thermogram is shown in FIG. 23.

XRPD data is provided in Table 18.

TABLE 18

| 2-Theta (°) | Height | H % |
|---|---|---|
| 3.5 | 102 | 27.3 |
| 4.0 | 105 | 28 |
| 7.8 | 126 | 33.6 |
| 8.8 | 134 | 35.7 |
| 11.9 | 57 | 15.3 |
| 12.6 | 121 | 32.2 |
| 14.5 | 138 | 36.8 |
| 15.0 | 47 | 12.5 |
| 15.9 | 70 | 18.8 |
| 16.6 | 44 | 11.6 |
| 17.4 | 113 | 30.2 |
| 19.7 | 74 | 19.8 |
| 20.4 | 59 | 15.8 |
| 20.6 | 54 | 14.4 |
| 22.3 | 74 | 19.9 |
| 23.8 | 186 | 49.6 |
| 24.6 | 84 | 22.3 |

TABLE 18-continued

| 2-Theta (°) | Height | H % |
|---|---|---|
| 25.2 | 375 | 100 |
| 26.3 | 80 | 21.4 |
| 26.5 | 82 | 21.8 |
| 27.4 | 38 | 10.2 |
| 28.8 | 90 | 24 |
| 29.2 | 72 | 19.2 |
| 31.1 | 75 | 19.9 |
| 31.5 | 44 | 11.7 |
| 31.7 | 42 | 11.3 |
| 34.5 | 69 | 18.3 |
| 37.6 | 46 | 12.4 |
| 40.9 | 43 | 11.4 |
| 41.3 | 32 | 8.6 |
| 41.8 | 34 | 8.9 |

Example 25

Preparation and Characterization of Compound 1 Maleic Acid Salt

A volume of 1.0 mL of isopropanol was added to Compound 1 free base (50.30 mg, 0.216 mmol, 1 eq.). The resultant mixture was stirred to give a clear solution. Maleic acid (14.2 mg. 0.122 mmol, 1.21 eq.) was added to this solution and the resultant reaction mixture was stirred to give a clear solution. The stirring continued for 1 h. To this solution, 1 mg of crystals (seeds) obtained from IPA/heptane were added and the resultant mixture was stirred to give a slurry. The slurry was continuously stirred for 3 h. The precipitate was removed by filtration, and the filter cake was washed with MTBE and dried under vacuum overnight to afford the title salt (56.8 mg, 89.2%).

The stoichiometric ratio of the salt between Compound 1 free base and maleic acid was determined by $^1$H NMR as 1:1. The crystallinity of the Compound 1 maleate was confirmed by XRPD, DSC, and TGA.

Experimental parameters for acquiring the XRPD data are as described in Example 2. The XRPD pattern is shown in FIG. 24. Experimental parameters for acquiring the DSC data are as described in Example 3. The DSC thermogram is shown in FIG. 25. Experimental parameters for acquiring the TGA data are as described in Example 4. The TGA thermogram is shown in FIG. 26.

XRPD data is provided in Table 19.

TABLE 19

| 2-Theta (°) | Height | H % |
|---|---|---|
| 5.2 | 108 | 3.9 |
| 9.0 | 762 | 27.4 |
| 9.5 | 851 | 30.6 |
| 10.4 | 504 | 18.1 |
| 11.2 | 1255 | 45.1 |
| 12.8 | 204 | 7.3 |
| 14.8 | 632 | 22.7 |
| 15.9 | 748 | 26.9 |
| 17.0 | 323 | 11.6 |
| 17.8 | 460 | 16.5 |
| 18.5 | 2781 | 100 |
| 19.5 | 687 | 24.7 |
| 19.9 | 1036 | 37.2 |
| 20.9 | 1007 | 36.2 |
| 21.3 | 1421 | 51.1 |
| 22.9 | 2122 | 76.3 |
| 23.6 | 538 | 19.3 |
| 24.4 | 575 | 20.7 |
| 24.8 | 1904 | 68.5 |
| 25.8 | 1638 | 58.9 |

TABLE 19-continued

| 2-Theta (°) | Height | H % |
|---|---|---|
| 27.6 | 1166 | 41.9 |
| 29.2 | 492 | 17.7 |
| 30.9 | 1025 | 36.9 |
| 32.5 | 268 | 9.7 |
| 33.4 | 97 | 3.5 |
| 34.2 | 429 | 15.4 |
| 35.6 | 252 | 9 |
| 36.0 | 152 | 5.5 |
| 36.7 | 200 | 7.2 |
| 37.6 | 115 | 4.2 |
| 38.2 | 61 | 2.2 |
| 38.6 | 77 | 2.8 |
| 39.9 | 123 | 4.4 |
| 40.7 | 220 | 7.9 |
| 41.6 | 251 | 9 |
| 42.3 | 471 | 16.9 |
| 43.2 | 328 | 11.8 |
| 43.6 | 161 | 5.8 |

Example 26

Preparation and Characterization of Compound 1 Adipic Acid Salt

A volume of 0.6 mL of isopropanol was added to Compound 1 free base (37.8 mg, 0.216 mmol. 1 eq) and the resultant mixture was stirred for 1 min to give a clear solution. Adipic acid (26.8 mg, 0.183 mmol, 2.49 eq.) was added to the solution and the resultant slurry was stirred at room temperature for 5 min. The reaction mixture was heated to 50° C. and stirred at that temperature for 15 min. (Note: clear solution). The reaction mixture was cooled to room temperature and stirred for 3 h. Heptane (0.2 mL) was added and the reaction mixture was stirred to give a slurry, which was continuously stirred overnight. The precipitate was removed by filtration and the filter cake was washed with MTBE, collected, and dried under vacuum overnight to afford the title salt (36.5 mg, 84.5% yield).

The stoichiometric ratio of the salt between Compound 1 free base and adipic acid was determined by $^1$H NMR as 1:1. The crystallinity of Compound 1 adipate was confirmed by XRPD, DSC, and TGA. Experimental parameters for acquiring the XRPD data are as described in Example 2. The XRPD pattern is shown in FIG. 27. Experimental parameters for acquiring the DSC data are as described in Example 3. The DSC thermogram is shown in FIG. 28. Experimental parameters for acquiring the TGA data are as described in Example 4. The TGA thermogram is shown in FIG. 29.

XRPD data is provided in Table 20.

TABLE 20

| 2-Theta (°) | Height | H % |
|---|---|---|
| 3.8 | 169 | 10 |
| 9.0 | 443 | 26.3 |
| 9.3 | 1025 | 60.8 |
| 10.1 | 235 | 14 |
| 12.0 | 267 | 15.8 |
| 12.5 | 62 | 3.7 |
| 13.3 | 110 | 6.5 |
| 15.0 | 754 | 44.7 |
| 16.2 | 464 | 27.5 |
| 17.6 | 368 | 21.8 |
| 18.7 | 792 | 46.9 |
| 20.0 | 1687 | 100 |
| 21.2 | 147 | 8.7 |
| 22.1 | 708 | 42 |
| 22.7 | 415 | 24.6 |

TABLE 20-continued

| 2-Theta (°) | Height | H % |
|---|---|---|
| 24.3 | 1154 | 68.4 |
| 24.9 | 766 | 45.4 |
| 26.9 | 254 | 15.1 |
| 27.1 | 425 | 25.2 |
| 28.7 | 337 | 20 |
| 30.2 | 75 | 4.5 |
| 31.7 | 124 | 7.3 |
| 33.7 | 140 | 8.3 |
| 35.0 | 95 | 5.6 |
| 35.6 | 58 | 3.4 |
| 36.3 | 71 | 4.2 |
| 36.7 | 77 | 4.6 |
| 38.2 | 119 | 7 |
| 40.5 | 62 | 3.7 |
| 41.8 | 168 | 9.9 |
| 43.2 | 100 | 5.9 |

Example 27

Preparation and Characterization of Compound 1 Hydrobromic Acid Salt

To a 0.1 M solution of Compound 1 free base (0.05 mmol, 25.68 mg) in isopropanol (0.5 mL) was added 0.12 mL of hydrobromic acid (0.12 mmol, 2.4 eq., 1.0 M solution in isopropanol/water). The resultant mixture was stirred overnight to give a slurry. The precipitate was removed by filtration and the filter cake was washed with MTBE and dried under vacuum overnight to give the desired product.

Figure 30:
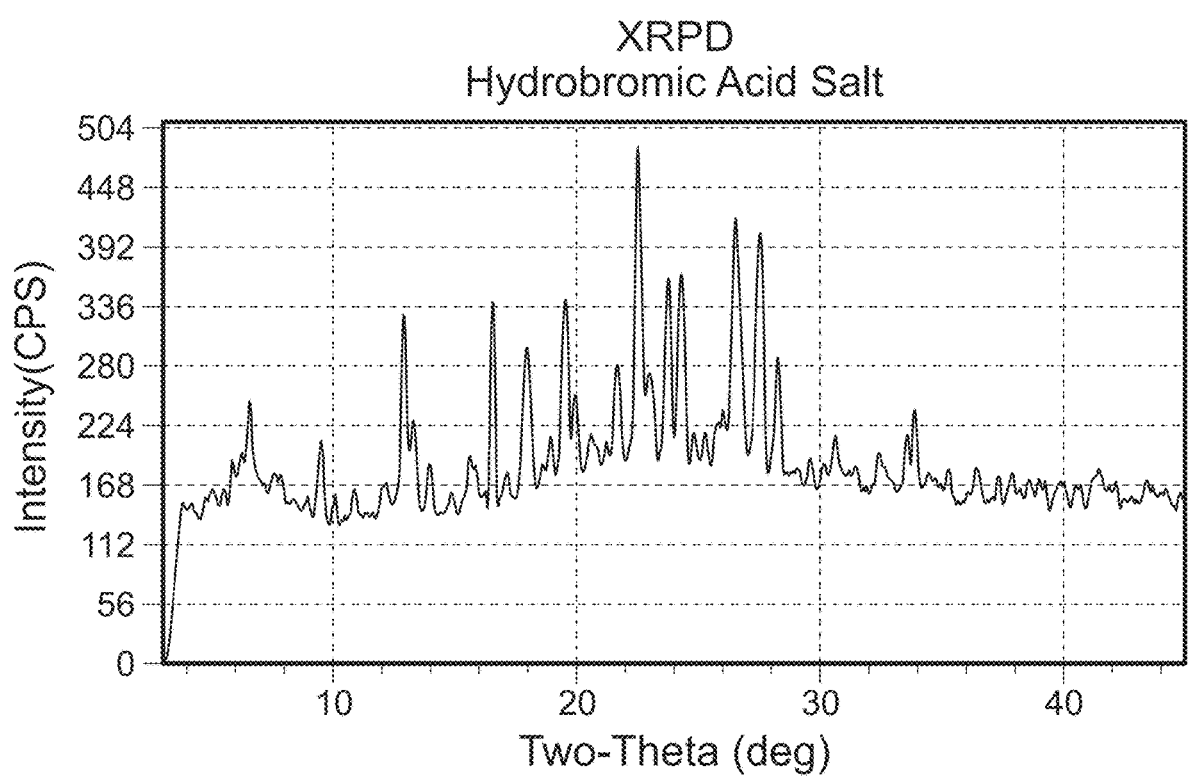
FIG. 30 shows the XRPD pattern of a solid form of Compound 1 hydrobromic acid salt.
Figure 31:
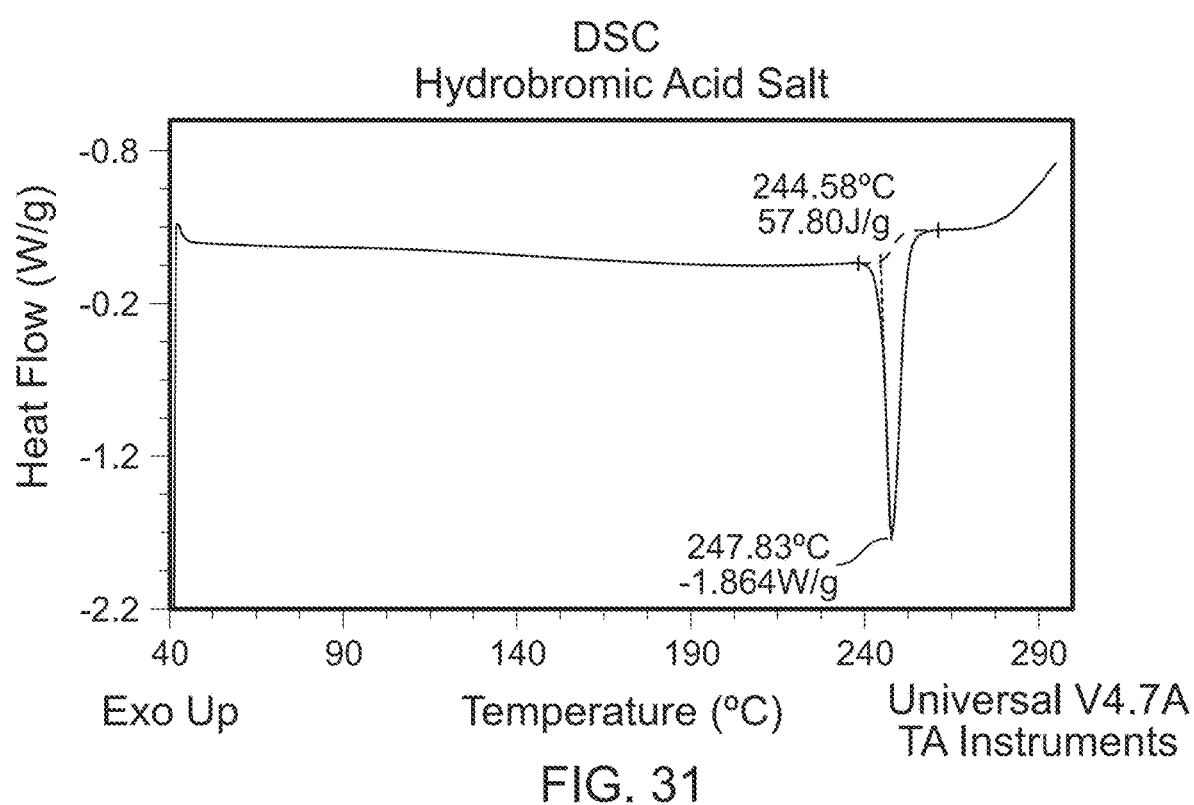
FIG. 31 shows the DSC thermogram of a solid form of Compound 1 hydrobromic acid salt.

Experimental parameters for acquiring the XRPD data are as described in Example 2. The XRPD pattern is shown in FIG. 30. Experimental parameters for acquiring the DSC data are as described in Example 3. The DSC thermogram is shown in FIG. 31. Experimental parameters for acquiring the TGA data are as described in Example 4. The TGA thermogram is shown in FIG. 32.

XRPD data is provided in Table 21.

TABLE 21

| 2-Theta (°) | Height | H % |
|---|---|---|
| 3.8 | 171 | 55.4 |
| 4.2 | 142 | 46.2 |
| 6.5 | 99 | 32.3 |
| 9.5 | 93 | 30.3 |
| 10.1 | 41 | 13.2 |
| 10.9 | 47 | 15.1 |
| 12.9 | 189 | 61.3 |
| 13.2 | 102 | 33.2 |
| 13.9 | 64 | 20.6 |
| 15.6 | 69 | 22.4 |
| 16.6 | 263 | 85.3 |
| 17.9 | 143 | 46.6 |
| 18.9 | 48 | 15.6 |
| 19.5 | 201 | 65.2 |
| 19.9 | 77 | 24.9 |
| 21.7 | 101 | 33 |
| 22.5 | 308 | 100 |
| 23.0 | 111 | 35.9 |
| 23.7 | 179 | 58.2 |
| 24.3 | 188 | 61 |
| 26.5 | 256 | 83.1 |
| 27.5 | 239 | 77.5 |
| 28.3 | 135 | 43.8 |
| 30.6 | 48 | 15.5 |
| 32.5 | 49 | 15.9 |
| 33.6 | 77 | 25.1 |
| 33.9 | 86 | 27.8 |
| 35.3 | 50 | 16.3 |

Example 28

Preparation and Characterization of Compound 1 Mandelic Acid Salt

To the 0.1 M solution of Compound 1 free base (0.05 mmol, 25.68 mg) in IPA (0.5 mL) was added mandelic acid (8.1 mg, 0.053 mmol, 1.06 eq.). The mixture was stirred overnight. The slurry was filtered, washed with MTBE to give Compound 1 mandelate salt, which was analyzed by XRPD, DSC and TGA.

Experimental parameters for acquiring the XRPD data are as described in Example 2. The XRPD pattern is shown in FIG. 33. Experimental parameters for acquiring the DSC data are as described in Example 3. The DSC thermogram is shown in FIG. 34. Experimental parameters for acquiring the TGA data are as described in Example 4. The TGA thermogram is shown in FIG. 35.

XRPD data is provided in Table 22.

TABLE 22

| 2-Theta (°) | Height | H % |
|---|---|---|
| 4.0 | 190 | 9.7 |
| 4.8 | 54 | 2.7 |
| 8.7 | 89 | 4.5 |
| 11.2 | 753 | 38.3 |
| 12.0 | 286 | 14.5 |
| 13.8 | 207 | 10.6 |
| 14.9 | 359 | 18.3 |
| 15.7 | 142 | 7.2 |
| 16.7 | 206 | 10.5 |
| 17.3 | 222 | 11.3 |
| 18.6 | 788 | 40.1 |
| 20.2 | 107 | 5.4 |
| 20.6 | 379 | 19.3 |
| 22.5 | 537 | 27.3 |
| 24.1 | 1965 | 100 |
| 25.3 | 338 | 17.2 |
| 26.6 | 221 | 11.3 |
| 27.9 | 118 | 6 |
| 28.6 | 162 | 8.2 |
| 29.4 | 124 | 6.3 |
| 30.2 | 60 | 3 |
| 31.0 | 138 | 7 |
| 31.5 | 59 | 3 |
| 32.7 | 91 | 4.6 |
| 33.5 | 110 | 5.6 |
| 35.7 | 125 | 6.4 |
| 37.5 | 103 | 5.2 |
| 38.6 | 129 | 6.6 |
| 39.3 | 126 | 6.4 |
| 40.9 | 112 | 5.7 |
| 42.3 | 85 | 4.4 |
| 44.0 | 113 | 5.7 |

Example 29

Compound 1 Salicylic Acid Salt

To the 0.1 M solution of Compound 1 free base (0.05 mmol, 25.68 mg) in isopropyl alcohol (IPA) (0.5 mL) was added salicylic acid (0.058 mmol, 8.01 mg, 1.16 eq.). The resultant reaction mixture was stirred overnight to form a slurry. The precipitate was removed by filtration, and the filter cake was washed with methyl tert-butyl ether (MTBE) to give Compound 1 salicylic acid salt, which was characterized by XRPD and DSC.

Experimental parameters for acquiring the XRPD data are as described in Example 2. The XRPD pattern is shown in FIG. 36. Experimental parameters for acquiring the DSC data are as described in Example 3. The DSC thermogram is shown in FIG. 37.

XRPD data is provided in Table 23.

TABLE 23

| 2-Theta (°) | Height | H % |
| --- | --- | --- |
| 8.7 | 58 | 2.7 |
| 9.7 | 77 | 3.5 |
| 10.9 | 234 | 10.7 |
| 11.3 | 406 | 18.7 |
| 11.8 | 609 | 28 |
| 13.2 | 80 | 3.7 |
| 13.6 | 48 | 2.2 |
| 14.5 | 163 | 7.5 |
| 14.8 | 366 | 16.8 |
| 15.6 | 231 | 10.6 |
| 16.7 | 288 | 13.2 |
| 18.3 | 143 | 6.6 |
| 18.7 | 422 | 19.4 |
| 19.9 | 161 | 7.4 |
| 20.6 | 58 | 2.7 |
| 21.2 | 735 | 33.8 |
| 21.9 | 1536 | 70.6 |
| 23.0 | 1123 | 51.6 |
| 23.4 | 2176 | 100 |
| 24.1 | 716 | 32.9 |
| 25.1 | 501 | 23 |
| 25.8 | 93 | 4.3 |
| 26.3 | 410 | 18.8 |
| 27.1 | 57 | 2.6 |
| 27.7 | 151 | 6.9 |
| 28.1 | 142 | 6.5 |
| 29.4 | 243 | 11.1 |
| 29.9 | 63 | 2.9 |
| 31.3 | 131 | 6 |
| 32.9 | 110 | 5 |
| 35.7 | 84 | 3.9 |
| 36.5 | 120 | 5.5 |
| 36.8 | 231 | 10.6 |
| 37.9 | 170 | 7.8 |
| 39.4 | 57 | 2.6 |
| 42.0 | 185 | 8.5 |
| 42.6 | 139 | 6.4 |
| 44.0 | 66 | 3 |
| 44.4 | 62 | 2.9 |

Example 30

Compound 1 Benzoic Acid Salt

To the 0.1 M solution of Compound 1 free base (0.05 mmol, 25.68 mg) in isopropyl alcohol (IPA) (0.5 mL) was added benzoic acid (7.05 mg, 0.0577 mmol, 1.16 eq.). The resultant reaction mixture was stirred overnight to form a slurry. The precipitate was removed by filtration, and the filter cake was washed with methyl tert-butyl ether (MTBE) to give Compound 1 benzoic acid salt, which was analyzed by XRPD.

Figure 38:
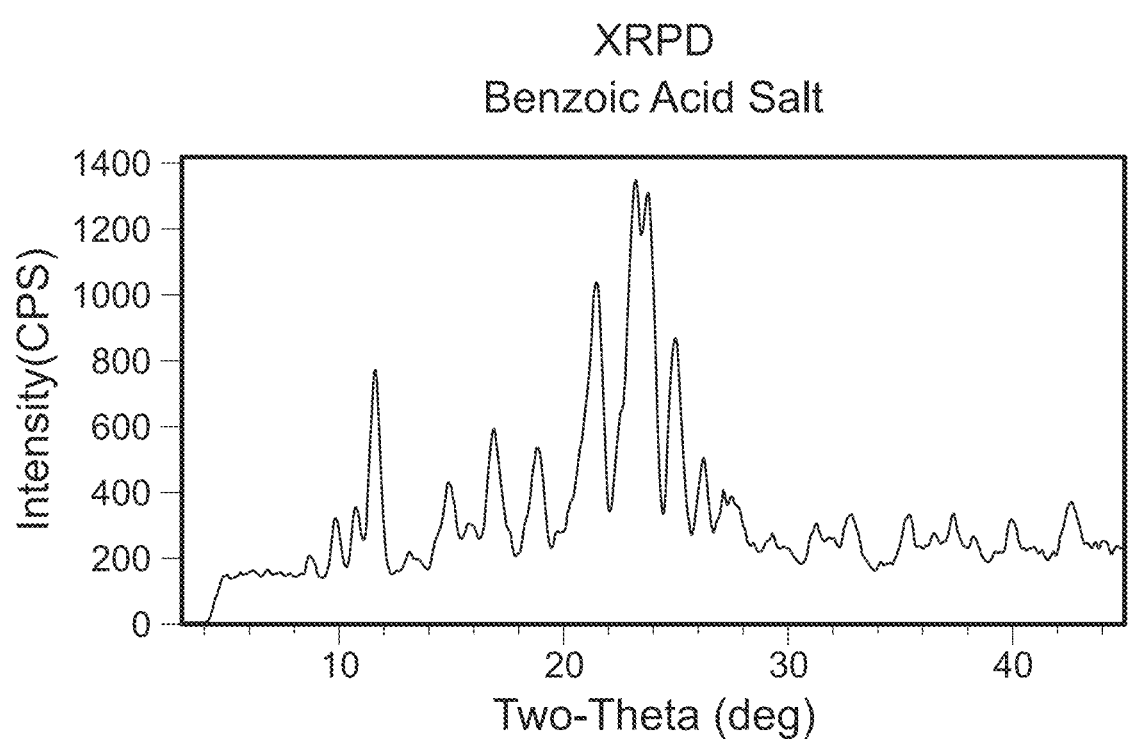
FIG. 38 shows the XRPD pattern of a solid form of Compound 1 benzoic acid salt.

Experimental parameters for acquiring the XRPD data are as described in Example 2. The XRPD pattern is shown in FIG. 38.

XRPD data is provided in Table 24.

TABLE 24

| 2-Theta (°) | Height | H % |
| --- | --- | --- |
| 4.9 | 156 | 15.9 |
| 8.7 | 83 | 8.5 |
| 9.8 | 180 | 18.3 |
| 10.7 | 129 | 13.1 |
| 11.6 | 566 | 57.8 |
| 13.1 | 74 | 7.5 |
| 14.9 | 225 | 22.9 |

TABLE 24-continued

| 2-Theta (°) | Height | H % |
| --- | --- | --- |
| 15.9 | 66 | 6.7 |
| 16.9 | 389 | 39.7 |
| 18.8 | 346 | 35.4 |
| 21.5 | 692 | 70.7 |
| 23.2 | 862 | 88 |
| 23.7 | 980 | 100 |
| 24.9 | 566 | 57.8 |
| 26.2 | 243 | 24.9 |
| 27.2 | 168 | 17.2 |
| 27.5 | 139 | 14.1 |
| 29.2 | 78 | 8 |
| 31.2 | 113 | 11.5 |
| 32.7 | 145 | 14.8 |
| 35.3 | 128 | 13.1 |
| 36.4 | 62 | 6.3 |
| 37.3 | 120 | 12.3 |
| 38.3 | 85 | 8.7 |
| 39.9 | 130 | 13.3 |
| 42.5 | 187 | 19 |

Example 31

Compound 1 Benzenesulfonic Acid Salt

To the 0.1 M solution of Compound 1 free base (0.05 mmol, 25.68 mg) in isopropyl alcohol (IPA) (0.5 mL) was added benzenesulfonic acid (0.11 mL of 0.5 M in isopropyl alcohol, 0.055 mmol, 1.1 eq.). The resultant reaction mixture was stirred overnight to give a slurry. The precipitate was removed by filtration to give Compound 1 besylate salt, which was characterized by XRPD.

Figure 39:
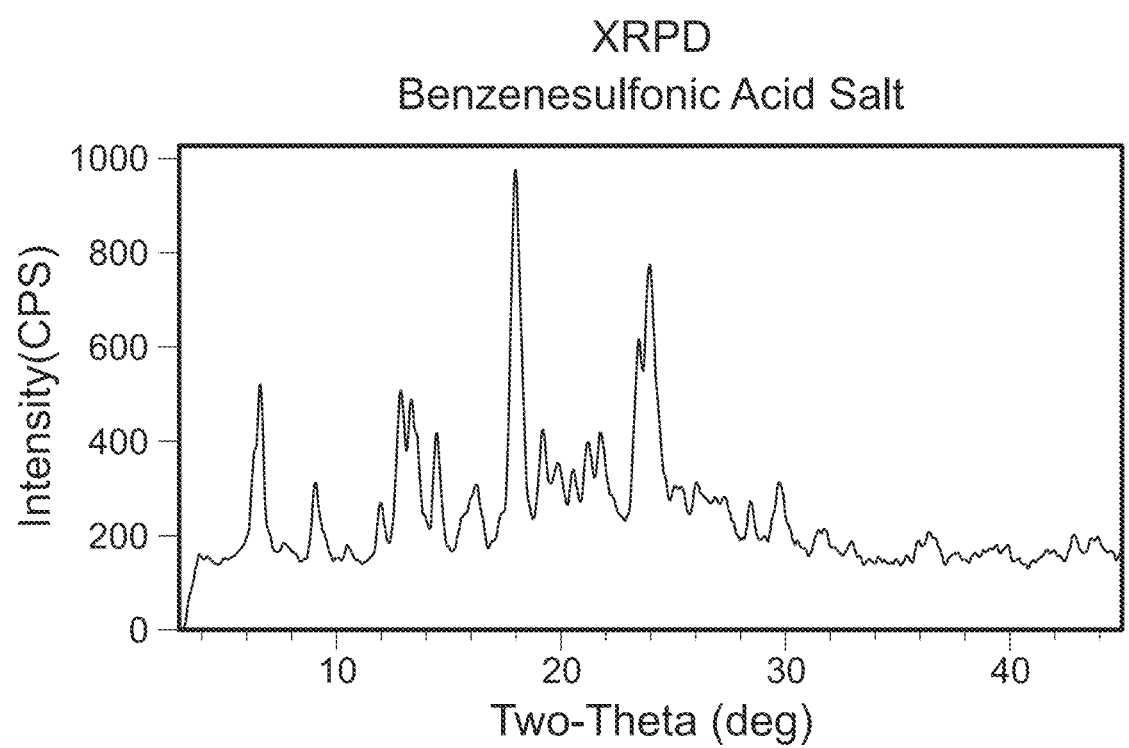
FIG. 39 shows the XRPD pattern of a solid form of Compound 1 benzenesulfonic acid salt.

Experimental parameters for acquiring the XRPD data are as described in Example 2. The XRPD pattern is shown in FIG. 39.

XRPD data is provided in Table 25.

TABLE 25

| 2-Theta (°) | Height | H % |
| --- | --- | --- |
| 3.9 | 156 | 20 |
| 6.6 | 406 | 52.1 |
| 9.1 | 188 | 24.1 |
| 12.0 | 109 | 14 |
| 12.9 | 306 | 39.2 |
| 13.3 | 267 | 34.3 |
| 14.5 | 237 | 30.4 |
| 15.7 | 56 | 7.1 |
| 16.2 | 162 | 20.7 |
| 18.0 | 780 | 100 |
| 19.2 | 197 | 25.2 |
| 19.8 | 109 | 14 |
| 20.5 | 94 | 12 |
| 21.2 | 125 | 16.1 |
| 21.8 | 182 | 23.3 |
| 23.5 | 356 | 45.7 |
| 23.9 | 522 | 66.9 |
| 25.2 | 56 | 7.1 |
| 26.1 | 79 | 10.1 |
| 28.4 | 89 | 11.4 |
| 29.7 | 148 | 18.9 |
| 31.6 | 65 | 8.4 |
| 32.9 | 46 | 5.8 |
| 35.9 | 45 | 5.7 |
| 36.4 | 69 | 8.8 |
| 39.8 | 47 | 6 |
| 42.8 | 71 | 9.1 |
| 43.7 | 52 | 6.6 |

Example 32

Compound 1 L-Pyroglutamic Acid Salt

To the 0.1 M solution of Compound 1 free base (0.05 mmol, 25.68 mg) in isopropyl alcohol (IPA) (0.5 mL) was added L-pyroglutamic acid (7.25 mg, 0.056 mmol, 1.12 eq.). The resultant reaction mixture was stirred for 5 h, after which time heptane (0.3 mL) was added. The reaction mixture was continuously stirred overnight to form a slurry. The precipitate was removed by filtration, and the filter cake was washed with methyl tert-butyl ether (MTBE) to give Compound 1 L-pyroglutamic acid salt, which was characterized by XRPD.

Figure 40:
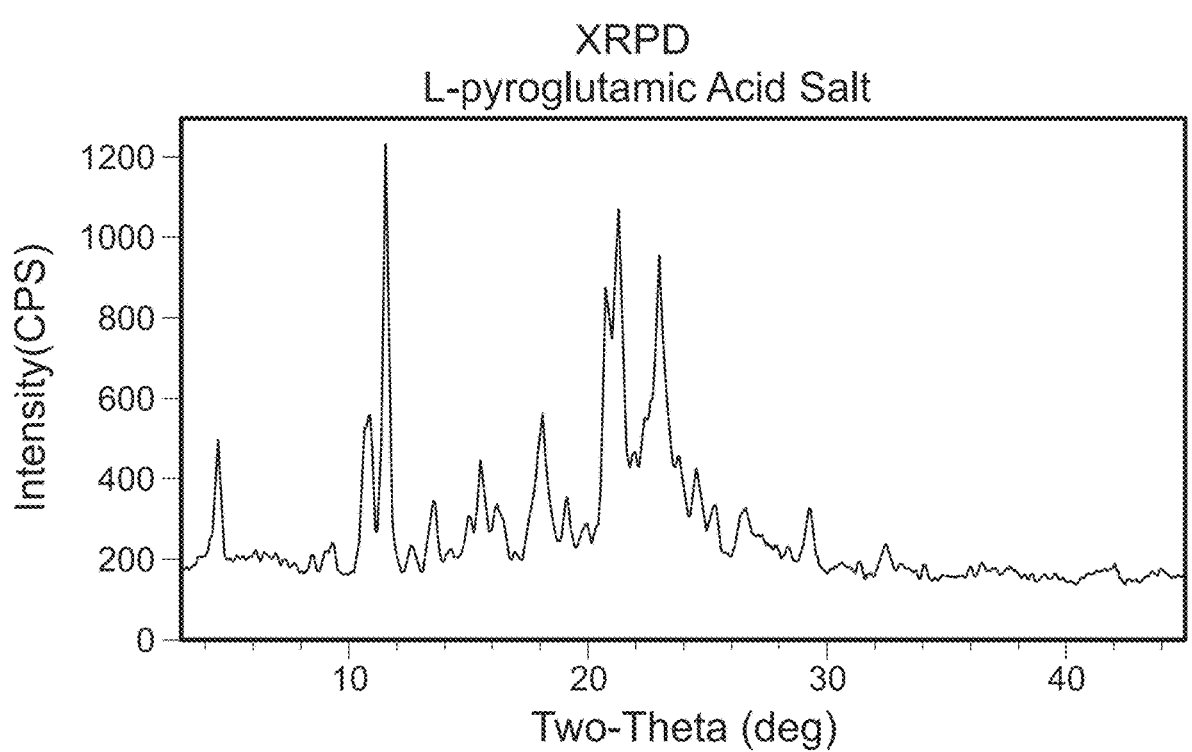
FIG. 40 shows the XRPD pattern of a solid form of Compound 1 L-pyroglutamic acid salt.

Experimental parameters for acquiring the XRPD data are as described in Example 2. The XRPD pattern is shown in FIG. 40.

XRPD data is provided in Table 26.

TABLE 26

| 2-Theta (°) | Height | H % |
|---|---|---|
| 4.4 | 344 | 32.7 |
| 8.3 | 49 | 4.6 |
| 9.2 | 86 | 8.2 |
| 10.7 | 343 | 32.6 |
| 11.5 | 1052 | 100 |
| 12.5 | 74 | 7.1 |
| 13.5 | 176 | 16.7 |
| 15.0 | 102 | 9.7 |
| 15.4 | 202 | 19.2 |
| 16.1 | 100 | 9.5 |
| 17.5 | 73 | 6.9 |
| 18.0 | 365 | 34.7 |
| 19.0 | 145 | 13.8 |
| 19.8 | 72 | 6.8 |
| 20.7 | 576 | 54.7 |
| 21.2 | 706 | 67.1 |
| 22.9 | 539 | 51.2 |
| 23.7 | 66 | 6.3 |
| 24.5 | 139 | 13.2 |
| 25.2 | 98 | 9.3 |
| 26.4 | 124 | 11.8 |
| 29.2 | 158 | 15 |
| 32.4 | 85 | 8.1 |
| 33.0 | 47 | 4.4 |
| 34.0 | 49 | 4.6 |
| 41.3 | 51 | 4.9 |
| 41.9 | 46 | 4.4 |

Example 33

Compound 1 Methanesulfonic Acid Salt

To the 0.1 M solution of Compound 1 free base (0.05 mmol, 25.68 mg) in isopropyl alcohol (IPA) (0.5 mL) was added methanesulfonic acid (0.055 mmol, 1.1 eq., 0.055 mL of 1.0 M solution in EtOH). The resultant reaction mixture was stirred for 5 h, after which time heptane (0.3 mL) was added to the reaction mixture. The reaction mixture was continuously stirred for 24 h to give a slurry. The precipitate was removed by filtration to give Compound 1 mesylate salt, which was analyzed by XRPD.

Figure 41:
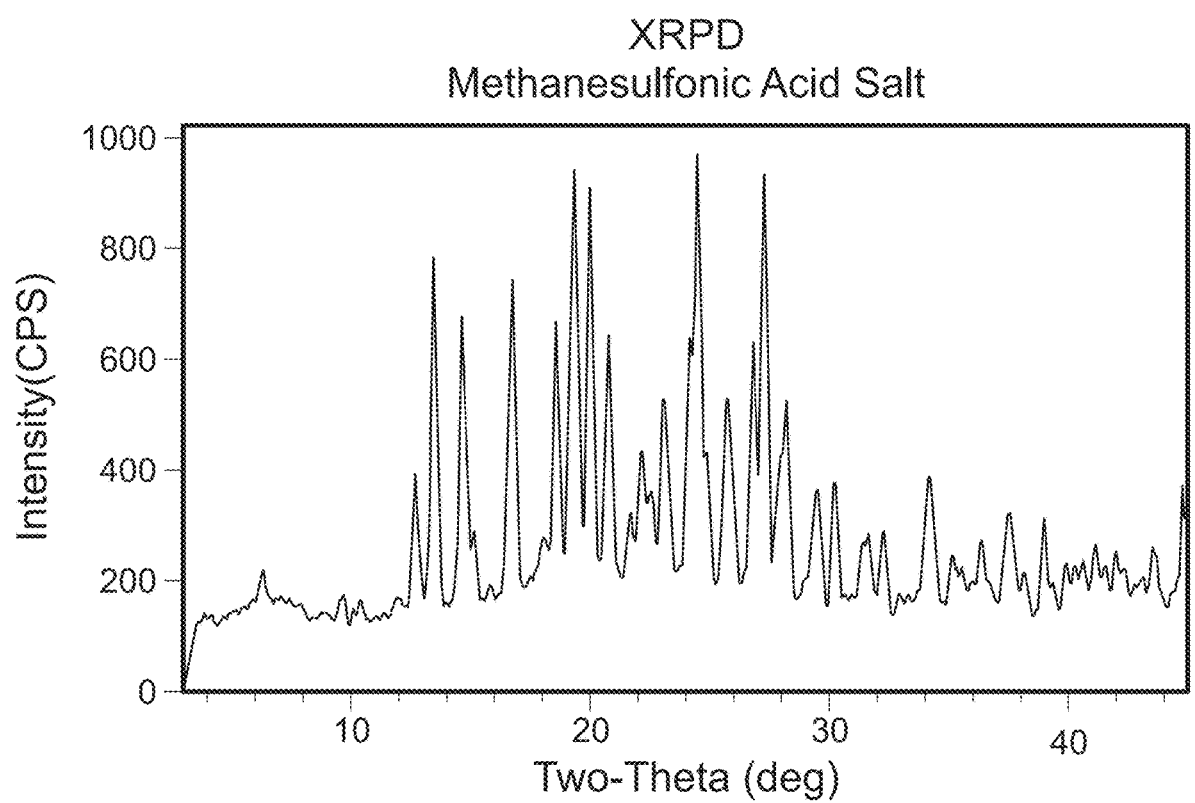
FIG. 41 shows the XRPD pattern of a solid form of Compound 1 methanesulfonic acid salt.

Experimental parameters for acquiring the XRPD data are as described in Example 2. The XRPD pattern is shown in FIG. 41.

XRPD data is provided in Table 27.

TABLE 27

| 2-Theta (°) | Height | H % |
|---|---|---|
| 3.6 | 143 | 18.6 |
| 6.4 | 60 | 7.8 |

TABLE 27-continued

| 2-Theta (°) | Height | H % |
|---|---|---|
| 9.6 | 55 | 7.1 |
| 10.4 | 44 | 5.7 |
| 12.7 | 222 | 28.9 |
| 13.5 | 650 | 84.6 |
| 14.7 | 528 | 68.7 |
| 15.1 | 135 | 17.6 |
| 16.7 | 598 | 77.8 |
| 18.6 | 425 | 55.3 |
| 19.3 | 697 | 90.7 |
| 20.0 | 697 | 90.8 |
| 20.7 | 434 | 56.5 |
| 21.6 | 81 | 10.6 |
| 22.1 | 214 | 27.9 |
| 22.4 | 146 | 19 |
| 23.0 | 295 | 38.5 |
| 24.1 | 447 | 58.2 |
| 24.4 | 768 | 100 |
| 24.8 | 234 | 30.4 |
| 25.7 | 354 | 46.1 |
| 26.8 | 434 | 56.5 |
| 27.2 | 715 | 93.1 |
| 28.1 | 364 | 47.3 |
| 29.4 | 240 | 31.3 |
| 30.1 | 236 | 30.7 |
| 31.5 | 138 | 17.9 |
| 32.1 | 140 | 18.2 |
| 34.1 | 236 | 30.8 |
| 35.0 | 94 | 12.2 |
| 35.4 | 71 | 9.2 |
| 36.2 | 120 | 15.6 |
| 37.4 | 196 | 25.5 |
| 38.0 | 73 | 9.5 |
| 38.8 | 183 | 23.8 |
| 39.8 | 90 | 11.7 |
| 40.1 | 61 | 8 |
| 40.4 | 59 | 7.7 |
| 41.0 | 76 | 9.9 |
| 41.4 | 54 | 7 |
| 41.9 | 70 | 9.1 |
| 42.1 | 49 | 6.4 |
| 42.9 | 67 | 8.7 |
| 43.4 | 108 | 14 |

Example 34

Compound 1 (1S)-(+)-10-camphorsulfonic Acid Salt

To the 0.1 M solution of Compound 1 free base (0.05 mmol, 25.68 mg) in isopropyl alcohol (IPA) (0.5 mL) was added (1S)-(+)-10-camphorsulfonic acid (0.055 mmol, 1.1 eq., 0.11 mL of 0.5 M solution in IPA) (CAS registry number 3144-16-9; Aldrich catalog number C2107-500G). The resultant reaction mixture was stirred for 5 h, after which time heptane (0.3 mL) was added to the reaction mixture. The reaction mixture was continuously stirred overnight to give a slurry. The precipitate was removed by filtration to give Compound 1 camsylate salt, which was analyzed by XRPD.

Figure 42:
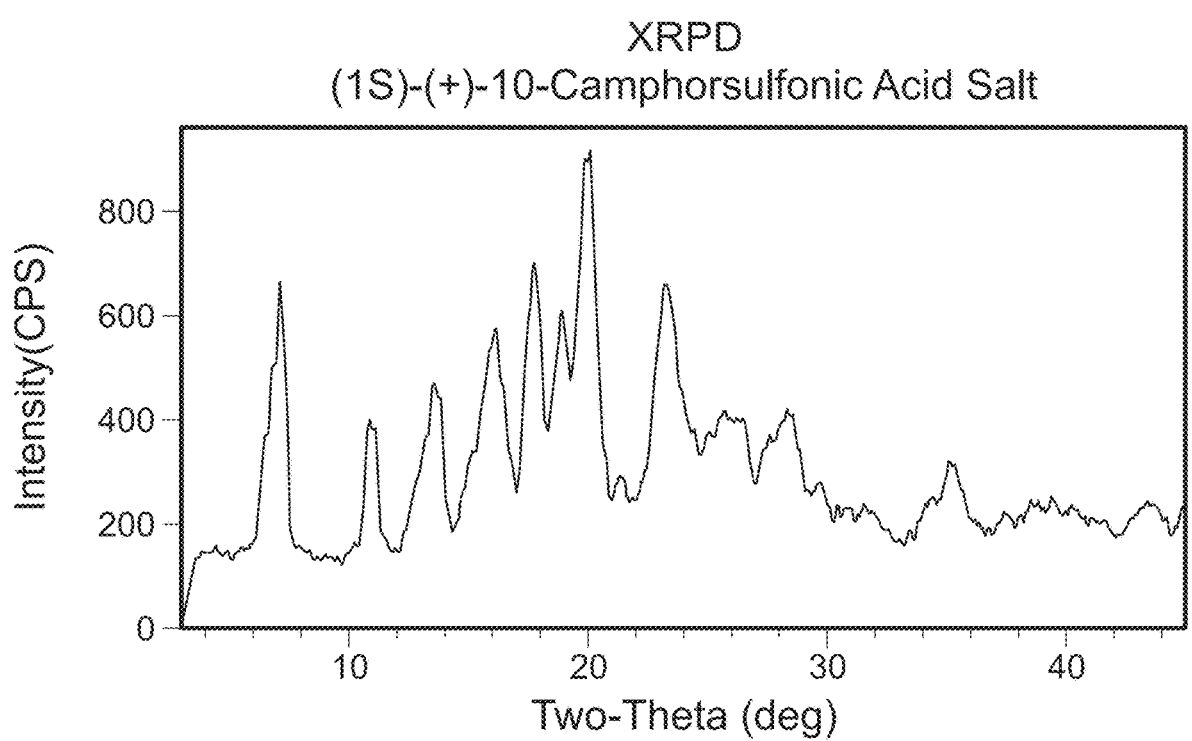
FIG. 42 shows the XRPD pattern of a solid form of Compound 1 (1S)-(+)-10-camphorsulfonic acid salt.

Experimental parameters for acquiring the XRPD data are as described in Example 2. The XRPD pattern is shown in FIG. 42.

XRPD data is provided in Table 28.

TABLE 28

| 2-Theta (°) | Height | H % |
|---|---|---|
| 3.7 | 140 | 25.9 |
| 6.6 | 232 | 43 |
| 7.1 | 539 | 100 |
| 10.9 | 249 | 46.1 |

TABLE 28-continued

| 2-Theta (°) | Height | H % |
|---|---|---|
| 13.6 | 249 | 46.2 |
| 16.1 | 292 | 54.1 |
| 17.7 | 372 | 69 |
| 18.8 | 188 | 34.8 |
| 19.9 | 500 | 92.7 |
| 21.3 | 70 | 12.9 |
| 23.2 | 321 | 59.6 |
| 25.6 | 90 | 16.7 |
| 28.4 | 124 | 22.9 |
| 29.6 | 62 | 11.5 |
| 31.7 | 60 | 11.1 |
| 35.1 | 99 | 18.4 |
| 43.5 | 64 | 11.8 |

Example 35

Compound 1 Fumaric Acid Salt

To the 0.1 M solution of Compound 1 free base (0.05 mmol, 25.68 mg) in isopropyl alcohol (IPA) (0.5 mL) was added maleic acid (6.69 mg, 0.058 mmol, 1.16 eq.). The reaction mixture was stirred for 5 h, after which time heptane (0.3 mL) was added to the reaction mixture. The reaction mixture was continuously stirred overnight to give a slurry. The precipitate was removed by filtration to give Compound 1 fumarate salt, which was analyzed by XRPD.

Figure 43:
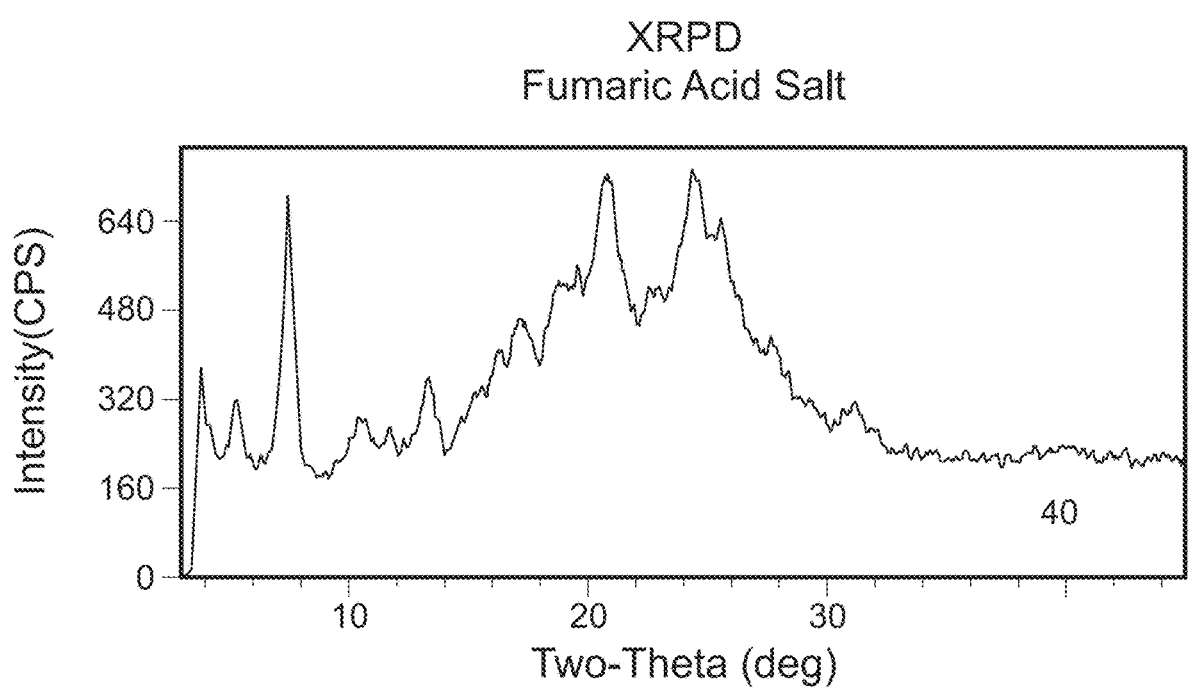
FIG. 43 shows the XRPD pattern of a solid form of Compound 1 fumaric acid salt.

Compound 1 fumaric acid salt was characterized by XRPD. Experimental parameters for acquiring the XRPD data are as described in Example 2. The XRPD pattern is shown in FIG. 43.

XRPD data is provided in Table 29.

TABLE 29

| 2-Theta (°) | Height | H % |
|---|---|---|
| 3.8 | 397 | 77.6 |
| 5.2 | 120 | 23.4 |
| 7.3 | 511 | 100 |
| 10.4 | 89 | 17.4 |
| 11.6 | 74 | 14.5 |
| 13.2 | 145 | 28.4 |
| 16.2 | 68 | 13.3 |
| 17.1 | 126 | 24.6 |
| 20.8 | 239 | 46.7 |
| 24.3 | 216 | 42.2 |
| 25.6 | 81 | 15.9 |
| 27.8 | 78 | 15.3 |
| 31.1 | 71 | 13.9 |
| 41.9 | 52 | 10.1 |

Example 36

Compound 1 Sulfuric Acid Salt

To the 0.1 M solution of Compound 1 free base (0.05 mmol, 25.68 mg) in IPA (0.5 mL) was added sulfuric acid (0.055 mmol, 1.1 eq., 0.055 mL of 1.0 M solution in IPA). The reaction mixture was stirred overnight to give a slurry. The precipitate was removed by filtration to give Compound 1 sulfate salt, which was characterized by XRPD.

Figure 44:
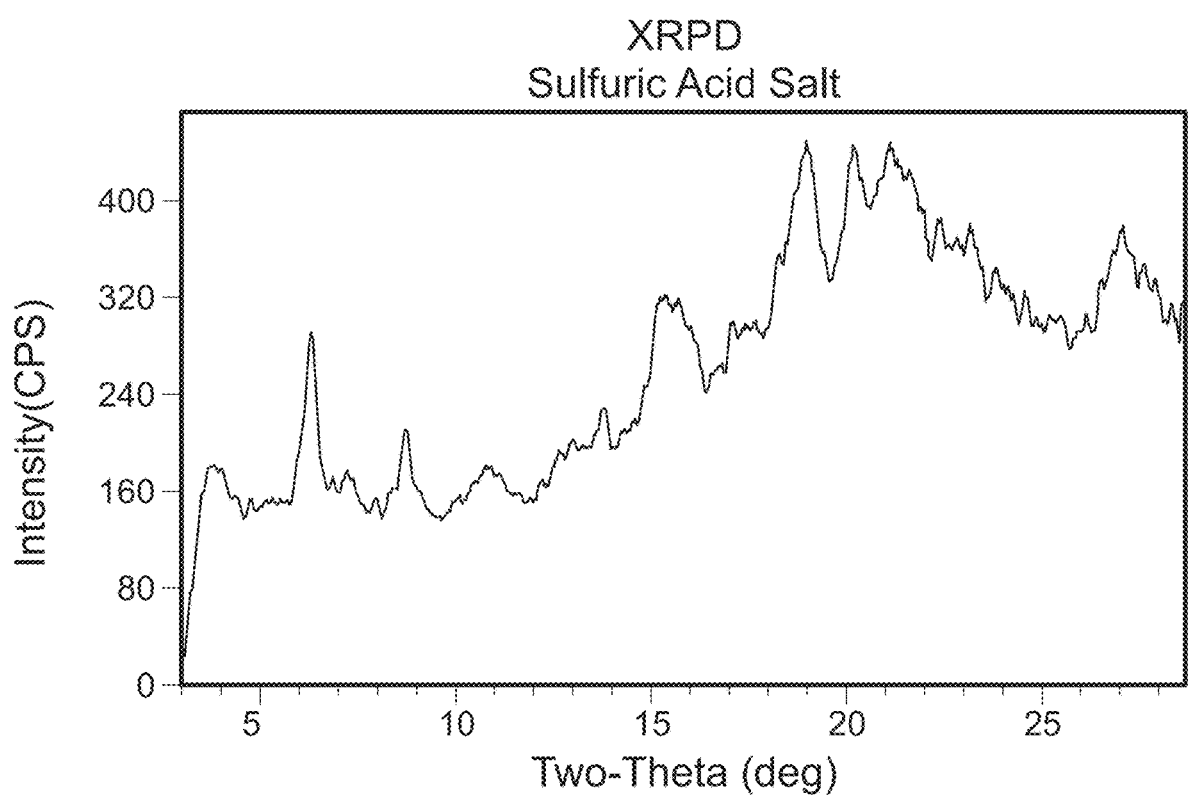
FIG. 44 shows the XRPD pattern of a solid form of Compound 1 sulfuric acid salt.

Compound 1 sulfuric acid salt was characterized by XRPD. Experimental parameters for acquiring the XRPD data are as described in Example 2. The XRPD pattern is shown in FIG. 44.

XRPD data is provided in Table 30.

TABLE 30

| 2-Theta (°) | Height | H % |
|---|---|---|
| 3.6 | 185 | 100 |
| 6.3 | 169 | 91.8 |
| 8.7 | 89 | 48.3 |
| 10.8 | 54 | 29.1 |
| 12.8 | 51 | 27.6 |
| 13.7 | 57 | 31.1 |
| 15.4 | 132 | 71.7 |
| 19.0 | 152 | 82.1 |
| 20.2 | 114 | 62 |
| 21.2 | 85 | 46 |
| 21.6 | 114 | 61.9 |
| 23.1 | 76 | 40.9 |
| 24.0 | 62 | 33.4 |
| 24.8 | 68 | 36.6 |
| 25.4 | 59 | 31.8 |
| 27.1 | 110 | 59.6 |
| 27.2 | 111 | 60.4 |

Example 37

Compound 1 L-Tartaric Acid Salt

To the 0.1 M solution of Compound 1 free base (0.05 mmol, 25.68 mg) in isopropyl alcohol (IPA) (0.5 mL) was added L-tartaric acid (8.71 mg, 0.058 mmol, 1.16 eq.). The reaction mixture was stirred for 5 h, after which time heptane (0.3 mL) was added to the reaction mixture. The reaction mixture was continuously stirred overnight to give a slurry. The precipitate was removed by filtration to give Compound 1 L-tartrate salt, which was analyzed by XRPD.

Figure 45:
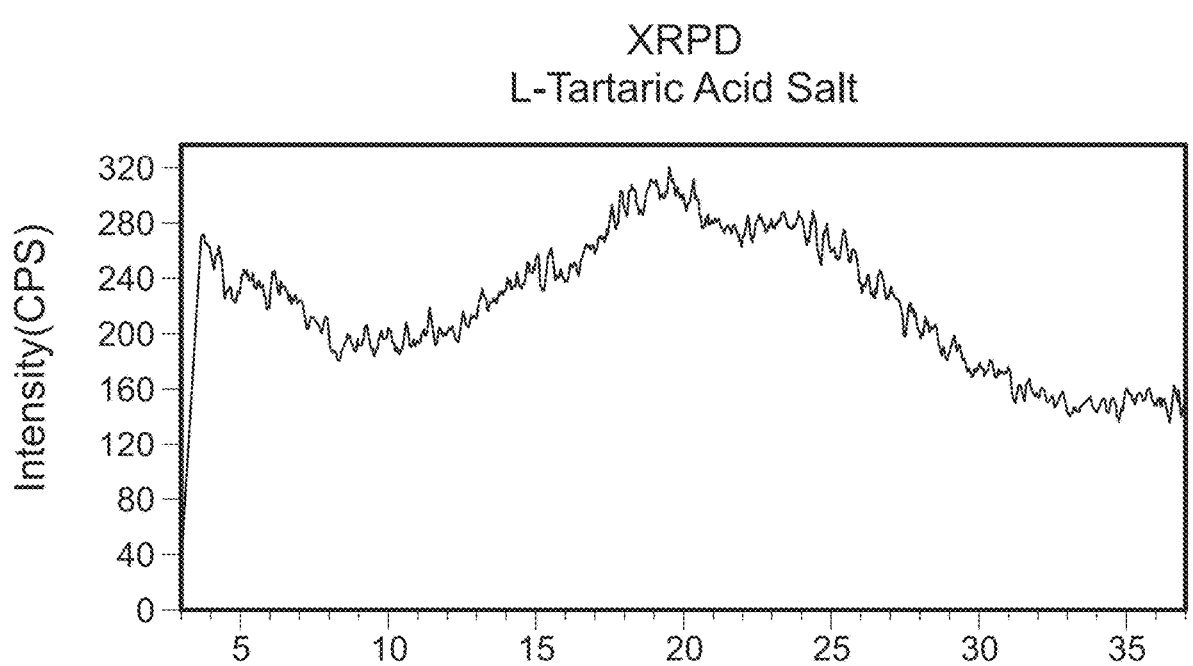
FIG. 45 shows the XRPD pattern of a solid form of Compound 1 L-tartaric acid salt.

Compound 1 L-tartaric acid salt was obtained as amorphous solid. Experimental parameters for acquiring the XRPD data are as described in Example 2. The XRPD pattern is shown in FIG. 45.

Example 38

Compound 1 D-Tartaric Acid Salt

To the 0.1 M solution of Compound 1 free base (0.05 mmol, 25.68 mg) in IPA (0.5 mL) was added D-tartaric acid (8.64 mg, 0.058 mmol, 1.16 eq.). The reaction mixture was stirred for 5 h, after which time heptane (0.3 mL) was added to the reaction mixture. The reaction mixture was continuously stirred overnight to give a slurry. The precipitate was removed by filtration to give Compound 1 D-tartrate salt, which was analyzed by XRPD.

Figure 46:
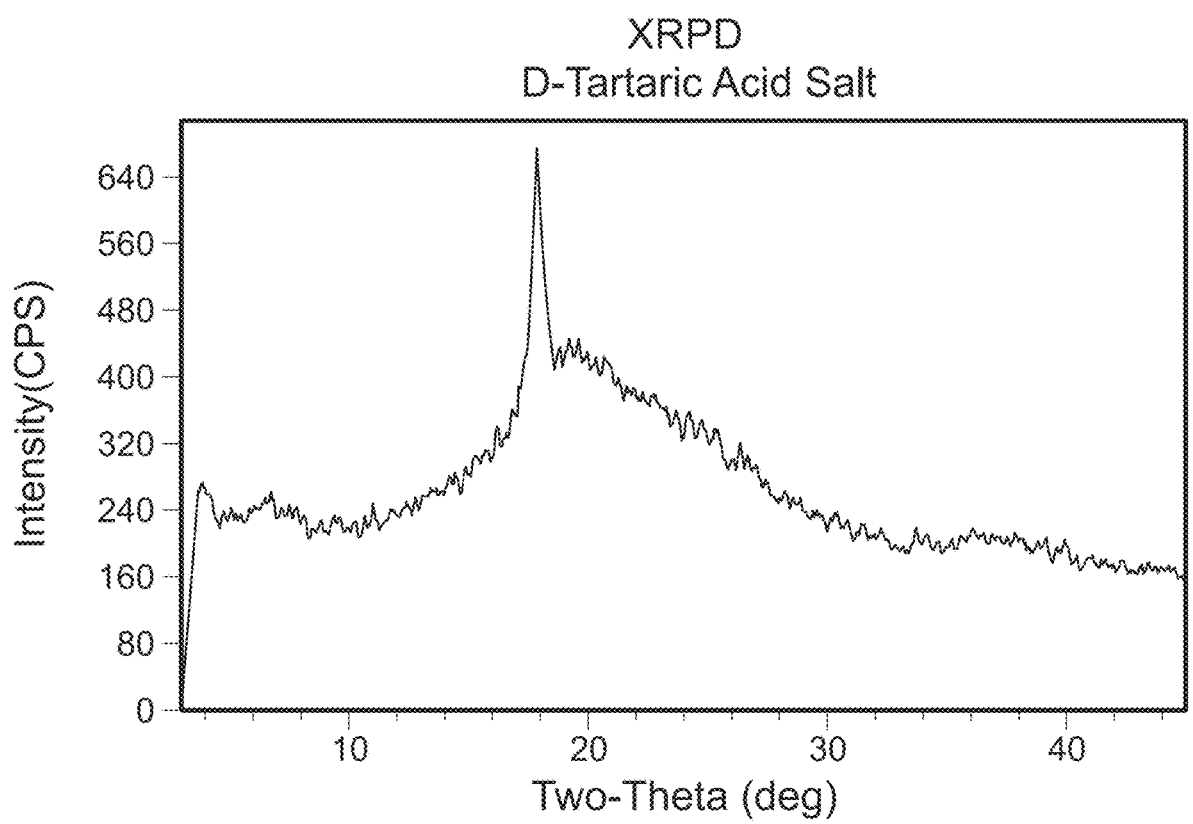
FIG. 46 shows the XRPD pattern of a solid form of Compound 1 D-tartaric acid salt.

Compound 1 D-tartaric acid salt was obtained as amorphous solid (the XRPD pattern is shown in FIG. 46).

Example A

Pim Enzyme Assays

Pim-1 and Pim-3 kinase assays-20 µL reactions can be run in white 384 well polystyrene plates dotted with 0.8 µL compound/DMSO in the assay buffer (50 mM Tris, pH 7.5, 0.01% Tween-20, 5 mM $MgCl_2$, 0.01% BSA, 5 mM DTT), containing 0.05 µM Biotin-labeled BAD peptide substrate (AnaSpec 62269), 1 mM ATP, and 2.5 pM (Pim-1, Invitrogen PV3503) or 1.25 pM (Pim-3, Millipore 14-738) enzyme for 1 h at 25° C. Reactions are stopped by addition of L STOP Buffer (150 mM Tris, pH=7.5, 150 mM NaCl, 75 mM EDTA, 0.01% Tween-20, 0.3% BSA) supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 µg/mL each. Supplementation of the STOP buffer with beads and stopping the reactions are done under reduced light. Prior to the stopping reactions STOP buffer with beads is pre-incubated for 1 h in the dark at room temperature. After stopping the reactions, plates are incubated for 1 h in the dark at room temperature before reading on a PHERAstar FS plate reader (BMG Labtech) under reduced light.

Pim-2 kinase assay-20 µL reactions are run in white 384 well polystyrene plates dotted with 0.8 µL compound/DMSO in the assay buffer (50 mM Tris, pH 7.5, 0.01% Tween-20, 5 mM $MgCl_2$, 0.01% BSA, 5 mM DTT), containing 0.05 µM Fluorescein-labeled CREBtide peptide substrate (Invitrogen PV3508), 1 mM ATP, and 1 nM enzyme (Invitrogen PV3649) for 2 h at 25° C. Reactions are stopped by addition of 10 µL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates are read on a PHERAstar FS plate reader (BMG Labtech).

Compounds or salts of the invention having an $IC_{50}$ of 2 µM or less when tested for PIM kinase activity under the assay conditions disclosed above are considered active. Compound 1 was tested according to this assay and found to have an $IC_{50}$<100 nM. Compound 1 phosphate salt and Compound 1 dihydrochloric acid salt were tested according to this assay and data is provided below in Table 16.

Although the above in vitro assays are conducted at 1 mM ATP, compounds can also be evaluated for potency and in vitro activity against PIM targets utilizing $K_m$ conditions, where the concentration of ATP is set to the $K_m$ value and the assay is more sensitive to PIM inhibition activity.

Example B

Pim Cellular and Whole Blood Assays
Pim Cell Proliferation Assays

KMS12BM and MOLM16 cells were purchased from DSMZ (Germany) and were maintained according to the recommendations of suppliers. To measure the anti-proliferation activities of test compounds, the cells were plated in their respective culture medium (2×103 cells/200 µL/well) into 96-well ultralow binding plates (Corning), with or without test compound(s). After 3 to 4 days, [3H]-thymidine (1 µCi/well) (PerkinElmer) in PBS (10 µL) was then added to the cell culture for an additional 12 hours before the incorporated radioactivity was separated by filtration with water through GF/B filters (Packard Bioscience) and measured by liquid scintillation counting with a TopCount (Packard Bioscience).

Pim pBAD Signaling Assays

To measure the effect of test compounds on the level of pBAD in cells, KMS12BM cells (DSMZ, Germany) were plated with RPMI and 10% FBS (4×10$^5$ cells/well/100 µL) into 96-well v-bottom polypropylene plates (Greiner) in the presence or absence of 5 µL of a concentration range test compound(s). After 2.5 hours at 37° C. and 5% $CO_2$, the cells were lysed in 100 µL of cell extraction buffer (Cell Signaling Technology) containing PMSF, HALT, and protease inhibitors (Thermo, EMD Calbiochem). pBAD protein in the cell lysates was quantified with the Human pBAD S112 ELISA Kit (Cell Signaling Technology). $IC_{50}$ determination was performed by fitting the curve of percent inhibition versus the log of the inhibitor concentration using the GraphPad Prism 5.0 software To measure the effect of test compounds on the level of pBAD in cells in the presence of human whole blood, human heparinized whole blood (Biological Specialty Corp, Colmar Pa.) was obtained and 350 µL/well was added to a 96-well 2 mL block plate (Costar 3961) in the presence or absence of 20 µL of a concentration range of test compound(s). KMS12BM cells (1×10$^6$) or MOLM-16 cell (5×10$^5$) (DSMZ, Germany) in 25 µL of RPMI and 10% FBS (GIBCO) were added to each well. After 2.5 hours at 37° C. and 5% $CO_2$, red blood cells were lysed with erythrocyte lysis buffer (Qiagen) and the remaining cells were centrifuged at 1200 RPM. The resulting pellets were lysed with 100 µL of cell extraction buffer (Cell Signaling Technology) containing Halt, PMSF, and protease inhibitors (Thermo, Calbiochem, Sigma). The level of pBAD protein in the cell lysates were then quantified in a commercial Human pBAD S112 ELISA Kit (Cell Signaling Technology). $IC_{50}$ determination was performed by fitting the curve of percent inhibition versus the log of the inhibitor concentration using the GraphPad Prism 5.0 software.

Example C

Assay Data

Both Compound 1 phosphoric acid salt and Compound 1 dihydrochloric acid salt were tested in the above-described assays of Examples A and B. Data is provided below in Table 30.

TABLE 30

| Assay Type (Example No., cell type) | $IC_{50}$ (nM) Compound 1 di-HCl salt | $IC_{50}$ (nM) Compound 1 H3PO4 salt |
|---|---|---|
| PIM1 Enzyme (Ex. A) | <35 | <35 |
| PIM2 Enzyme (Ex. A) | <35 | <35 |
| PIM3 Enzyme (Ex. A) | <35 | <35 |
| Tumor cell proliferation (Ex. B, KMS12BM cells) | <100 | <100 |
| Tumor cell proliferation (Ex. B, MOLM16 cells) | <35 | <35 |
| pBAD KMS12BM cells (Ex. B) | <35 | <35 |
| pBAD whole blood (Ex. B, KMS12BM cells) | <200 | <200 |
| pBAD whole blood (Ex. B, MOLM16 cells) | <100 | <100 |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A salt which is a hydrochloric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

2. The salt of claim 1, wherein the salt is a dihydrochloric acid salt.

3. A solid form of the salt of claim 2.

4. The solid form of claim 3 which is crystalline.

5. The solid form of claim 4 having an XRPD pattern substantially as shown in FIG. 4.

6. The solid form of claim 4 having a melting point of about 213° C.

7. The salt of claim 1, wherein the salt is a monohydrochloric acid salt.

8. A solid form of the salt of claim 7.

9. The solid form of claim 8 which is crystalline.

10. The solid form of claim 9 having an XRPD pattern substantially as shown in FIG. 22.

11. The solid form of claim 9 having a melting point of about 209° C.

12. The solid form of claim 4 having a DSC thermogram substantially as shown in FIG. 5.

13. The solid form of claim 4 having a TGA thermogram substantially as shown in FIG. 6.

14. The solid form of claim 4 having at least one characteristic XRPD peak, in terms of 2-theta, selected from about 8.3, about 18.9, and about 25.0 degrees.

15. The solid form of claim 4 having two or more characteristic XRPD peak, in terms of 2-theta, selected from about 8.3, about 18.9, and about 25.0 degrees.

16. The solid form of claim 9 having a DSC thermogram substantially as shown in FIG. 23.

17. The solid form of claim 9 having at least one characteristic XRPD peak, in terms of 2-theta, selected from about 7.8, about 8.8, about 12.6, about 14.5, about 17.4, about 23.8, and about 25.2 degrees.

18. The solid form of claim 9 having two or more characteristic XRPD peak, in terms of 2-theta, selected from about 7.8, about 8.8, about 12.6, about 14.5, about 17.4, about 23.8, and about 25.2 degrees.

19. The solid form of claim 9 having three or more characteristic XRPD peak, in terms of 2-theta, selected from about 7.8, about 8.8, about 12.6, about 14.5, about 17.4, about 23.8, and about 25.2 degrees.

* * * * *